(12) United States Patent
Zhu et al.

(10) Patent No.: US 10,842,151 B2
(45) Date of Patent: Nov. 24, 2020

(54) SMALL MOLECULE COMPOUND FOR ENHANCING PLANT STRESS RESISTANCE

(71) Applicant: SHANGHAI INSTITUTES FOR BIOLOGICAL SCIENCES, CHINESE ACADEMY OF SCIENCES, Shanghai (CN)

(72) Inventors: Jiankang Zhu, Shanghai (CN); Minjie Cao, Shanghai (CN); Yulu Zhang, Shanghai (CN); Xue Liu, Shanghai (CN)

(73) Assignee: CAS CENTER FOR EXCELLENCE IN MOLECULAR PLANT SCIENCES, Shanghai (CN)

( * ) Notice: Subject to any disclaimer, the term of this patent is extended or adjusted under 35 U.S.C. 154(b) by 0 days.

(21) Appl. No.: 15/756,075

(22) PCT Filed: Apr. 29, 2016

(86) PCT No.: PCT/CN2016/080790
§ 371 (c)(1),
(2) Date: Feb. 28, 2018

(87) PCT Pub. No.: WO2017/036153
PCT Pub. Date: Mar. 9, 2017

(65) Prior Publication Data
US 2018/0360039 A1    Dec. 20, 2018

(30) Foreign Application Priority Data
Aug. 28, 2015  (CN) .......................... 2015 1 0542444

(51) Int. Cl.
*A01N 43/42*     (2006.01)
*A01N 3/00*      (2006.01)
*C07D 215/38*    (2006.01)
*A01H 6/88*      (2018.01)

(52) U.S. Cl.
CPC .............. *A01N 43/42* (2013.01); *A01N 3/00* (2013.01); *C07D 215/38* (2013.01); *A01H 6/88* (2018.05)

(58) Field of Classification Search
CPC ......... C07D 215/38; A01N 43/42; A01N 3/00
See application file for complete search history.

(56) References Cited

U.S. PATENT DOCUMENTS

2016/0280651 A1\* 9/2016 Cutler .................. C07D 215/22
2017/0027172 A1\* 2/2017 Frackenpohl .......... A01N 43/42

FOREIGN PATENT DOCUMENTS

| CN | 104170823   | 12/2014 |
| WO | WO2014210555 | 12/2014 |
| WO | WO2015155154 | 10/2015 |
| WO | WO2016022915 | 2/2016  |

\* cited by examiner

*Primary Examiner* — John Pak
(74) *Attorney, Agent, or Firm* — Adam Warwick Bell; Matthew Rupert Kaser; Joseph Curtis Edmondson

(57) ABSTRACT

Disclosed are a small molecule compound for enhancing plant stress resistance, a preparation method therefor, and application thereof. Specifically, disclosed are compounds as shown in formula I, salts thereof, optical isomers thereof, racemes thereof, solvates thereof, or precursors thereof. Moreover, the compound of the present invention is a substitute of ABA, can significantly improve the plant stress resistance, and thus has an extremely wide application prospect.

7 Claims, 24 Drawing Sheets

ABA h

1125A c        14 days after treatment with 10μM compound

One month after re-watering 1 day after re-watering

SMALL MOLECULE COMPOUND FOR ENHANCING PLANT STRESS RESISTANCE

TECHNICAL FIELD

The present invention relates to the field of botany, in particular to compounds for enhancing plant stress resistance and the preparation and use thereof.

BACKGROUND ART

Abscisic Acid (ABA) is a key factor that balances plant endogenous hormones and metabolism of related growth-active substances, which has the ability to promote plants to absorb water and fertilizer in balance and coordinate metabolism in vivo, can effectively regulate the root/crown of the plants, and vegetative growth and reproductive growth in plants, and plays an important role in improving the quality and the yield of crops. Through the application of ABA, there is an important physiological activity effect and application value in improving the quality of agricultural products and many other aspects. In addition, exogenous ABA can cause rapid closure of leaf stomatal and inhibition of transpiration, which can be used for the preservation of flower, or preventing wilting during the transportational process of crop seedling transplanting cultivation. ABA can also control flower bud differentiation, regulate flowering phase, which possesses a great application value in the aspects of flower and gardening.

ABA can improve the crop growth in the low temperature, drought, spring chill, salt and other undesirable growth environments. Therefore, ABA is widely used in a lawn, farmland and garden, especially in the water-deficient areas, such as the western region, which is of great significance to the development of China's agricultural industry.

However, natural active (+)-ABA is unstable and difficult to be synthesized, which results in a high production cost. Therefore, ABA has not been widely used for agricultural production, while scientists from all over the world are developing alternatives to natural ABA.

So far although some alternatives to ABA have been developed, the activity of these alternatives is unsatisfactory, whose application value in agricultural production is low. In addition, some alternatives have less environmentally friendliness.

Therefore, there is an urgent need in the art to develop compounds which are environmentally friendly and can effectively increase the plant stress resistance.

SUMMARY OF THE INVENTION

The object of the present invention is to provide a compound, which is environmentally friendly and can effectively increase the plant stress resistance and the preparation and use thereof.

In the first aspect of the present invention, a compound represented by formula (I), or a salt, or an optical isomer or a raceme, or a solvate, or a precursor thereof is provided,

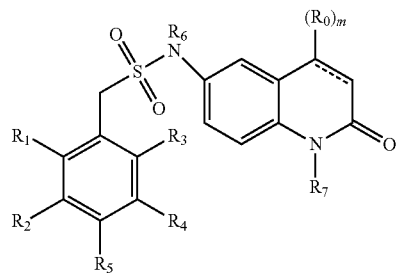

wherein,
$R_1$ is H, halogen, $C_1$-$C_3$ alkyl, or $C_1$-$C_3$ haloalkyl;
$R_2$ is H, halogen, $C_1$-$C_3$ alkyl, or $C_1$-$C_3$ haloalkyl;
$R_3$ is H, halogen, $C_1$-$C_3$ alkyl, or $C_1$-$C_3$ haloalkyl;
$R_4$ is H, halogen, $C_1$-$C_3$ alkyl, or $C_1$-$C_3$ haloalkyl;
$R_5$ is halogen, $C_1$-$C_3$ alkyl, $C_1$-$C_3$ haloalkyl or $SF_5$;
$R_6$ is H, $C_1$-$C_3$ alkyl, or $C_1$-$C_3$ haloalkyl;
$R_7$ is $C_1$-$C_7$ alkyl, $C_2$-$C_7$ alkenyl, $C_2$-$C_7$ alkynyl, $C_3$-$C_7$ cycloalkyl, or —$R_8$—O—$R_9$, wherein $R_8$ is $C_1$-$C_2$ alkylene, whereas $R_9$ is H, $C_1$-$C_3$ alkyl;
$R_0$ is H, $C_1$-$C_4$ alkyl, $C_1$-$C_4$ haloalkyl, or halogen;
m is 1 or 2;
'=====' represents a single bond or a double bond;
provided that 1 to 4 of $R_1$, $R_2$, $R_3$, $R_4$ are halogen.
In another preferred embodiment, the compound is represented by formula Ia, Ib or Ic:

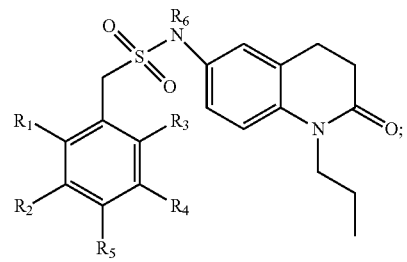

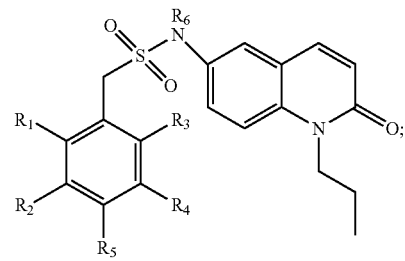

or

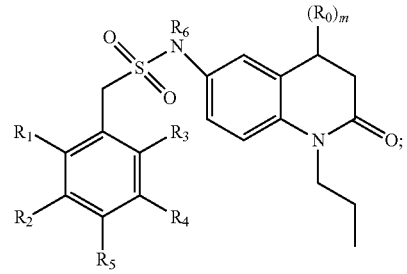

wherein the definitions of $R_0$, $R_1$-$R_6$, and m are described as above.

In another preferred embodiment, 2 to 4 of $R_1$, $R_2$, $R_3$, and $R_4$ are halogen.

In another preferred embodiment, 3 or 4 of $R_1$, $R_2$, $R_3$, and $R_4$ are halogen.

In another preferred embodiment, 4 of $R_1$, $R_2$, $R_3$, and $R_4$ are halogen.

In another preferred embodiment, the halogen includes F, Cl, Br or I.

In another preferred embodiment, the halogen includes F or Cl.

In another preferred embodiment, the halogen is F.

In another preferred embodiment, 2 to 4 of $R_1$, $R_2$, $R_3$, and $R_4$ are F.

In another preferred embodiment, 3 or 4 of $R_1$, $R_2$, $R_3$, and $R_4$ are F.

In another preferred embodiment, 4 of $R_1$, $R_2$, $R_3$, and $R_4$ are F.

In another preferred embodiment, $R_1$ and/or $R_3$ is F.

In another preferred embodiment, $R_2$ and/or $R_4$ is F.

In another preferred embodiment, $R_5$ is methyl, Cl, trifluoromethyl, or $SF_5$.

In another preferred embodiment, $R_6$ is H.

In another preferred embodiment, $R_7$ is $C_3$ alkyl, or $C_3$ alkenyl.

In another preferred embodiment, $R_7$ is n-propyl, or —$CH_2$—CH=$CH_2$.

In another preferred embodiment, when m=2, $R_0$ is same or different.

In another preferred embodiment, $R_0$ is H, or methyl.

In another preferred embodiment, the compound is selected from the group consisting of:

0604c
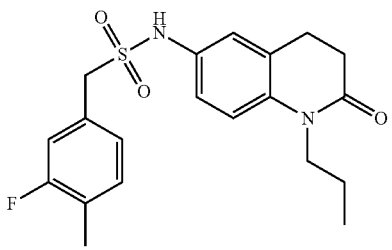

1125A
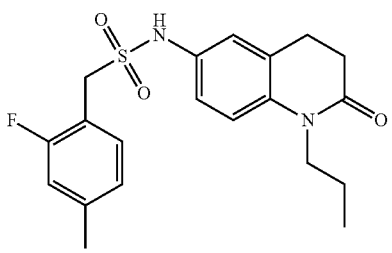

1125B
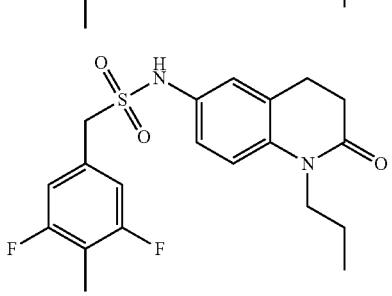

-continued

0918
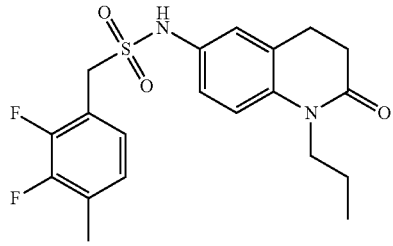

1127
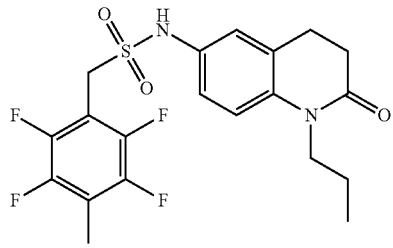

1020A
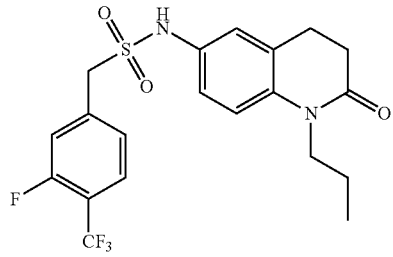

1020B
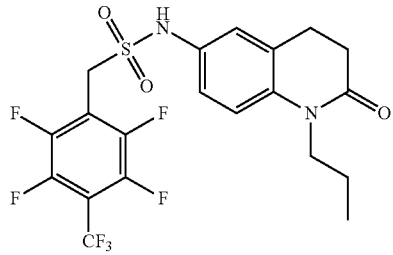

1103B
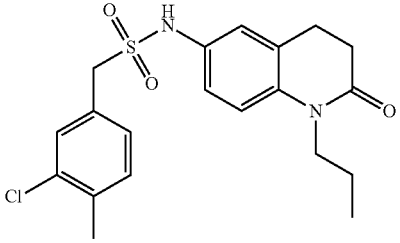

0925
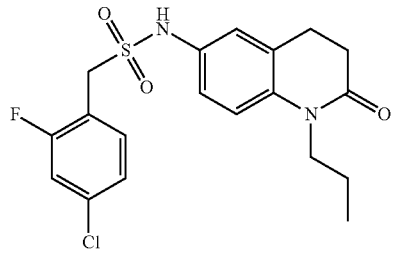

0703B
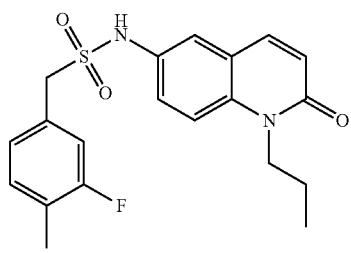

0707
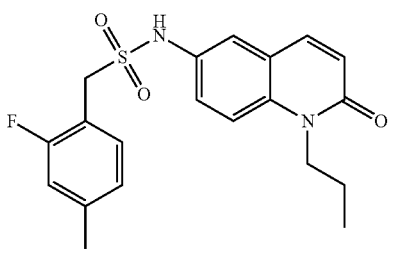

0714
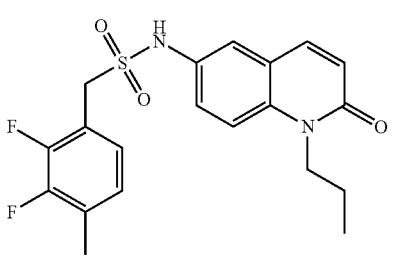

0717

130925AMX

140228AMX

0720B
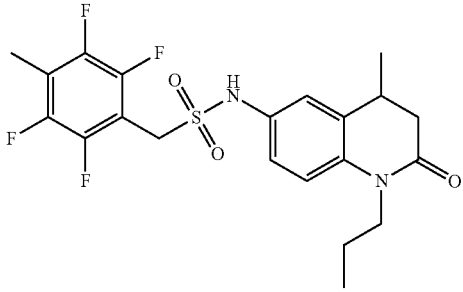

0825A
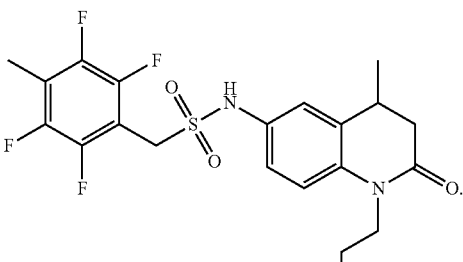

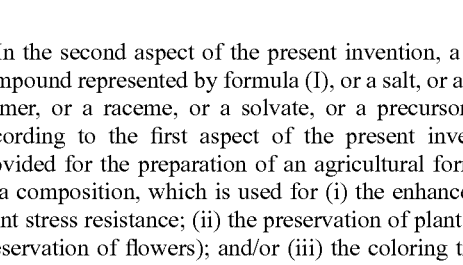

In the second aspect of the present invention, a use of a compound represented by formula (I), or a salt, or an optical isomer, or a raceme, or a solvate, or a precursor thereof according to the first aspect of the present invention is provided for the preparation of an agricultural formulation or a composition, which is used for (i) the enhancement of plant stress resistance; (ii) the preservation of plant (such as preservation of flowers); and/or (iii) the coloring treatment of fruit (such as grape coloring).

In another preferred embodiment, the agricultural formulation or the composition is used for one or more of the following usages:

(i) promoting the interaction of the ABA receptor PYL protein with the PP2C protein phosphatase;

(ii) reducing the transpiration of the leaves;

(iii) inhibiting the seed germination.

In another preferred embodiment, the stress resistance is ABA-related abiotic stress resistance.

In another preferred embodiment, the stress resistance is selected from the group consisting of: a drought resistance, a cold tolerance, a salt tolerance, an osmotic pressure resistance, a heat resistance, and a combination thereof.

In another preferred embodiment, the plant is a plant that contains ABA receptor(s) of PYR/PYL family.

In another preferred embodiment, the plant comprises a moss, a fern, a gymnosperm, a monocotyledon and a dicot.

In another preferred embodiment, the plant comprises an agricultural plant, a horticultural plant, and a forestry plant.

In another preferred embodiment, the plant comprises a woody plant, and an herb.

In another preferred embodiment, the plant comprises a complete plant, an organ (such as a root, a stem, a leave, a branch, a flower, a fruit, or a seed), a tissue (such as a callus), or a cell.

In another preferred embodiment, the plant is selected from the group consisting of: Poaceae, Asteraceae, Liliaceae, Cruciferae, Rosaceae, Leguminosae, Theaceae, Sterculiaceae, Pinaceae, Juglandaceae, Piperaceae, Magnoliaceae, Ericaceae, Actinidiaceae, Vitaceae, Begoniaceae, Bromeliaceae, Ginkgoaceae, Illiciaceae, Zingiberaceae, Punicaceae, Apocynaceae, Berberidaceae, Rutaceae, Solanaceae, Cupressaceae, Aquifoliaceae, Palmae, and a combination thereof.

In another preferred embodiment, the plant is selected from the group consisting of *Arabidopsis*, tobacco, cotton, lettuce, rice, wheat, corn, peanut, sorghum, oats, rye, sugarcane, soybean, potato, buckwheat, pepper, grape, pear, apple, banana, *ginseng*, tomato, cayenne pepper, eggplant, cauliflower, chinese cabbage, oilseed rape, cucumber, watermelon, onion, sunflower, lily, rose, *chrysanthemum*, peony, carnation, camphor tree, Chinese parasol tree, pine tree, and a combination thereof.

In the third aspect of the present invention, an agricultural formulation is provided, which comprises:

(i) a compound represented by formula (I), or a salt, or an optical isomer, or a raceme, or a solvate, or a precursor thereof according to the first aspect of the present invention; and (ii) an agriculturally acceptable carrier.

In another preferred embodiment, in the agricultural formulation, the content of component (i) is 0.1-1000 µM, preferably 1-200 µM, more preferably 5-100 µM.

In another preferred embodiment, the agricultural formulation contains 0.0001-99 wt %, preferably 0.1-90 wt % of component (i), based on the total weight of the agricultural formulation.

In another preferred embodiment, the agricultural formulation further comprises an additional drought-resistant agent (such as a drought-resistant seed dressing agent, a drought-resistant moisture holding agent, or a drought-resistant spray agent) or other agricultural active ingredients.

In another preferred embodiment, the agricultural active ingredient is selected from the group consisting of: fungicides, herbicides, pesticides, nematicides, insecticides, plant activators, synergists, plant growth regulators, and acaricides.

In another preferred embodiment, the agricultural formulation further comprises a surfactant (such as a cationic surfactant, an anionic surfactant, an amphoteric surfactant, or a non-ionic surfactant).

In another preferred embodiment, the dosage form of the agricultural formulation is selected from the group consisting of: solutions, emulsions, suspensions, powders, foaming agents, pastes, granules, aerosols, and a combination thereof.

In the fourth aspect of the present invention, a method for enhancing the plant stress resistance is provided, by administering to a plant a compound of formula I, or a salt, or an optical isomer, or a racemate, or a solvate, or a precursor thereof according to the first aspect of the present invention or an agricultural formulation according to the third aspect of the present invention.

In another preferred example, the administering is selected from the group consisting of: spraying, irrigating.

In another preferred embodiment, the dosage for administering is 2-100 g/hectare, preferably 4-80 g/hectare, more preferably 6-60 g/hectare.

In another preferred embodiment, the dosage for administering is 1-5000 µg/plant, preferably 10-2500 µg/plant, more preferably 20-1000 µg/plant.

In the fifth aspect of the present invention, a method for preparing a compound of formula I or a salt thereof, comprising steps of:

(a) reacting a compound of formula Ia-6 with a compound of formula Ia-4 in an inert solvent, thereby forming a compound of formula I;

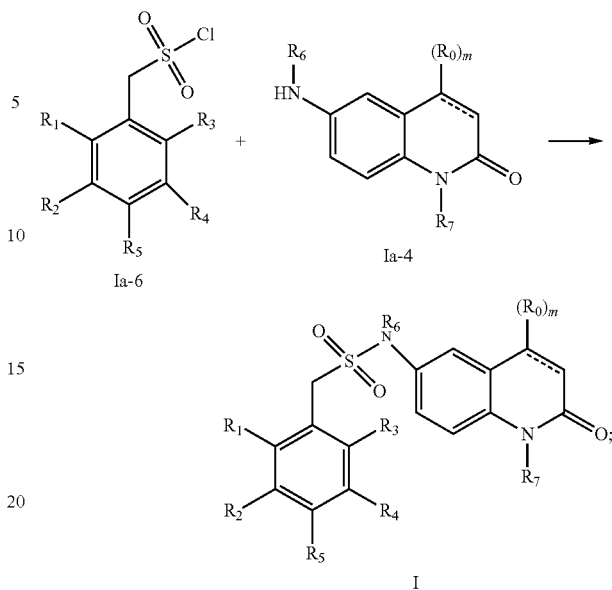

In each formula, $R_0$, $R_1$, $R_2$, $R_3$, $R_4$, $R_5$, $R_6$, $R_7$, m and '═══' are defined as above.

In another preferred embodiment, the reaction is carried out in the presence of an acid-binding agent.

In another preferred embodiment, the acid-binding agent is selected from the group consisting of: potassium carbonate, triethylamine, pyridine, and a combination thereof.

In another preferred embodiment, the inert solvent is selected from the group consisting of: DMF, DCM, acetonitrile, and a combination thereof.

In another preferred embodiment, the reaction temperature is 0-150° C. (or refluxing temperature), preferably 20-60° C., more preferably 25-40° C.

In another preferred embodiment, the reaction time is 0.1-72 hours, more preferably 1-24 hours, more preferably 2-20 hours.

In the sixth aspect of the present invention, a method for the preservative treatment of a plant is provided, comprising steps of:

contacting a plant to be preserved with a compound of formula I, or a salt, or an optical isomer, or a racemate, or a solvate, or a precursor thereof according to the first aspect of the present invention, thereby preserving the plant.

In another preferred embodiment, the plant includes a complete plant or a plant organ (such as a root, a stem, a leave, a branch, a flower, or a fruit).

In another preferred embodiment, the preservative treatment of a plant includes the preservative treatment of flower.

In the seventh aspect of the present invention, a method for the fruit coloring treatment is provided, comprising steps of:

contacting a fruit to be colored with a compound of formula I, or a salt, or an optical isomer, or a racemate, or a solvate, or a precursor thereof according to the first aspect of the present invention, thereby coloring the fruit.

In another preferred embodiment, the fruit comprises a grape.

In the eighth aspect of the present invention, a use of a compound of formula I, or a salt, or an optical isomer, or a racemate, or a solvate, or a precursor thereof according to the first aspect of the present invention is provided for the preparation of (i) an agonist of an ABA receptor; and/or (ii) a seed germination inhibitor.

In another preferred embodiment, the agonist promotes the interaction of the ABA receptor PYL protein with a PP2C protein phosphatase.

It should be understood that, within the scope of the present invention, each technical feature of the present invention described above and in the following (as examples) may be combined with each other to form a new or preferred technical solution, which is not listed here due to space limitations.

DESCRIPTION OF FIGURE

FIG. 7a shows that, compared with DMSO treatment, after treatment with 5 μM AMX compound and ABA, leaf temperature is significantly increased, wherein leaf transpiration was still significantly inhibited after four days of treatment with 0918 or 1127.

FIG. 7b shows that the inhibitory effect of AMX compounds on leaf transpiration is concentration-dependent, and the inhibitory effect at the same concentration is ranked as follows: 1127>0918>1125A.

FIG. 8a shows the plant growth status on day 1 and day 17 after the first spraying of the compound, and the concentration thereof in the experiment is 10 μM; FIG. 8b shows the plant growth status on day 1, 18 and 20 after the first spraying of the compound, and the concentration thereof in the experiment is 5 μM; FIG. 8c shows the plant growth status on day 1 and day 14 after the first spraying of the compound, and the concentration thereof in the experiment is 10 μM.

DETAILED DESCRIPTION

Figure 1:
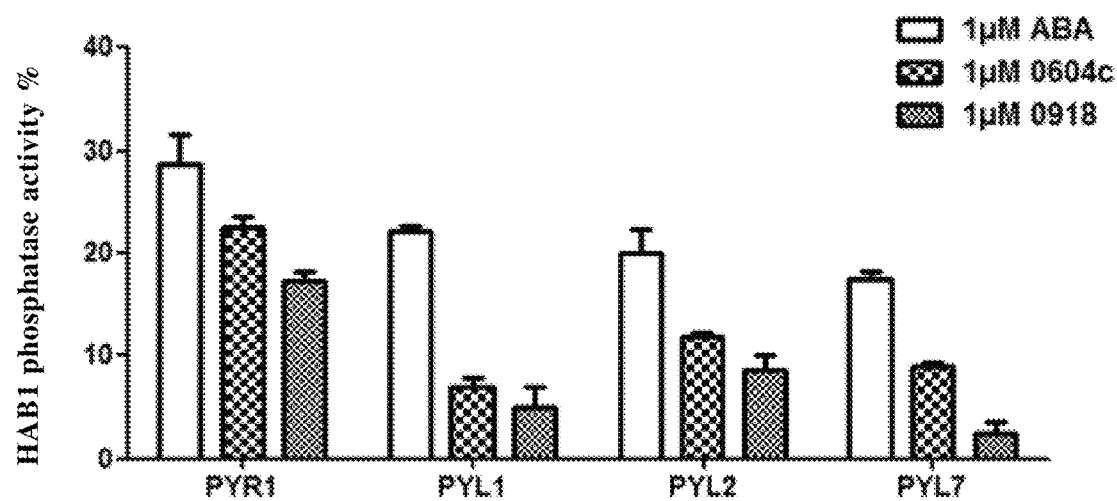
FIG. 1 shows that two AMX compounds 0604c and 0918 of the present invention can bind to a complex of *Arabidopsis* PYR/PYL receptors (PYR1, PYL1, PYL2 and PYL7) and HAB1, thereby inhibiting activity of protein phosphatase HAB1. At the concentration of 1 μM, the inhibitory effects of these compounds are significantly better than that of ABA.

After a long and intensive study, the present inventors have firstly developed a class of ABA substitutions (the compounds of the present invention) with high abscisic acid (ABA) activities. The compounds of the present invention have a significantly higher activity compared with the existing ABA analogues and can significantly enhance the multi-resistance of the plant (such as drought resistance, cold tolerance, etc.). In addition, the compounds of the present invention are easy to be prepared, and have the advantages such as excellent environmental friendliness and a rapid action and so on, and therefore they have a broad application prospect. On this basis, the inventors complete the present invention.

Experiments have shown that the compounds of the present invention (abbreviated as AMX compounds) not only have a better activity than Abscisic Acid (ABA) and the existing ABA analogs, such as 4-methyl-N-(1,2,3,4-tetrahydro-2-carbonyl-1-propyl-6-quinolinyl)-benzene methanesulfonamide (4-methyl-N-(1,2,3,4-tetrahydro-2-oxo-1-propyl-6-quinolinyl)-benzene methanesulfonamide), but also can bind to a number of different PYL receptors, and can significantly increase the stress resistance of a variety of different plants.

Group Definition

As used herein, the term "$C_1$-$C_7$ alkyl" refers to a straight or branched alkyl group having 1 to 7 carbon atoms, such as methyl, ethyl, propyl, isopropyl, butyl, isobutyl, sec-butyl, t-butyl, or the like.

As used herein, the term "$C_2$-$C_7$ alkenyl" refers to a straight or branched alkenyl group having 2 to 7 carbon atoms, such as ethenyl, allyl, 1-propenyl, isopropenyl, 1-butenyl, 2-butenyl, or the like.

As used herein, the term "$C_2$-$C_7$ alkynyl" refers to a straight or branched alkynyl group having 2 to 7 carbon atoms, such as ethynyl, propynyl, or the like.

As used herein, the term "$C_1$-$C_3$ alkyl" refers to a straight or branched alkyl having 1 to 3 carbon atoms, such as methyl, ethyl, n-propyl, isopropyl, or the like.

As used herein, the term "$C_1$-$C_3$ haloalkyl" refers to a straight or branched alkyl group having 1 to 3 carbon atoms in which one or more hydrogen is replaced by halogen, for example, halomethyl, haloethyl, halopropyl, haloisopropyl, or the like.

As used herein, the term "$C_3$-$C_7$ cycloalkyl" refers to a cyclic alkyl having 3 to 7 carbon atoms, such as cyclopropyl, cyclobutyl, cyclopentyl, cyclohexyl, cycloheptyl, or the like.

As used herein, the term "halogen" refers to fluorine, chlorine, bromine, or iodine, preferably fluorine or chlorine.

As used herein, the term "halogenated" refers to a group that is substituted with one or more of the same or different halogen atoms described as above, which may be partially halogenated or perhalogenated, such as trifluoromethyl, pentafluoroethyl, heptafluoroisopropyl, or the like.

The compounds of the present invention may contain one or more asymmetric centers and therefore occur as racemates, racemic mixtures, single enantiomers, diastereomeric compounds, and single diastereomers. The asymmetric center that can exist depends on the nature of the various substituents on the molecule. Each such asymmetric center will independently produce two optical isomers, and all possible optical isomers and diastereomeric mixtures and pure or partially pure compounds are included within the scope of this invention. The invention includes all isomeric forms of the compounds.

Compounds of Formula I and the Preparation Method Thereof

As used herein, the terms "compounds of the present invention", "AMX compound", "compound AMX", "ABA substitutes of the present invention", and "compound of formula I" can be used interchangeably, all of which refer to compounds having the structure shown in Formula I. In addition, the terms also include salts, optical isomers, racemates, solvates (such as hydrates), and/or precursors of the compounds of formula I,

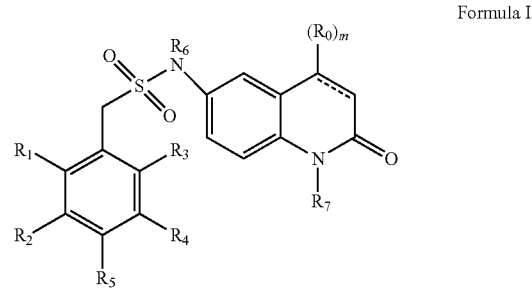

Formula I wherein $R_0$, $R_1$, $R_2$, $R_3$, $R_4$, $R_5$, $R_6$, $R_7$, m, and "=====" are defined as above.

The preparation method of the compounds of formula I according to the present invention is described more specifically as below, but which are not intended to limit the invention in any way. The compounds of the present invention may also be conveniently prepared by a combination of various synthesis methods described in the presenting specification or known in the art, and such combinations are readily available to those skilled in the art. In general, in the preparation method of the present invention, most of the reactions are performed in an inert solvent at a temperature of 0° C. to 150° C. (or refluxing temperature) (preferably, 20-60° C., or 25-40° C.) for a period of time (such as, 0.1-72 hours, preferably 2-20 hours).

Preferably, the compounds of formula I according to the present invention can be prepared by the following schemes, the exemplary methods described in examples and the relevant published literature used by those skilled in the art.

Typically, the preparation method of the compounds of Formula Ia and/or Formula Ib of the present invention can include, but is not limited to, the following schemes.

Scheme I (Taking $R_6$=H and $R_7$=Propyl as an Example)

(1) Preparation of 6-amino-1-propyl-quinolinone

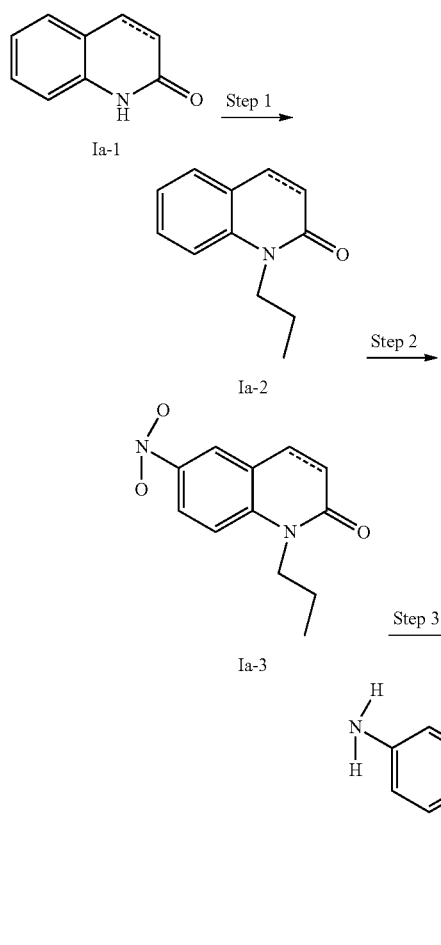

Step 1: In the presence of an alkali (such as potassium carbonate, sodium hydride), in an inert solvent (such as DMF), firstly, reacting the compound of formula Ia-1 with a haloalkane at a temperature (such as 25-40° C.) for a period of time, thereby forming a compound of formula Ia-2.

Step 2: In the presence of an acid (such as sulfuric acid), reacting the compound of formula Ia-2 with potassium nitrate at a temperature (such as 0-20° C.) for a period of time, thereby forming a compound of formula Ia-3.

Step 3: In an inert solvent (such as methanol), the compound of formula Ia-3 is subjected to a reduction reaction with palladium on carbon as a catalyst at a temperature (such as 10-40° C.), thereby forming a compound of formula Ia-4.

(2) Preparation of p-methylhalobenzylsulfonyl chloride

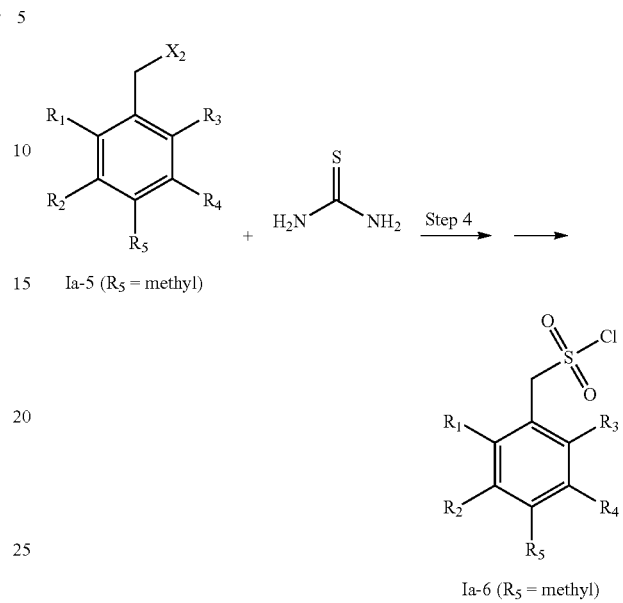

Step 4: In an inert solvent (such as ethanol, acetonitrile), reacting a compound of formula Ia-5 (such as p-methylbenzyl bromide or p-methylbenzyl chloride) with thiourea, thereby forming a reaction product. Then in the presence of an acid (such as concentrated hydrochloric acid), in an inert solvent (such as acetonitrile), reacting the reaction product with sodium chlorite at a temperature (such as 0-20° C.) for a period of time, thereby forming a compound of Formula Ia-6.

(3) Preparation of a Compound of Formula Ia/Ib

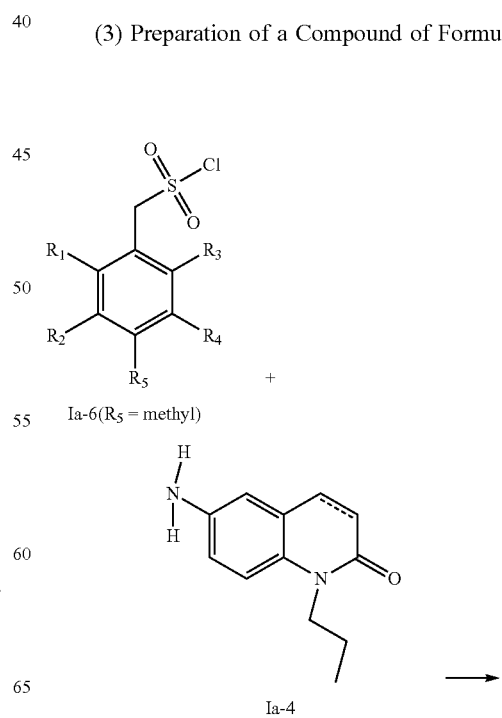

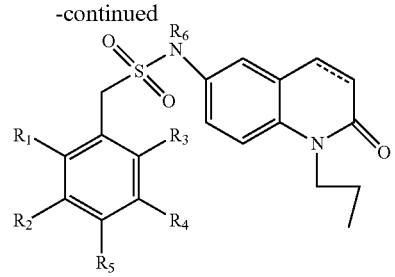

Ia/Ib ($R_6$ = H, and $R_5$ = methyl)

Step 5: In an inert solvent (such as DMF), in the presence of an acid-binding agent (such as potassium carbonate), reacting the compound of formula Ia-6 with the compound of formula Ia-4 at a temperature (for example, 25-40° C.) for a period of time, thereby giving a compound of formula Ia/Ib.

In scheme I, $X_2$ is a leaving group, which is chlorine, bromine or iodine. Other substituents and groups are as defined in the specification. '═══' represents a single bond or a double bond.

The preparation method of a compound of formula Ic of the present invention may include (but is not limited to) the following scheme:

Scheme II (Taking m=1, $R_6$ is H, $R_7$=Propyl and $R_0$ is Methyl as an Example)

(1) Preparation of 6-amino-4-methyl-1-propyl-2 (1H)-quinolinone

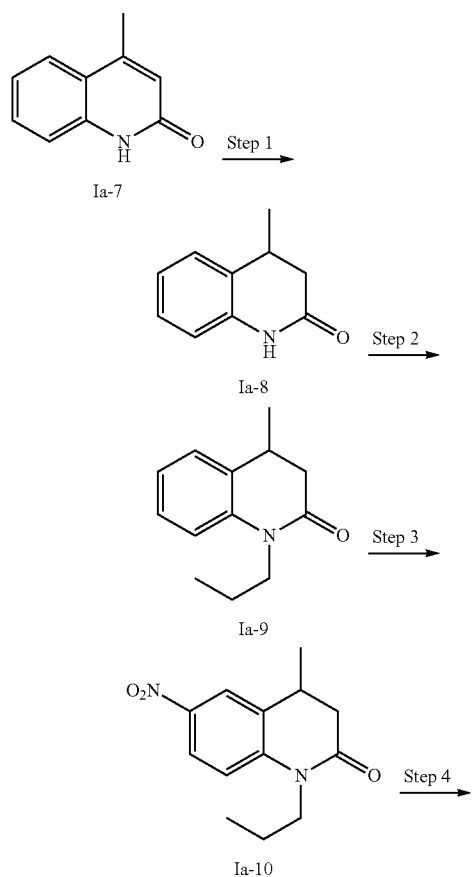

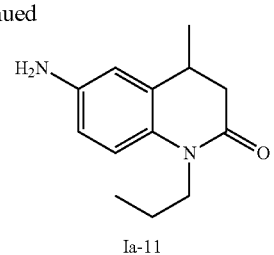

Ia-11

Step 1: In the presence of a catalyst (such as palladium on carbon, platinum dioxide), in an inert solvent (such as acetic acid, ethyl acetate), Ia-7 is hydrogenated at a temperature (e.g., 50-80° C.) for a period of time, thereby forming a compound of formula Ia-8.

Step 2: In the presence of an alkali (such as potassium carbonate, sodium hydride), in an inert solvent (such as DMF), firstly reacting the compound of formula Ia-8 with a haloalkane at a temperature (such as 25-40° C.) for a period of time, thereby forming a compound of formula Ia-9.

Step 3: In the presence of an acid (such as sulfuric acid), reacting the compound of formula Ia-9 with potassium nitrate at a temperature (for example 0-20° C.) for a period of time, thereby forming a compound of formula Ia-10.

Step 4: The compound of formula Ia-10 is subjected to a reduction reaction in an inert solvent (such as methanol) at a temperature (e.g., 10-40° C.) using palladium on carbon as a catalyst, thereby forming a compound of formula Ia-11.

(2) Preparation of p-methylhalobenzylsulfonyl Chloride

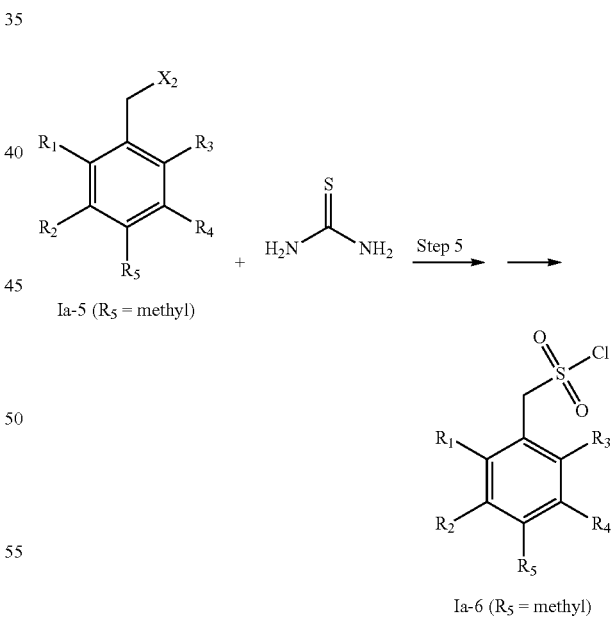

Step 5: In an inert solvent (such as ethanol, acetonitrile), reacting a compound of formula Ia-5 (such as p-methylbenzyl bromide or p-methylbenzyl chloride) with thiourea, thereby forming a reaction product. Then in the presence of an acid (such as concentrated hydrochloric acid), in an inert solvent (such as acetonitrile), reacting the reaction product with sodium chlorite at a temperature (such as 0-20° C.) for a period of time, thereby forming a compound of formula Ia-6.

(3) Preparation of a Compound of Formula Ic

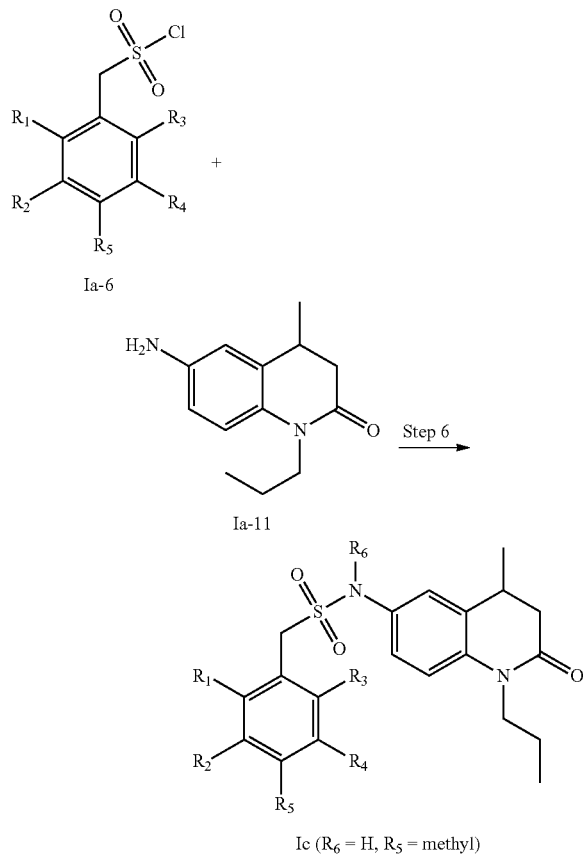

Step 6: In an inert solvent (such as DMF), in the presence of an acid-binding agent (such as potassium carbonate), reacting a compound of formula Ia-6 with a compound of formula Ia-11 at a temperature (such as 25-40° C.) for a period of time, thereby giving a compound of formula Ic.

In Scheme II, $X_2$ is a leaving group, which is chlorine, bromine, or iodine. Other substituents and groups are as defined in the specification.

Agricultural Formulations

The active substances (compounds of formula I, or salts thereof, or optical isomers thereof, or racemates thereof, or solvates thereof, or precursors thereof) of the present invention may be prepared into agricultural formulations in conventional manners, for example, solutions, emulsions, suspensions, dusts, foaming agents, pastes, granules, aerosols, natural and synthetic materials impregnated with active substances, microcapsules in polymers, coating materials for seeds.

These formulations can be produced by known methods, for example, by mixing the active compounds with extenders which are liquid or liquefied or solid diluents or carriers and optionally with surfactants, that is, emulsifiers and/or dispersants and/or foam formers. For example, when water is used as an extender, organic solvents can also be used as auxiliaries.

It is basically suitable when using a liquid solvent as a diluent or a carrier, for example, aromatic hydrocarbons such as xylene, toluene or alkyl naphthalene; chlorinated aromatic or chlorinated aliphatic hydrocarbons such as chlorobenzene, vinyl chloride or methylene chloride; aliphatic hydrocarbons such as cyclohexane, or paraffins such as mineral oil fractions; alcohols and their ethers and esters such as ethanol or ethylene glycol; ketones such as acetone, methyl ethyl ketone, methyl isobutyl ketone or cyclohexanone; or less commonly used polar solvents such as dimethylformamide and dimethyl sulfoxide, and water.

In the case of liquefied diluents or carriers, they refer to a liquid that will become a gas at an atmospheric temperature and an atmospheric pressure, such as an aerosol propellant such as halogenated hydrocarbons as well as butane, propane, nitrogen and carbon dioxide.

The solid carrier may be ground natural minerals such as kaolin, clay, talc, quartz, activated clay, montmorillonite, or diatomaceous earth, as well as ground synthetic minerals such as highly dispersed silicic acid, alumina and silicates. Solid carriers for granules are ground and fractionated natural zircons such as calcite, marble, pumice, sepiolite and dolomite, as well as synthesized granules by inorganic and organic coarse powder, and organic materials such as particles of sawdust, coconut shell, corn cobs, tobacco stems and so on.

Nonionic and anionic emulsifiers can be used as emulsifiers and/or foam formers. For example, polyoxyethylene-fatty acid esters, polyoxyethylene-fatty alcohol ethers, for example alkylaryl polyglycol ethers, alkyl sulfonates, alkyl sulfates, arylsulfonates and albumin hydrolysate. Dispersants include, for example, lignin sulfite waste liquors and methylcellulose.

Binders, such as carboxymethylcellulose and natural and synthetic polymers in the form of powders, granules or emulsions, may be used in the formulation, such as acacia, polyvinyl alcohol and polyvinyl acetate.

Colorant may be used, for example inorganic dyes such as iron oxide, cobalt oxide and Prussian Blue; organic dyes such as organic dyes of azo dyes or metal titanium cyanine dyes; and trace nutrients such as salts of iron, manganese, boron, copper, cobalt, aluminum and zinc and the like.

In the present invention, the "agricultural formulation" is generally an agricultural plant growth regulator, which comprises a compound of formula I or a salt, an optical isomer, a racemate, a solvate or a precursor thereof as an active ingredient for enhancing the plant stress resistance (such as drought resistance); and an agriculturally acceptable carrier.

As used herein, the "agriculturally acceptable carrier" is an agriculturally acceptable solvent, suspension, or excipient which is used to deliver the compounds of formula I or salts, optical isomers, racemates, solvates, or precursors thereof of the present invention to a plant. The carrier can be liquid or solid. An agriculturally acceptable carrier suitable for use in the present invention is selected from the group consisting of: water, buffers, DMSO, surfactants such as Tween-20, and a combination thereof. Any agriculturally acceptable carrier known to those skilled in the art may be used in the present invention.

The agricultural formulations of the present invention may be formulated with other drought-resistant agents into a mixture to be present in their product formulations or in the dosage forms prepared from these formulations, such other drought-resistant agents include (but are not limited to) drought-resistant seed dressing agents, drought-resistant moisture holding agents, or drought-resistant spray agents.

In addition, the agricultural formulations of the present invention may also be formulated with synergists into a mixture to be present in their product formulations or in the dosage forms prepared from these formulations, and these synergists are compounds which enhance the action of the active compound. Since the active compound itself is active, the synergists may not be added.

The dosage forms of the agricultural formulations of the present invention can be varied, and all of those which can allow the effective delivery of the active ingredient into the plant in vivo can be used. From the standpoint of easy for preparation and administration, the preferred agricultural formulation is a spray or a solution.

The agricultural formulations of the present invention usually contain from 0.0001 to 99 wt %, preferably from 0.1 to 90 wt %, of the compounds of the present invention, based on the total weight of the agricultural formulation. The concentration of the compounds of the present invention in commercial formulations or used dosage forms can be widely varied. The concentration of the compounds of the present invention in commercial formulations or used dosage forms may range from 0.0000001-100% (g/v), preferably between 0.0001 and 1% (g/v).

Method for Enhancing the Plant Stress Resistance

The present invention provides a method for enhancing the plant stress resistance, such as drought resistance, comprising steps of: administering to a plant a compound of formula I or a salt, an optical isomer, a racemate, a solvate or a precursor thereof, or a corresponding agricultural formulation thereof.

Administration can be carried out by various methods which are already known, for example, by spraying, atomizing, dusting or broadcast sowing the compound or the agricultural formulation containing the compound on plant leaves, propagation material, or by other manners to contact the plant with the compound or the agricultural formulation containing the compound, if to contact seeds, they are treated by coating, wrapping or other ways. Another method of treating plants or seeds directly before planting is to introduce the agricultural formulation of the present invention into the soil or other medium to be sown. In some embodiments, a carrier can also be used, which may be in a solid, liquid state as described above.

In a preferred embodiment, the compound or the agricultural formulation containing the compound may also be delivered to the plant by spraying (such as aircraft spraying) or irrigating.

Other Applications

The compounds of the present invention can be used as a plant preservative, and the plant includes, but is not limited to: a flower, a horticultural plant and the like, there is a very significant preservation effect especially for flowers, such as gerbera.

The compounds of the present invention can also be used as a fruit coloring agent, and the fruit includes, but is not limited to, a grape.

The main advantages of the present invention include:

For the first time, a class of ABA substitution (compounds of the present invention) with a high abscisic acid (ABA) activity has been developed. The compounds of the present invention have a significantly higher activity than the existing ABA analogues and can significantly enhance a variety of stress resistances (such as drought resistance, cold tolerance, etc.) of the plant. In addition, the compounds of the present invention are easy for preparations, and have an excellent environmental friendliness, and therefore have a broad application prospect. On this basis, the present invention has been completed.

Experiments have shown that the compounds of the present invention (abbreviated as AMX compounds) are not only more active than Abscisic Acid (ABA) and the existing ABA analogs, such as 4-methyl-N-(1,2,3,4-tetrahydro-2-carbonyl-1-propyl-6-quinolinyl)-benzene methanesulfonamide (4-methyl-N-(1,2,3,4-tetrahydro-2-oxo-1-propyl-6-quinolinyl)-benzene methanesulfonamide) but also can bind to a number of different PYL receptors, and can significantly increase the stress resistance of a variety of different plants.

(1) For the first time, the present invention has synthesized highly active alternatives of natural abscisic acid (ABA), AMX compounds. The AMX compounds of the present invention can significantly enhance a variety of stress resistances in plants (such as drought resistance and cold tolerance). Also, the optical isomers or racemates of the present compounds have a high activity.

(2) The activity of the AMX compounds of the present invention is significantly superior to abscisic acid (ABA) and the existing ABA analogs.

(3) The AMX compounds of the present invention can promote the interaction between a plurality of PYR/PYL receptor proteins and PP2C protein phosphatase HAB1, and the promotion effect on PYR1, PYL1, PYL2 and PYL7 is particularly remarkable.

(4) The compounds of the present invention are more easily absorbed by plants and have a quick action.

(5) The compounds of the present invention are environmentally friendly and not harmful to mammals.

(6) The synthesis methods of the compounds of the present invention are simple and cost low.

The present invention is further described below with reference to specific embodiments. It should be understood that these examples are only for illustrating the present invention and not intended to limit the scope of the present invention. The conditions of the experimental methods not specifically indicated in the following examples are usually in accordance with conventional conditions as described in Sambrook et al., Molecular Cloning: A Laboratory Manual (New York: Cold Spring Harbor Laboratory Press, 1989), or according to the conditions described in the Journal of Microbiology: An Experimental Handbook (edited by James Cappuccino and Natalie Sherman, Pearson Education Press) or the manufacturer's proposed conditions. Unless otherwise indicated, percentages and parts are by weight and parts by weight.

Materials and General Methods

Materials

The model plants used in the experiments are all conventional or commercial available varieties, wherein *Arabidopsis thaliana* includes: Colombia (Col-0) ecotype and Col-0 ecotype-based ABA synthesis mutants aba2-1 and triple mutant pyr1;pyl1;pyl4 of ABA receptor PYL. Soybean varieties include Williams 82, cotton varieties include upland cotton R15, and corn varieties include Danyu 402.

Compound AM1: an existing ABA analogue whose chemical name is (4-methyl-N-(1,2,3,4-tetrahydro-2-oxo-1-propyl-6-quinolinyl)-benzene methanesulfonamide).

AMX compounds: The compounds of the present invention (such as, 0604c, etc.). See Examples 1-17.

Plant Growth

The growth temperature for *Arabidopsis thaliana* is 22° C. The photoperiod of plants (such as in seed germination experiments and gene expression analysis) grown in a plant growth media is long-day (24-hour light), and the photoperiod of plants grown in soil (such as, in leaf transpiration experiments and soil drought experiments) is short day (8-hour light/16-hour darkness), and the light intensity is 75 $\mu mol \cdot m^{-2} \cdot s^{-1}$.

The growth temperature for soybean is 26° C. and the photoperiod is 16-hour light/8-hour darkness. The growth temperature for corn is 27° C., and the photoperiod is 11-hour light/13-hour darkness. The growth temperature for cotton is 26° C., and the photoperiod is 14-hour light/10-hour darkness. The light intensity is 400 μmol·m$^{-2}$·s$^{-1}$.

Unless stated otherwise, all of the plant growth media used in the experiments are ½ MS (Murashige and Skoog) solid media containing 1% (w/v) of sucrose and 0.6% (w/v) of agar.

Protein Expression and Purification

The construction method of recombinant plasmids for the *Arabidopsis thaliana* genes PYL1 (amino acid sequence 36-211), PYL2 (amino acid sequence 14-188) with dual tags of 6×His and SUMO sequence and the *Arabidopsis thaliana* gene HAB1 (amino acid sequence 172-511) with the Biotin tag sequence is described in detail in "A gate-latch-lock mechanism for hormone signaling by abscisic acid receptors" (Nature, Vol 462, 2009). The construction method of recombinant plasmids for other *Arabidopsis thaliana* PYL genes with dual tags of 6×His and SUMO sequence, including PYR1, PYR3, PYL4, PYL5, PYL6, PYL7, PYL8, PYL9 and PYL10 (all of the above 9 genes are whole genome coding sequences) and the soybean PYL genes (including GmPYL3 and GmPYL6) is the same as that for PYL1/PYL2.

The above recombinant plasmid is transformed into competent cell of *E. coli* BL21 (DE3), and inoculated into 200 ml of LB liquid medium containing Ampicillin and cultured overnight at 37° C. at 200 rpm; and inoculated into 2 L of LB liquid medium containing Ampicillin at a ratio of 1:50-1:100 for an extended culture, and cultured at 37° C., 200 rpm for 3-4 hours, and at a low temperature of 16° C. until OD$_{600}$ is about 0.8-1.0. Recombinant plasmids for PYR1/PYL1/PYL2/PYL7 with dual tag of 6×His and SUMO sequence were induced overnight with 100 μM of IPTG while HAB1 recombinant plasmid with the Biotin tag sequence was induced simultaneously with 100 μM of IPTG and 40 μM of biotin.

After 16 hours of induction, the bacterial solution was centrifuged at 4000 rpm for 20 minutes at 4° C. in a low-speed high-capacity centrifuge, and the bacteria cells were collected. Bacteria cells were resuspended in 50 ml of extraction buffer (containing 20 mM Tris, pH 8.0, 200 mM NaCl and 10% (v/v) glycerol) per 2 of bacterial solution and then subjected to pressure-breaking at 1000 Pa and 4° C. for 3-5 times. The broken cells were subjected to ultracentrifugation, centrifuged at 16000 rpm for 30 minutes, and this process was repeated twice. The supernatant was collected and subjected to an affinity chromatography column.

For PYR/PYL proteins with 6×His and SUMO dual tag sequences, 50 ml of affinity chromatography Ni column (50 ml Ni-NTA column, available from GE) was used. Firstly, The column was equilibrated with 600 ml of 10% buffer B (containing 20 mM Tris, PH 8.0, 200 mM NaCl, 500 mM imidazole and 10% glycerol), and then eluted with 200 ml of 50% buffer B and finally eluted with 100 ml of 100% buffer B. Proteins for crystal analysis were mixed with ulp1 enzyme at a molar ratio of 1000:1, and digestion dialysis was conducted overnight. The digested proteins were subjected to affinity chromatography on a Ni column once more. The collected solution was subjected to a HiLoad 26/60 Superdex200 gel filtration column (commercially available from GE) and eluted with an elution solution (containing 25 mM Tris, pH 8.0, 200 mM ammonium acetate, 1 mM dithiotreitol and 1 mM EDTA) to further separate and purify the protein.

For a HAB1 protein with a Biotin tag sequence, it was subjected to a 50 ml MBP affinity column (available from GE). The column was firstly equilibrated with 600 ml of 10% buffer C (containing 20 mM Tris, pH 8.0, 200 mM NaCl, 10 mM Maltose and 10% Glycerol) and eluted with 200 ml of 50% buffer C and finally eluted with 100 ml of 100% buffer C. The collection solution was subjected to a HiLoad 26/60 Superdex200 gel filtration column and eluted with an elution solution (containing 20 mM Tris, pH 8.0, 200 mM NaCl and 10% Glycerol) to further separate and purify the protein.

Protein Crystal Analysis

Prior to crystallization, the digested PYL2 and HAB1 proteins were mixed with the compounds at a molar ratio of 1:1:5 and concentrated to 6 mg/ml for crystal formation. Crystal formation was carried out by the dropwise method. The well buffer for crystallization contained 0.1 M Succinic acid and 15% PEG3350, or 0.2 M Di-sodium malonate and 20% PEG 3350, or 0.2 M Tri-sodium Citrate and 20% PEG 3350, or 0.2 M Magnesium formate and 20% PEG 3350. After one day, the crystals could be seen, which grew to 100-120 m for about 3-4 days. Crystals were analyzed by X-ray diffraction and the diffraction data were collected, and the structure of the complex was analyzed according to the relevant PYR/PYL receptor structure model.

AlphaScreen Experiment

The AlphaScreen kit (available from Perkin Elmer) was used, and the method was as follows: 150 μl of experimental system contained a 10× buffer (50 mM MOPS, pH 7.4, 50 mM NaF, 50 mM CHAPS, 0.1 mg/ml bovine serum albumin) diluted at 1:10, 100 nM HAB1 with Biotin tag sequence or PYR1/PYL1/PYL2/PYL7/GmPYL3/GmPYL6 protein with 6×His and SUMO dual tag sequences, corresponding concentrations of (+)-ABA/AM1/AMX, and 5 μg/ml donor beads and acceptor beads (available from Perkin Elmer). After incubating for 1.5 hours at room temperature in the dark, it was placed into an Envision Plate Reader (available from Perkin Elmer) under the programmed AlphaScreen procedure for readings.

HAB1 Phosphatase Activity Assay

The reaction system contained 50 mM imidazole, pH 7.2, 5 mM MgCl$_2$, 0.1% β-mercaptoethanol, 0.5 μg·ml$^{-1}$ BSA, 100 nM HAB1 protein with a Biotin tag sequence, 500 nM PYL with 6×His-SUMO dual tag sequence and the corresponding concentration of (+)-ABA/AM1/AMX. The reaction system was incubated at room temperature for 30 minutes, followed by a further reaction for 30 minutes after adding an 11-amono acid phosphorylated polypeptide as a substrate. The phosphorylated polypeptide consisting of amino acid 170-180 of SnRK2.6 protein kinase (sequence HSQPKpSTVGPT) was purchased from Kingsley company, wherein phosphorylated serine at position 175 was a known HAB1 dephosphorylation target site. After 30 minutes, chromogenic reagent (purchased from BioVision) was added and the absorbance at 650 nm was read on a microplate reader (Molecular Devices).

Gene Expression Analysis

The whole plant or leaves were taken, and RNA extraction was carried out by using conventional methods. After reverse transcription, the fluorescence quantitative PCR was carried out. Triple biological samples were taken for each treatment which was performed twice. The ACT7 gene was used as a reference gene.

Seed Germination and Soil Drought Experiments (1) Seed Germination

The seeds of *Arabidopsis thaliana* Col-0 ecotype and PYL receptor triple mutant (pyr1;pyl1;pyl4) were sterilized with NaClO and placed at 4° C. for 3 days of the vernalization, and then sown in ½ MS solid medium containing 1 μM different AMX compounds including (+)-ABA, AM1, 0604c, 0918, 1127 or 0.05% DMSO (control). Two lines of plant were sown simultaneously on a single medium of 6 cm diameter, with 15 seeds sown for each line and 4 replicates for each compound. Culture medium was placed at 22° C. for long-day culture, and the photos were taken after 5 days.

(2) Plant Leaf Transpiration Experiment

ABA synthesis defective mutant aba2-1 was used in *Arabidopsis* leaf transpiration experiment. Under condition of environmental stress, the content of endogenous ABA in this mutant does not increase, and is only ¼₀ of that in wild-type *Arabidopsis* Col-0 under the same condition. Therefore, this mutant is used to exclude effect of endogenous ABA in the transpiration experiment. After three weeks of continuous watering, 0.05% tween-20 and corresponding concentrations of DMSO (control)/compound (+)-ABA/0918/1127 were sprayed onto the plants in a single administration with an amount of 1.2 ml/pot. Images were taken daily using the FLIR A655sc thermal imaging camera at the same time before and after spraying. The Williams 82 ecotype was used in soybean leaf transpiration experiments for compounds 0604c, 0918 and 1127 and was long-day cultured at 26° C. After the plants grew and had 3 leaves in each of 3 groups, 0.05% tween-20 and 50 µM DMSO (control)/(+)-ABA/0604c/0918/1127 compounds were sprayed in a single administration with an amount of 4 ml/pot. Images were taken daily using the FLIR A655sc thermal imaging camera at the same time before and after spraying.

Leaf transpiration experiments of soybean and cotton for compound 0720B were carried out at 26° C. with long-day lighting. 16 days and 23 days after sowing, a solution containing 0.1% tween-20 and corresponding concentration of (+)-ABA, or 0720B compound or 0.1% Tween-20 and 0.05% DMSO (control) was sprayed in an amount of 4 ml/pot. Images were taken daily using the FLIR A655sc thermal imaging camera at the same time before and after spraying.

(3) Soil Drought Experiment

Seeds of *Arabidopsis* Col-0 ecotype were sterilized with NaClO and then sown on ½ MS solid medium at 4° C. for 3 days of vernalization. After 6 days of growing, the well-grown seedlings having uniform size were selected and transferred into 8×7×6 cm³ pots. Each pot was filled with the same weight of soil and the same number of plants (six plants) was planted to reduce experimental error. All the pots were subjected to a short-day culture at 22° C. After two weeks, watering was stopped for drought treatment. A solution containing 0.02% tween-20 and corresponding concentrations of (+)-ABA, AM1, 0604c, 0918 or 1127 or 0.02% tween-20 and 0.05% DMSO (control) was sprayed onto the leaf surface once each week with a spray amount of 2 ml solution/pot. The position of the flowerpot was changed every day during the process of drought to reduce the error caused by environmental factors. During the whole drought period, the solution was sprayed twice in total and photos were recorded regularly. The watering was resumed in about three weeks.

Soil drought experiments on soybean and maize used for compounds 0918 and 1127 were similar to that on *Arabidopsis thaliana*. Only one plant was contained in each pot. All soybean plants were long-day cultured at 26° C. Watering was stopped after the plant had three leaves in each of three groups of leaves and the plants with consistent growth were selected for drought treatment. As for corn, watering was stopped during the small trumpet period for drought treatment. A solution containing 0.05% tween-20 and 50 µM (+)-ABA, 0918, 1127 or 0.05% tween-20 and 0.05% DMSO (control) was sprayed once on leaf surface every three days during drought treatment with a spray amount of 4 ml/pot, while the pot position was also changed. After a week, the watering was resumed.

Soybeans and cotton used in leaf transpiration experiments for compound 0720B were also used for soil drought experiments. Each pot contained only one plant and was filled with the same weight of soil to reduce experimental errors. All of the soybean plants were grown at 26° C. for long-day culture. 16 days after seeding, watering was stopped and the plants with consistent growth were selected for drought treatment. At the beginning of drought, a solution containing 0.1% Tween-20 and corresponding concentrations of (+)-ABA, or 0720B or 0.1% Tween-20 and 0.05% DMSO (control) was sprayed onto the leaf surface once, and then sprayed once every 3 days with a spray amount of 4 ml/pot, while the pot position was changed. 11 days after drought, re-watering treatment was carried out and photos were taken one day after re-watering. Cotton drought experiments were similar to that of the soybean. 23 days after seeding, the watering was stopped, and the plants with consistent growth were selected for drought treatment. At the beginning of drought, a solution containing 0.1% Tween-20 and 50 µM (+)-ABA, or 0720B or 0.1% Tween-20 and 0.05% DMSO (control) was sprayed onto the leaf surface once, and then sprayed once every 4 days with a spray amount of 4 ml/pot, meanwhile the pot position was changed. After 10 days of drought, the photos were taken.

Flower Preservative Experiment

The commercially available Yunnan Lily varieties "Siberia" biennial buds were used for test, wherein each branch had 5 buds and 10 leaves, and there was 1 branch per bottle. The branch having buds was inserted into a water suspension preparation containing 10 ppm (22.5 µM) of AMX compound 1127 or into tap water. The flower status was recorded before and after 20 days of treatment.

Grape Coloring Experiment

The grapes used in the experiment were commercially available variety of Kyoho. According to weather conditions, during the color conversion period of grapes, the fruit ears with the same size and consistent growth were selected and soaked with a water suspension preparation containing 2000 mg/L, 1000 mg/L, 500 mg/L and 100 mg/L of 6% AMX compound 1127 for 10 seconds. Soaking in water was regarded as a control. Each experiment was repeated 10 times, each ear was regarded as a duplicate. Samples were collected after harvesting. Samples were collected from the upper, middle and lower parts of each ear in two directions, i.e., glossy and backlit, with 6 grains collected per ear. The samples were preserved in the laboratory at −20° C. for use.

30 pieces of pericarp were evenly taken from up and low portion around the equator of grape fruit by using a hole puncher with a diameter of 10 mm. After they were mixed well and weighed, the anthocyanin in the pericarp was determined. The pericarp was added into 5 ml of methanol solution containing 1% of formic acid, and extracted at 25° C. in the dark on a shaker for 30 mins. Then it was centrifuged at low temperature and at 8000×g for 10 mins. The supernatant was collected and the residue was extracted four times repeatedly. The supernatant was combined. Formic acid and methanol were removed by rotary evaporation at 30° C. and re-dissolution was conducted by using an aqueous solution of formic acid ethanol (formic acid:ethanol:water=2:10:88) and the volume was set to 5 ml. The content of anthocyanins (calculated as cornflower-3-glucoside equivalent) was determined by pH differential method and each treatment was repeated three times. Content of anthocyanins (mg/g) X=ΔA×F×M/ε×m, wherein ΔA was absorbance; F was fold of dilution; M is the relative molecular mass 449.2 of cyanidin-3-glucoside, ε is a molar extinction coefficient 26,900 for cyanidin-3-glucoside; m is sample mass.

AMX Toxicology Experiment

AMX toxicology experiments included: 1) a bacterial reverse mutation experiment, which was used to test whether the test substance had an effect of inducing mutation, and 2) in vitro micronucleus experiment, which was used to test whether the test substance had an effect of inducing an increased micronucleus rate in Chinese hamster lung cell (CHL) under a non-metabolic activation system condition (−S9); and 3) a maximum tolerated dose of tested substance in single oral gavage experiment in SD rat, which was used for preliminary assessment of toxic effect on a target organ and the possible toxic mechanism. The test substance used in the experiment was AMX compound 1127.

Two strains of Salmonella typhimurium, TA98 and TA100, were used in the bacterial reverse mutation experiment. The experiment was carried out by using standard plate incorporation method under a condition of non-metabolic activation system (−S9). There were totally 7 doses of 5 g/dish, 15 g/dish, 50 g/dish, 150 g/dish, 500 g/dish, 1500 g/dish and 5000 g/dish as well as a negative control and a positive control.

Firstly, CHL cells used in in vitro micronucleus test were tested in $IC_{50}$ determination experiment. According to $IC_{50}$ determination results, in vitro micronucleus test dosage was set. 4 doses of 1 μg/ml, 20 μg/ml, 30 μg/ml and 40 μg/ml were set in total, while a negative control and a positive control were also set. The CHL cells were treated for 24 hours under the condition of −S9 and sections were prepared.

The numbers of monocytes, binucleate cells and multinucleated cells in 500 cells per dose were counted and the cytokinesis-block proliferation index (CBPI) and cytotoxicity at each dose were calculated.

In the maximum tolerated dose of tested substance in single oral gavage experiment in SD rat, 8 SD rats were randomly divided into two groups, with 4 female and 4 male in each group. After a single oral gavage administration, rats were observed continuously for 14 days and dissected on the 15th day. The following indicators were evaluated: clinical observation, body weight and pathology examination (macroscopic morphology).

EXAMPLE 1 Preparation of Compound 0604c 1.1 Preparation of 1-propyl-3,4-dihydro-2(1H)-quinolinone

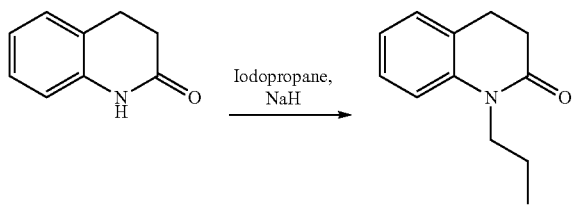

1.47 g (10 mmol) of 3,4-dihydro-2(1H)-quinolinone was added into 20 ml of anhydrous DMF, 0.48 g (60% in oil, 12 mmol) of sodium hydride was added in batches, after addition the mixture was stirred for 0.5 hours; then 2.04 g (12 mmol) of iodopropane was added dropwise, and the mixture was reacted at room temperature for 16 hours; the reaction was quenched by adding saturated ammonium chloride solution under ice bath, and extracted with ethyl acetate. The mixture was washed with saturated sodium chloride aqueous solution, and the organic phase was dried with anhydrous sodium sulfate. The solvent and excess iodopropane were distilled off under reduced pressure to give 1-propyl-3,4-dihydro-2 (1H)-quinolinone as an oil, which was used in the next step without further purification.

1.2 Preparation of 6-nitro-1-propyl-3,4-dihydro-2(1H)-quinolinone

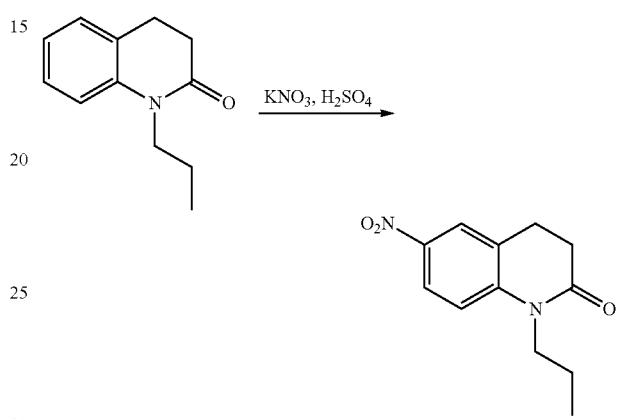

10 ml of concentrated sulfuric acid was added to 1.89 g (10 mmol) of 1-propyl-3,4-dihydro-2 (1H)-quinolinone under ice-water bath and stirred intensely for 0.5 hours; a dropping funnel was used to add potassium nitrate/sulfuric acid solution (1.01 g $KNO_3$ /10 ml $H_2SO_4$) dropwise. The reaction temperature was maintained below 5° C. and allowed to react for 2 hours. The reaction mixture was poured into ice water and stirred for 0.5 h, it was filtered and the filter cake was washed with plenty of water. The crude product is recrystallized with ethanol to give 1.65 g of a light yellow solid, with a yield of 70%. $^1$H NMR (400 MHz, $CDCl_3$): δ 8.16-7.05 (m, 3H), 3.95 (t, 2H), 3.00 (t, 2H), 2.71 (t, 2H), 1.72-1.63 (m, 2H), 0.98 (t, 3H) ppm.

1.3 Preparation of 6-amino-1-propyl-3,4-dihydro-2(1H)-quinolinone

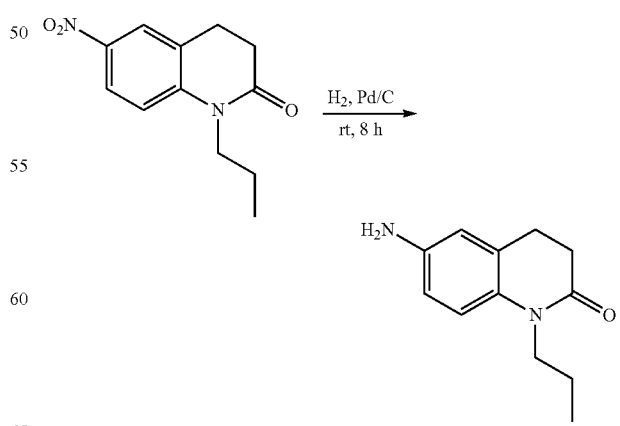

1.18 g (5 mmol) of 6-nitro-1-propyl-3,4-dihydro-2 (1H)-quinolinone was added into 50 ml of methanol, followed by the addition of palladium on carbon as a catalyst. Then the flask was evacuated and recharged with hydrogen three times, the mixture was allowed to stir for 8 h at room temperature. The catalyst was filtered and removed through a sand core funnel charged with diatomaceous earth in the reaction mixture. The filtrate was concentrated to give 6-amino-1-propyl-3,4-dihydro-2 (1H)-quinolinone, which was used in the next step without further purification.

1.4 Preparation of 3-fluoro-4-methylbenzylsulfonyl chloride

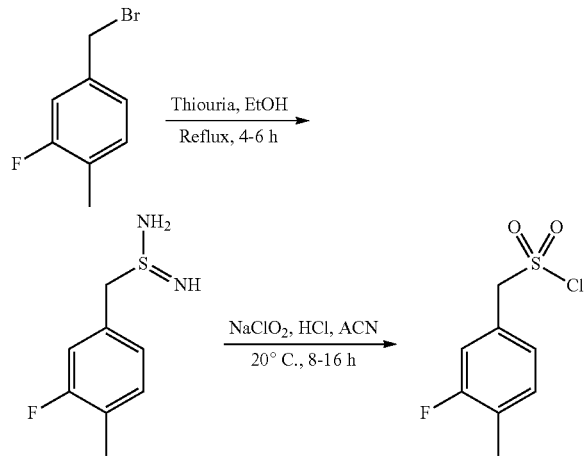

2.02 g (10 mmol) of 3-fluoro-4-methylbenzyl bromide and 0.76 g (10 mmol) of thiourea were dissolved in 50 ml of absolute ethanol and then the mixture was slowly heated to reflux, which was reacted for 4-6 hours. The solvent was evaporated under reduced pressure. 30 ml of acetonitrile and 10 ml of concentrated hydrochloric acid were added. The temperature was controlled below 20° C. and 5.4 g (60 mmol) of sodium chlorite was added in batches with intense stirring. The reaction was performed at 15-20° C. for 8-16 hours. The reaction was stopped by adding ice water and extracted with ethyl acetate. The extract liquor was concentrated to give 2.03 g of a white solid. 3-Fluoro-4-methylbenzylsulfonyl chloride was used in the next step without further purification.

1.5 Preparation of 0604c

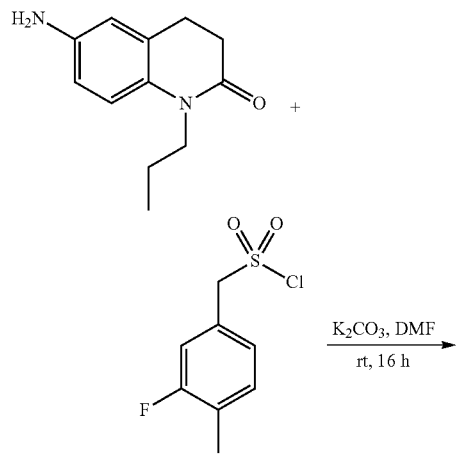

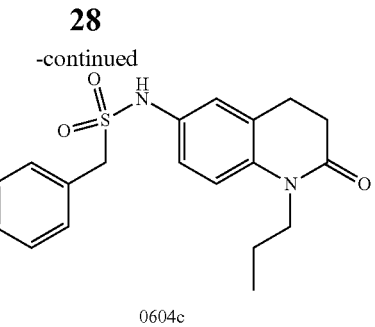

0604c 1.02 g (5 mmol) of 6-amino-1-propyl-3,4-dihydro-2 (1H)-quinolinone and 1.33 g (6 mmol) of 3-fluoro-4-methylbenzylsulfonyl chloride were added into 30 ml of DMF, followed by the addition of 2.01 g (15 mmol) of potassium carbonate as an acid-binding agent. The reaction was maintained at the room temperature and stirred for 16 hours. After the reaction was completed, ice water was added, and extracted with ethyl acetate. The organic phase was dried over anhydrous sodium sulfate and concentrated. The crude product was subjected to silica gel column chromatography to give 1.38 g of the title compound as a pale yellow solid, with a yield of 71%. $^1$H NMR (400 MHz, CDCl$_3$): δ 7.58-6.90 (m, 6H), 4.25 (s, 2H), 3.85 (t), 2.83 (t, 2H), 2.60 (t, 2H), 2.22 (s, 3H), 1.69-1.60 (m, 2H), 0.95 (t, 3H) ppm.

EXAMPLE 2 Preparation of Compound 1125A

2-Fluoro-4-methylbenzylsulfonyl chloride was prepared in the same manner as in step 1.4 of Example 1, except that 2-fluoro-4-methylbenzyl bromide was used instead of 3-fluoro-4-methylbenzyl bromide.

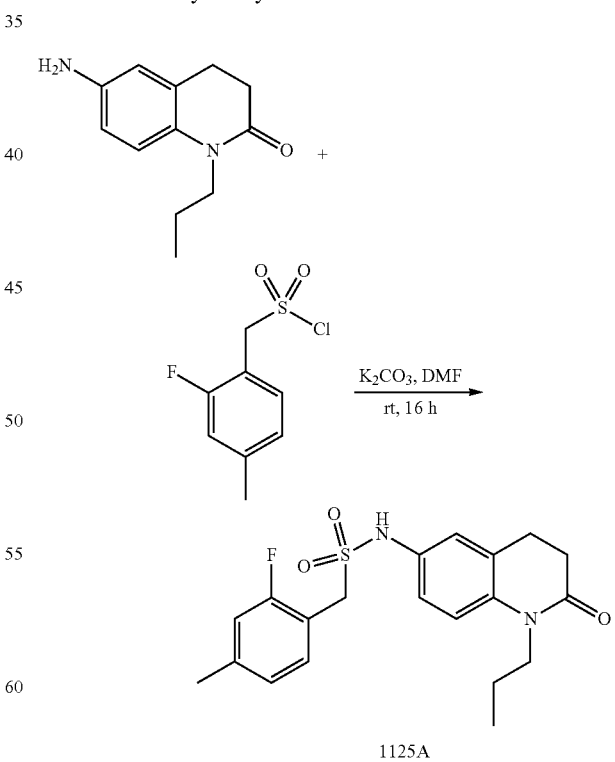

1125A 1.02 g (5 mmol) of 6-amino-1-propyl-3,4-dihydro-2 (1H)-quinolinone and 1.33 g (6 mmol) of 2-fluoro-4-methylbenzylsulfonyl chloride were added into 30 ml of DMF, followed by the addition of 2.01 g (15 mmol) of potassium carbonate as an acid-binding agent. The reaction was maintained at room temperature and stirred for 16 hours. After the reaction was completed, ice water was added, and extracted with ethyl acetate. The organic phase was dried over anhydrous sodium sulfate, and concentrated. The crude product was subjected to silica gel column chromatography to give 1.15 g of the title compound as a pale yellow solid, with a yield of 60%. $^1$H NMR (400 MHz, CDCl$_3$): δ 7.34-6.91 (m, 6H), 4.36 (s, 2H), 3.89 (t, 2H), 2.87 (t, 2H), 2.65 (t, 2H), 2.34 (s, 3H), 1.71-1.63 (m, 2H), 0.98 (t, 3H) ppm.

EXAMPLE 3 Preparation of Compound 1125B 3,5-Difluoro-4-methylbenzylsulfonyl chloride was prepared in the same manner as in Step 1.4 of Example 1, except that 3,5-difluoro-4-methylbenzyl bromide was used instead of 3-fluoro-4-methylbenzyl bromide.

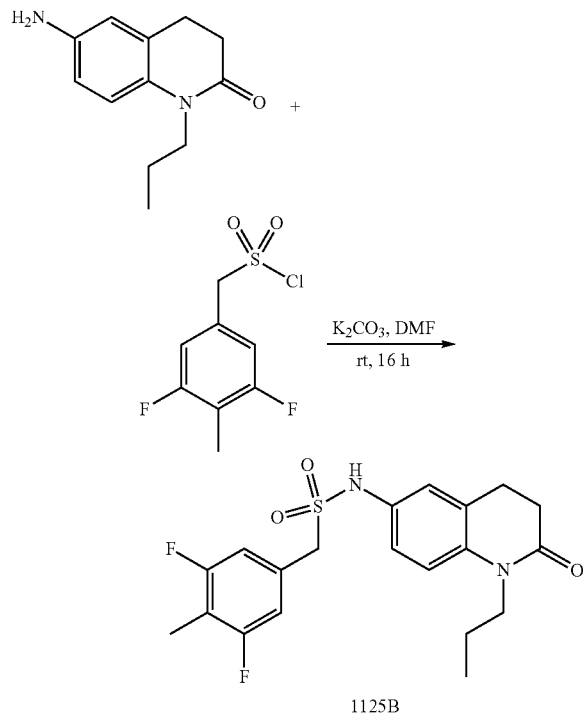

1125B 1.02 g (5 mmol) of 6-amino-1-propyl-3,4-dihydro-2 (1H)-quinolinone and 1.44 g (6 mmol) of 3,5-difluoro-4-methylbenzylsulfonyl chloride were added into 30 ml of DMF, followed by the addition of 2.01 g (15 mmol) of potassium carbonate as an acid-binding agent. The reaction was maintained at room temperature and stirred for 16 hours. After the reaction was completed, ice water was added, and extracted with ethyl acetate. The organic phase was dried over anhydrous sodium sulfate and concentrated. The crude product was subjected to silica gel column chromatography to give 0.98 g of the title compound as a pale yellow solid, with a yield of 48%. $^1$H NMR (400 MHz, DMSO-d$_6$): δ 9.75 (s, 1H), 7.09-6.96 (m, 5H), 4.49 (s, 2H), 3.80 (t, 2H), 2.80 (t, 2H), 2.53 (t, 2H), 2.13 (s, 3H), 1.60-1.49 (m, 2H), 0.88 (t, 3H) ppm.

EXAMPLE 4 Preparation of Compound 0918

2,3-Difluoro-4-methylbenzylsulfonyl chloride was prepared in the same manner as in Step 1.4 of Example 1, except that 2,3-difluoro-4-methylbenzyl bromide was used instead of 3-fluoro-4-methylbenzyl bromide.

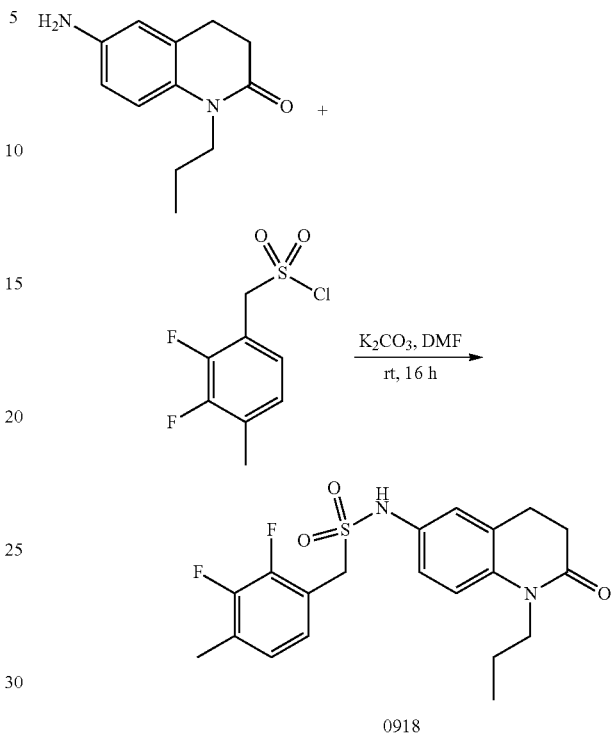

0918

1.02 g (5 mmol) of 6-amino-1-propyl-3,4-dihydro-2 (1H)-quinolinone and 1.44 g (6 mmol) of 2,3-difluoro-4-methylbenzylsulfonyl chloride were added into 30 ml of DMF, and then 2.01 g (15 mmol) of potassium carbonate was added as an acid-binding agent. The reaction was maintained at room temperature and stirred for 16 hours. After the reaction was completed, ice water was added, and extracted with ethyl acetate. The organic phase was dried over anhydrous sodium sulfate and concentrated. The crude product was subjected to silica gel column chromatography to give 1.12 g of the title compound as a pale yellow solid, with a yield of 55%. $^1$H NMR (400 MHz, CDCl$_3$): δ 7.09-6.79 (m, 5H), 4.42 (s, 2H), 3.89 (t, 2H), 2.87 (t, 2H), 2.65 (t, 2H), 2.29 (s, 3H), 1.73-1.63 (m, 2H), 0.98 (t, 3H) ppm.

EXAMPLE 5 Preparation of Compound 1127

2,3,5,6-Tetrafluoro-4-methylbenzylsulfonyl chloride was prepared in the same manner as in Step 1.4 of Example 1, except that 2,3,5,6-tetrafluoro-4-methylbenzyl bromine instead of 3-fluoro-4-methylbenzyl bromide.

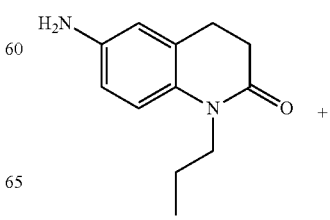

-continued

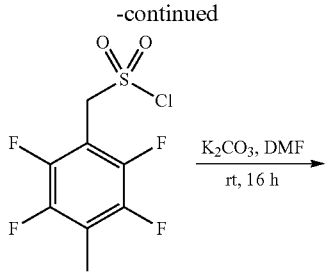

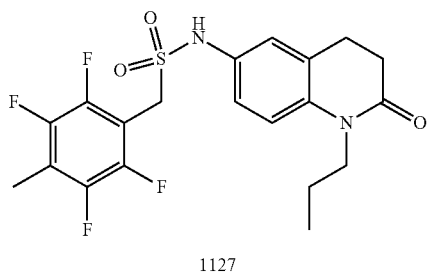

1127

1.02 g (5 mmol) of 6-amino-1-propyl-3,4-dihydro-2 (1H)-quinolinone and 1.66 g (6 mmol) of 2,3,5,6-tetrafluoro-4-methylbenzylsulfonyl chloride were added into 30 ml of DMF and 2.01 g (15 mmol) of potassium carbonate was added as an acid-binding agent. The reaction was maintained at room temperature and stirred for 16 hours. After the reaction was completed, ice water was added, and extracted with ethyl acetate. The organic phase was dried over anhydrous sodium sulfate and concentrated. The crude product was subjected to silica gel column chromatography to give 1.56 g of the title compound as a pale yellow solid, with a yield of 70%. $^1$H NMR (400 MHz, DMSO-$d_6$): δ 10.07 (s, 1H), 7.08-7.05 (m, 3H), 4.58 (s, 2H), 3.81 (t, 2H), 2.80 (t, 2H), 2.53 (t, 2H), 2.25 (s, 3H), 1.57-1.48 (m, 2H), 0.88 (t, 3H) ppm.

EXAMPLE 6 Preparation of Compound 1020A

3-Fluoro-4-trifluoromethylbenzylsulfonyl chloride was prepared in the same manner as in Step 1.4 of Example 1, except that 3-fluoro-4-trifluoromethylbenzyl bromide was used instead of 3-fluoro-4-methylbenzyl bromide.

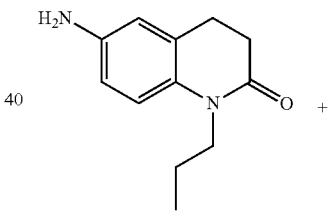

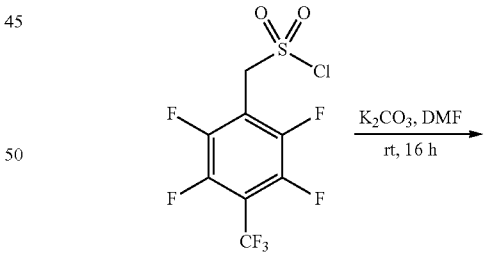

-continued

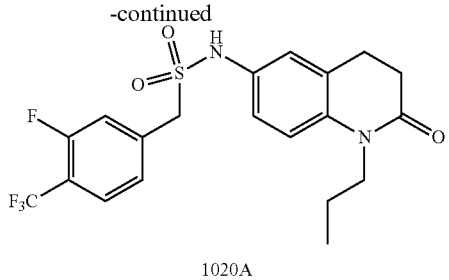

1020A 1.02 g (5 mmol) of 6-amino-1-propyl-3,4-dihydro-2 (1H)-quinolinone and 1.65 g (6 mmol) of 3-fluoro-4-trifluoromethylbenzylsulfonyl chloride were added into 30 ml of DMF, and followed by the addition of 2.01 g (15 mmol) of potassium carbonate as an acid-binding agent. The reaction was maintained at room temperature and stirred for 16 hours. After the reaction was completed, ice water was added, and extracted with ethyl acetate. The organic phase was dried over anhydrous sodium sulfate and concentrated. The crude product was subjected to silica gel column chromatography to give 0.85 g of the title compound as a pale yellow solid, with a yield of 39%. $^1$H NMR (400 MHz, DMSO-$d_6$): δ10.02 (s, 1H), 7.79-6.99 (m, 6H), 4.63 (s, 2H), 3.80 (t, 2H), 2.78 (t, 2H), 2.48 (t, 2H), 1.56-1.47 (m, 2H), 0.87 (t, 3H) ppm.

EXAMPLE 7 Preparation of Compound 1020B 2,3,5,6-Tetrafluoro-4-trifluoromethylbenzyl bromide is prepared in the same manner as in Step 1.4 of Example 1, except that 2,3,5,6-tetrafluoro-4-trifluoromethylbenzyl bromide was used instead of 3-fluoro-4-methylbenzyl bromide.

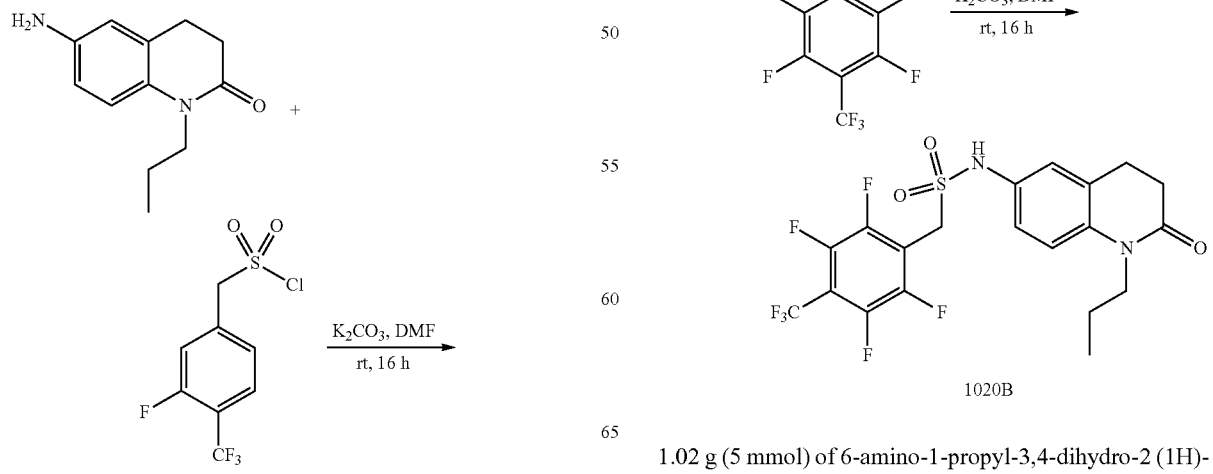

1020B 1.02 g (5 mmol) of 6-amino-1-propyl-3,4-dihydro-2 (1H)-quinolinone and 1.98 g (6 mmol) of 2,3,5,6-tetrafluoro-4- trifluoromethylbenzylsulfonyl chloride were added into 30 ml of DMF and 2.01 g (15 mmol) of potassium carbonate was added as an acid-binding agent. The reaction was maintained at room temperature and stirred for 16 hours. After the reaction was completed, ice water was added, and extracted with ethyl acetate. The organic phase was dried over anhydrous sodium sulfate and concentrated. The crude product was subjected to silica gel column chromatography to give 0.85 g of the title compound as a yellow solid, with a yield of 35%. $^1$H NMR (400 MHz, DMSO-$d_6$): δ10.17 (s, 1H), 7.07-7.05 (m, 3H), 4.74 (s, 2H), 3.78 (t, 2H), 2.79 (t, 2H), 2.48 (t, 2H), 1.56-1.49 (m, 2H), 0.86 (t, 3H) ppm.

EXAMPLE 8 Preparation of Compound 1103B

3-Chloro-4-methylbenzylsulfonyl chloride was prepared in the same manner as in Step 1.4 of Example 1, except that 3-chloro-4-methylbenzyl bromide was used instead of 3-fluoro-4-methylbenzyl bromide.

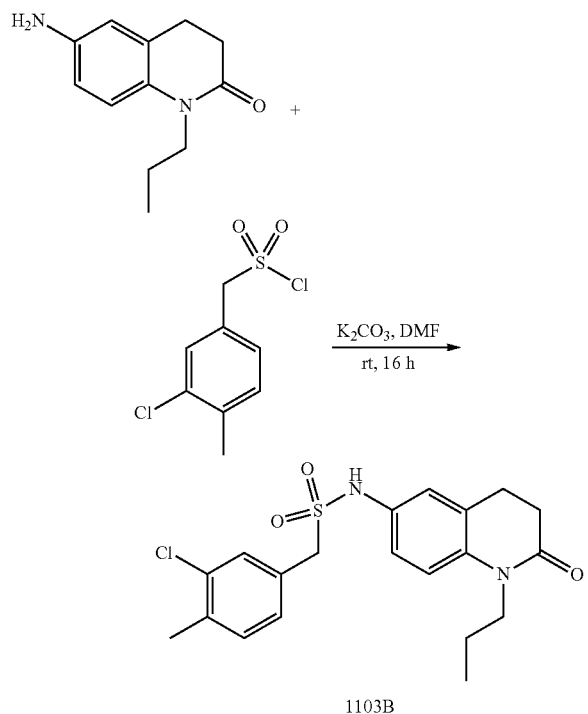

1103B 1.02 g (5 mmol) of 6-amino-1-propyl-3,4-dihydro-2 (1H)-quinolinone and 1.43 g (6 mmol) of 3-chloro-4-methylbenzylsulfonyl chloride were added into 30 ml of DMF, followed by the addition of 2.01 g (15 mmol) of potassium carbonate as an acid-binding agent. The reaction was maintained at room temperature and stirred for 16 hours. After the reaction was completed, ice water was added, and extracted with ethyl acetate. The organic phase was dried over anhydrous sodium sulfate and concentrated. The crude product was subjected to silica gel column chromatography to give 0.96 g of the title compound as a yellow solid, with a yield of 42%. $^1$H NMR (400 MHz, DMSO-$d_6$): δ10.17 (s, 1H), 7.41-6.96 (m, 6H), 4.41 (s, 2H), 3.81 (t, 2H), 2.78 (t, 2H), 2.23 (t, 2H), 1.99 (s, 3H), 1.56-1.50 (m, 2H), 0.87 (t, 3H) ppm.

EXAMPLE 9 Preparation of Compound 0925

2-Fluoro-4-chlorobenzylsulfonyl chloride was prepared in the same manner as in Step 1.4 of Example 1, except that 2-fluoro-4-chlorobenzyl bromide was used instead of 3-fluoro-4-methylbenzyl bromide.

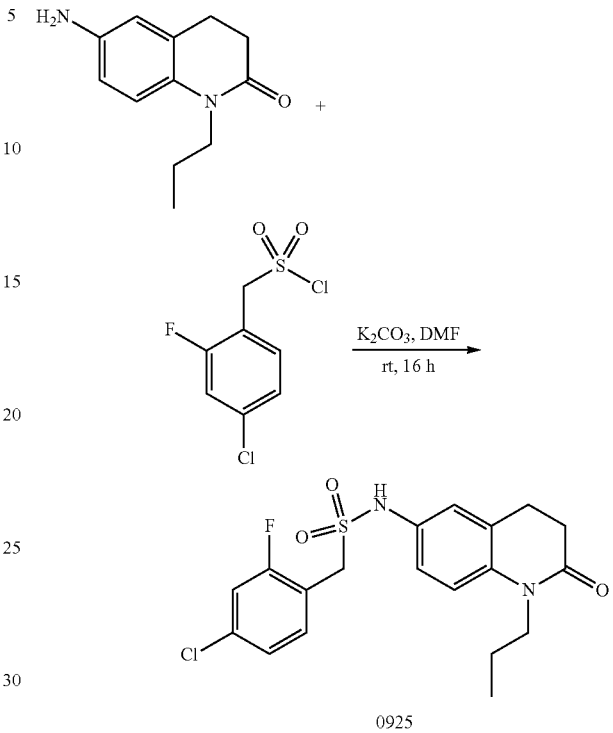

0925

1.02 g (5 mmol) of 6-amino-1-propyl-3,4-dihydro-2 (1H)-quinolinone and 1.45 g (6 mmol) of 2-fluoro-4-chlorobenzylsulfonyl chloride were added into 30 ml of DMF, followed by the addition of 2.01 g (15 mmol) of potassium carbonate as an acid-binding agent. The reaction was maintained at room temperature and stirred for 16 hours. After the reaction was completed, ice water was added, and extracted with ethyl acetate. The organic phase was dried over anhydrous sodium sulfate and concentrated. The crude product was subjected to silica gel column chromatography to give 0.83 g of the title compound as a yellow solid, with a yield of 40%. $^1$H NMR (400 MHz, CDCl$_3$): δ 7.63-6.90 (m, 6H), 4.39 (s, 2H), 3.87 (t, 2H), 2.87 (t, 2H), 2.61 (t, 2H), 1.71-1.61 (m, 2H), 0.96 (t, 3H) ppm.

EXAMPLE 10 Preparation of Compound 0703B

6-Amino-1-propyl-2 (1H)-quinolinone was prepared in the same manner as in Steps 1.1, 1.2 and 1.3 of Example 1, except that 2-hydroxyquinoline was used instead of 3,4-dihydro-2(1H)-quinolinone.

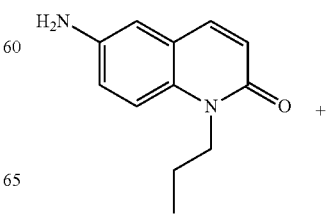

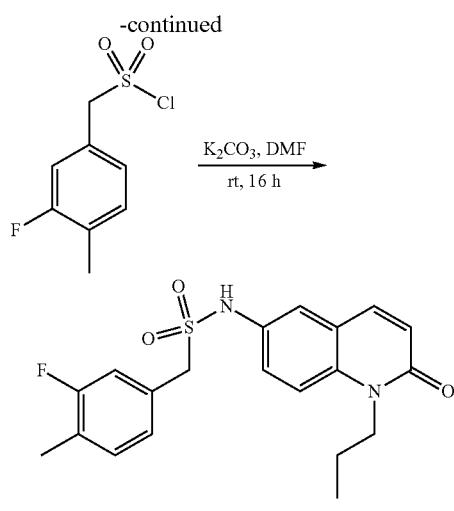

0703B 1.02 g (5 mmol) of 6-amino-1-propyl-2 (1H)-quinolinone and 1.33 g (6 mmol) of 3-fluoro-4-methyl benzylsulfonyl chloride were added into 30 ml of DMF, and 2.01 g (15 mmol) of potassium carbonate was added as an acid binding agent. The reaction was maintained at room temperature and stirred for 16 hours. After the reaction was completed, ice water was added, and extracted with ethyl acetate. The organic phase was dried over anhydrous sodium sulfate and concentrated. The crude product was subjected to silica gel column chromatography to give 1.44 g of the title compound as a pale yellow solid, with a yield of 75%. $^1$H NMR (400 MHz, DMSO-d$_6$): δ10.00 (s, 1H), 7.81-6.59 (m, 8H), 4.47 (s, 2H), 4.17 (t, 2H), 2.28 (s, 3H), 1.66-1.57 (m, 2H), 0.96 (t, 3H) ppm.

EXAMPLE 11 Preparation of Compound 0717

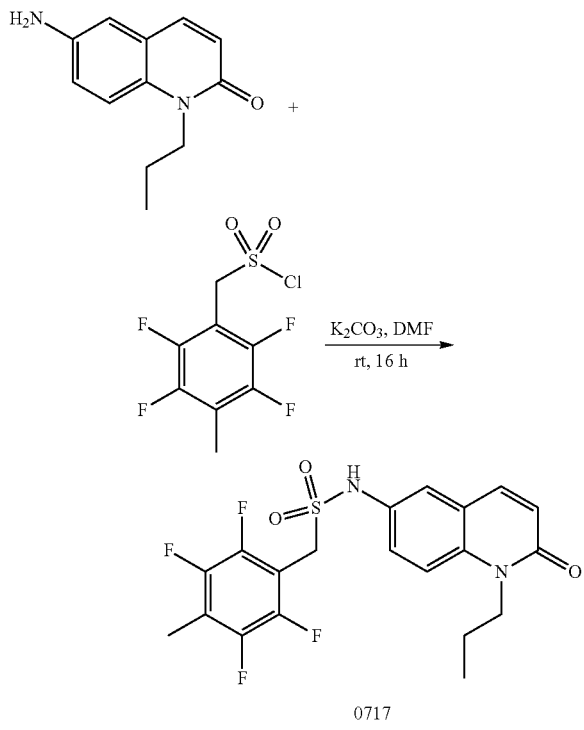

0717

1.01 g (5 mmol) of 6-amino-1-propyl-2(1H)-quinolinone and 1.66 g (6 mmol) of 2,3,5,6-tetrafluoro-4-methyl benzylsulfonyl chloride were added into 30 ml of DMF, followed by the addition of 2.01 g (15 mmol) of potassium carbonate as an acid-binding agent. The reaction was maintained at room temperature and stirred for 16 hours. After the reaction was completed, ice water was added, and extracted with ethyl acetate. The organic phase was dried over anhydrous sodium sulfate and concentrated. The crude product was subjected to silica gel column chromatography to give 1.35 g of the title compound as a yellow solid, with a yield of 64%. $^1$H NMR (400 MHz, DMSO-d$_6$): δ10.29 (s, 1H), 7.86-6.60 (m, 5H), 4.64 (s, 2H), 4.15 (t, 2H), 2.19 (s, 3H), 1.69-1.57 (m, 2H), 0.96 (t, 3H) ppm.

EXAMPLE 12 Preparation of Compound 0707

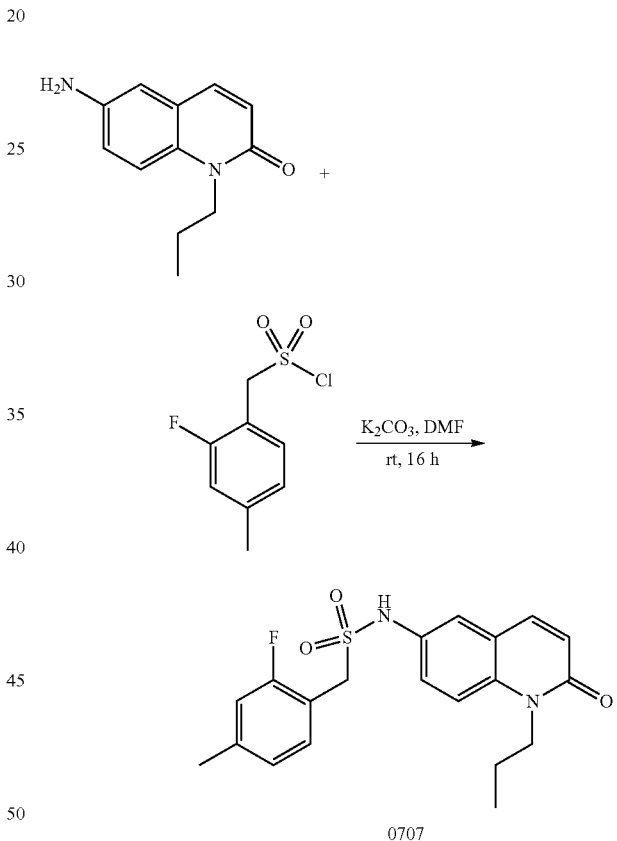

0707

1.01 g (5 mmol) of 6-amino-1-propyl-2(1H)-quinolinone and 1.33 g (6 mmol) of 2-fluoro-4-methyl benzylsulfonyl chloride were added into 30 ml of DMF, and 2.01 g (15 mmol) potassium carbonate was added as an acid binding agent. The reaction was maintained at room temperature and stirred for 16 hours. After the reaction was completed, ice water was added, and extracted with ethyl acetate. The organic phase was dried over anhydrous sodium sulfate and concentrated. The crude product was subjected to silica gel column chromatography to give 1.23 g of the title compound with a yield of 64%. $^1$H NMR (400 MHz, DMSO-d$_6$): δ9.90 (s, 1H), 7.91-6.59 (m, 8H), 4.49 (s, 2H), 4.16 (t, 2H), 2.18 (s, 3H), 1.67-1.55 (m, 2H), 0.95 (t, 3H) ppm.

EXAMPLE 13 Preparation of Compound 0714

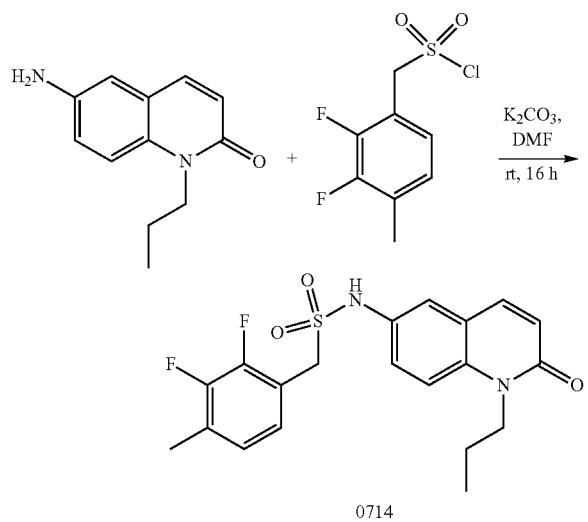

0714

1.02 g (5 mmol) of 6-amino-1-propyl-2 (1H)-quinolinone and 1.44 g (6 mmol) of 2,3-difluoro-4-methyl benzylsulfonyl chloride were added into 30 ml of DMF, and 2.01 g (15 mmol) of potassium carbonate was added as an acid-binding agent. The reaction was maintained at room temperature and stirred for 16 hours. After the reaction was completed, ice water was added, and extracted with ethyl acetate. The organic phase was dried over anhydrous sodium sulfate and concentrated. The crude product was subjected to silica gel column chromatography to give 1.45 g of the title compound with a yield of 71%. $^1$H NMR (400 MHz, DMSO-$d_6$): δ10.07 (s, 1H), 7.87-6.61 (m, 8H), 4.55 (s, 2H), 4.15 (t, 2H), 2.57 (s, 3H), 1.67-1.58 (m, 2H), 0.95 (t, 3H) ppm.

EXAMPLE 14 Preparation of Compound 130925AMX

6-Amino-1-allyl-3,4-dihydro-2 (1H)-quinolinone was prepared in the same manner as in Steps 1.1, 1.2 and 1.3 of Example 1, except that 3-bromopropene was used instead of 3-iodopropane.

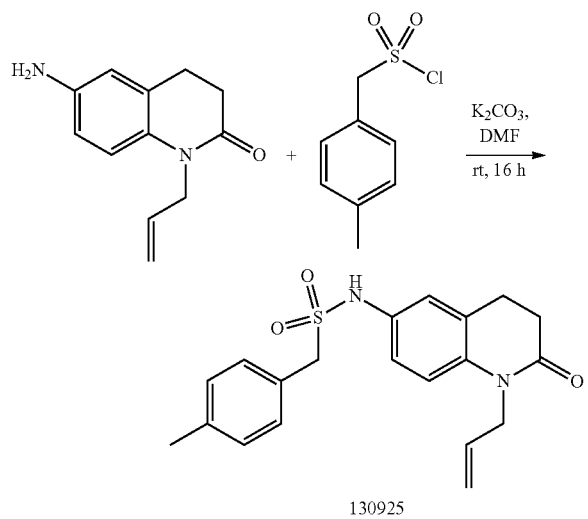

130925

1.01 g (5 mmol) of 6-amino-1-allyl-3,4-dihydro-2 (1H)-quinolinone and 1.23 g (6 mmol) of 4-methyl benzylsulfonyl chloride were added into 30 mL of DMF, and 2.01 g (15 mmol) of potassium carbonate was added as an acid-binding agent. The reaction was maintained at room temperature and stirred for 16 hours. After the reaction was completed, ice water was added, and extracted with ethyl acetate. The organic phase was dried over anhydrous sodium sulfate and concentrated. The crude product was subjected to silica gel column chromatography to give 1.36 g of the compound 130925 as a pale yellow solid, with a yield of 73%. 1H NMR (400 MHz, CDCl$_3$): δ 7.22-6.93 (m, 7H), 5.91-5.83 (m, 1H), 5.25-5.13 (dd, 2H), 4.54 (s, 2H), 4.27 (d, 2H), 2.89 (t, 2H), 2.68 (t, 2H), 2.32 (s, 3H) ppm.

Similarly, repeating the above procedures, 3-fluoro-4-methyl benzylsulfonyl chloride was used instead of 4-methylbenzenesulfonyl chloride to prepare the AMX compound, which is 130925AMX.

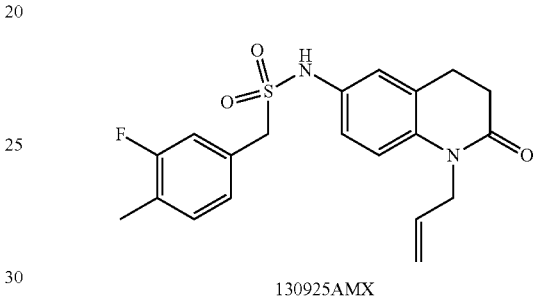

130925AMX

EXAMPLE 15 Preparation of Compound 140228AMX

6-Amino-4-methyl-1-propyl-2(1H)-quinolinone was prepared in the same manner as in Steps 1.1, 1.2 and 1.3 of Example 1, except that 2-hydroxy-4-methylquinoline was used instead of 3,4-dihydro-2 (1H)-quinolinone.

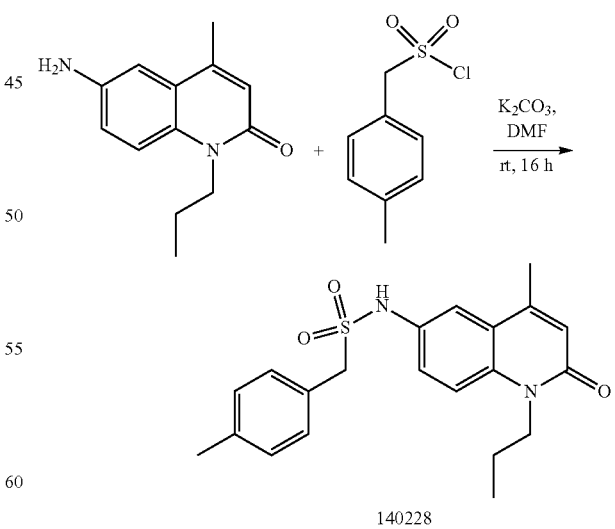

140228

1.08 g (5 mmol) of 6-amino-4-methyl-1-propyl-2 (1H)-quinolinone and 1.23 g (6 mmol) of 4-methyl benzylsulfonyl chloride were added into 30 ml of DMF, and 2.01 g (15 mmol) of potassium carbonate was added as an acid-binding agent. The reaction was maintained at room temperature and stirred for 16 hours. After the reaction was completed, ice water was added, and extracted with ethyl acetate. The organic phase was dried over anhydrous sodium sulfate and concentrated. The crude product was subjected to silica gel column chromatography to give 1.15 g of the compound 140228, as a pale yellow solid, with a yield of 62%.

Similarly, repeating the above procedures, 3-fluoro-4-methyl benzylsulfonyl chloride was used instead of 4-methyl benzylsulfonyl chloride to prepare the AMX compound, which is 140228 AMX.

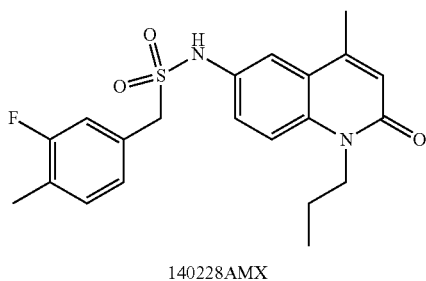 [SMILES: CCCn1c(=O)cc(C)c2cc(NS(=O)(=O)Cc3ccc(C)c(F)c3)ccc21]

140228AMX

EXAMPLE 16 Preparation of Compound 0720B

16.1 Preparation of 4-methyl-3,4-dihydro-2 (1H)-quinolinone

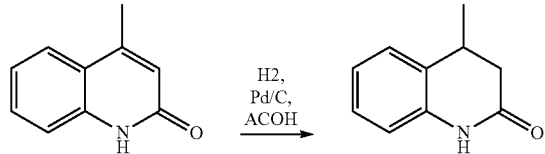

3.0 g of 4-methylquinolinone was added into 200 mL of acetic acid, and 300 mg of palladium on carbon was added under nitrogen atmosphere, then the reaction flask was recharged with hydrogen for three times. The reaction mixture was heated to 70° C. and reacted for 12 hours. The mixture was filtered under vacuum through a sand core funnel charged with diatomaceous earth and the filtrate was concentrated under reduced pressure to give 2.7 g of a pale yellow solid, with a yield of 90%. $^1$HNMR (400 MHz, DMSO-d$_6$): δ 10.11 (s, 1H), 6.84-7.20 (m, 4H), 3.04 (m, 1H), 2.59 (dd, 1H), 2.22 (dd, 1H), 1.17 (d, 3H) ppm.

16.2 Preparation of 4-methyl-1-propyl-3,4-dihydro-2 (1H)-quinolinone

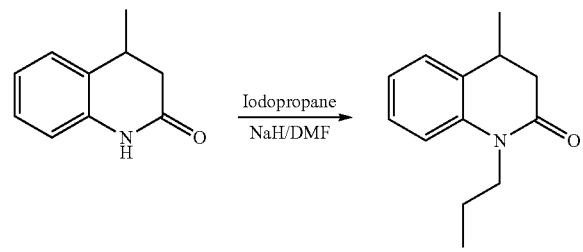

2.0 g of 4-methyl-3,4-dihydro-2 (1H)-quinolinone was added into 80 mL of N, N-dimethylformamide, and 1.05 equivalent of sodium hydride was added in batches under stirring in an ice-water bath. After the addition, the mixture was stirred for 0.5 hours; 1.1 equivalents of iodopropane was added dropwise, the ice-water bath was removed and the reaction was carried out for 12 hours; the reaction was quenched by the addition of saturated ammonium chloride solution and extracted with ethyl acetate. The combined organic phases were washed with saturated aqueous sodium chloride, and anhydrous sodium sulfate was added to dry the organic phase. The solvent and excess iodopropane were distilled off under reduced pressure to give 2.2 g of a pale yellow oily liquid. The crude product was without further purification, the crude yield was 88%.

16.3 Preparation of 4-methyl-6-nitro-1-propyl-3,4-dihydro-2 (1H)-quinolinone

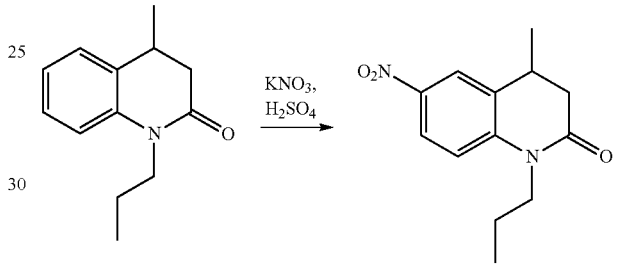

20 mL of sulfuric acid was added into a flask charged with 2.0 g of 4-methyl-1-propyl-3,4-dihydro-2 (1H)-quinolinone under an ice-water bath and then stirred intensely for 0.5 hours; 1.1 equivalents of sulfuric acid solution of potassium nitrate was slowly added dropwise through a dropping funnel. The mixture was maintained at a temperature in an ice-water bath and reacted for 1-2 hours; the reaction solution was poured in ice water and stirred for half an hour. It was filtered and the filter cake was washed with plenty of water. The crude product was recrystallized with ethanol to give 1.8 g of 4-methyl-6-nitro-1-propyl-3,4-dihydro-2 (1H)-quinolinone, with a yield of 77%. $^1$HNMR (400 MHz, DMSO-d6): δ 8.22-7.32 (m, 3H), 3.93 (m, 2H), 3.26 (m, 1H), 2.76 (dd, 1H), 2.44 (dd, 1H), 1.64 (m, 2H), 1.22 (d, 3H), 0.89 (t, 3H) ppm.

16.4 Preparation of 16-amino-4-methyl-1-propyl-3,4-dihydro-2 (1H)-quinolinone

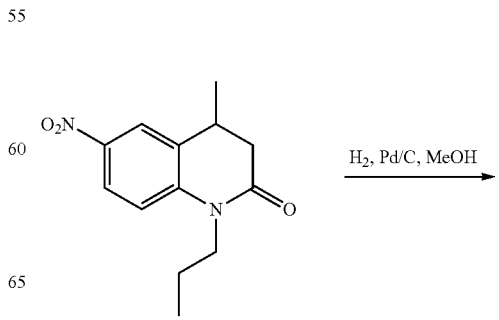

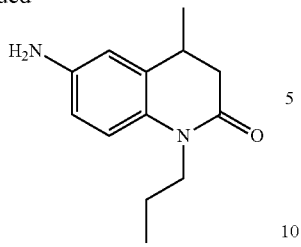

1.8 g of 4-methyl-6-nitro-1-propyl-3,4-dihydro-2 (1H)-quinolinone was added into methanol, and palladium on carbon was added as a catalyst. The reaction was recharged with hydrogen for three times, and stirred at room temperature for 8 hours. The reaction mixture was filtered and the solid was removed through a sand core funnel charged with diatomaceous earth in the. The filtrate was concentrated to give 1.4 g of 6-amino-4-methyl-1-propyl-3,4-dihydro-2 (1H)-quinolinone, which was used in the next step without further purification, with a yield of 90%.

16.5 Preparation of 2,3,5,6-tetrafluoro-4-methylbenzylsulfonyl chloride

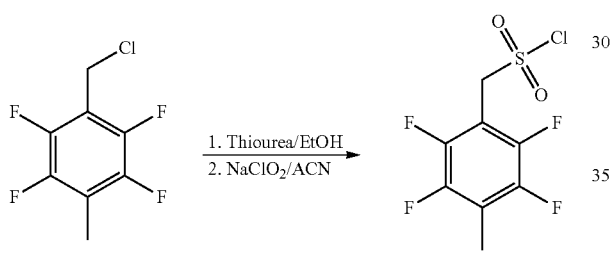

2,3,5,6-Tetrafluoro-4-methylbenzyl chloride and 1 equivalent of thiourea were dissolved in ethanol and then slowly heated to reflux. After reacting for 4-6 hours, the reaction solution was concentrated. Acetonitrile and concentrated hydrochloric acid were added. The temperature was controlled at 5-10° C., 1.5 equivalents of sodium chlorite were added in batches with intense stirring. The reaction was performed at 15-20° C. for 8-16 hours. Ice water was added to stop the reaction. Ethyl acetate was used for extraction for three times. The extract was concentrated to give 2,3,5,6-tetrafluoro-4-methyl benzylsulfonyl chloride, which was used in the next step without further purification.

16.6 Preparation of Compound 0720B

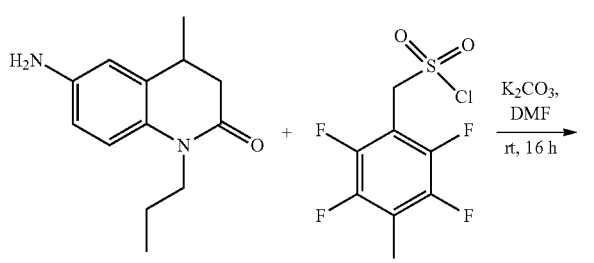

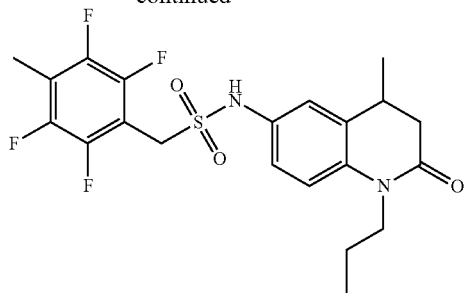

0720B 1.0 g of 6-amino-4-methyl-1-propyl-3,4-dihydro-2 (1H)-quinolinone and 1 equivalent of 2,3,5,6-tetrafluoro-4-methyl benzylsulfonyl chloride were added into DMF, followed by the addition of 3 equivalents of potassium carbonate as an acid-binding agent. The reaction was maintained at room temperature and stirred for 16 hours. After the reaction was completed, ice water was added, and extracted with ethyl acetate. The organic phase was dried over anhydrous sodium sulfate and concentrated. The crude product was subjected to silica gel column chromatography to give 1.5 g of the compound 0720B, with a yield of 70%.

$^1$HNMR (400 MHz, DMSO-d6): δ 10.10 (s, 1H), 7.06-7.12 (m, 3H), 4.59 (s, 2H), 3.80 (m, 2H), 2.93 (m, 1H), 2.61 (dd, 1H), 2.31 (dd, 1H), 2.23 (s, 3H), 1.60 (m, 2H), 1.11 (d, 3H), 0.98 (t, 3H) ppm.

EXAMPLE 17 Preparation of Compound 0825A

17.1 Preparation of 3-methyl-N-phenyl-butenamide

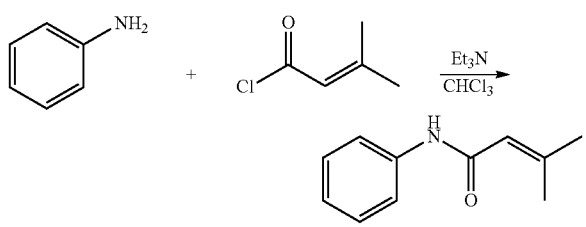

4.9 g of aniline was added into 100 mL of chloroform, and 3 molar equivalents of triethylamine were added. 1.1 molar equivalents of 3-methylbutenoyl chloride were added dropwise with stirring and the temperature was controlled below less than 5° C. through ice bath. After the addition was completed, the ice bath was removed, and the temperature was slowly warmed to reflux, then the reaction was performed for 2 hours, and evaporated to dryness under reduced pressure to give 8.2 g of 3-methyl-N-phenyl-butenamide, with a yield of 89%.

17.2 Preparation of 4,4-dimethyl-3,4-dihydro-2 (1H)-quinolinone

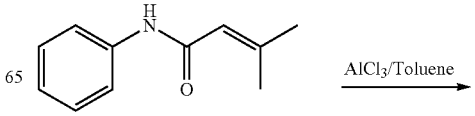

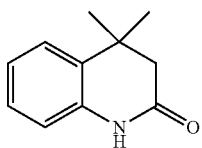

7.0 g of 3-methyl-N-phenyl-butenamide was added into 50 mL of toluene, and 18 g of anhydrous aluminum trichloride was added. The temperature was slowly increased to 80° C. The reaction was performed for 2.5 hours, and evaporated to dryness under reduced pressure, and the residue was purified through silica gel column chromatography to give 4.7 g of a light yellow solid. $^1$HNMR (400 MHz, DMSO-d6): δ 10.12 (s, 1H), 6.86-7.29 (m, 4H), 2.34 (s, 2H), 1.82 (s, 6H) ppm.

17.3 Preparation of 4,4-dimethyl-1-propyl-3,4-dihydro-2 (1H)-quinolinone

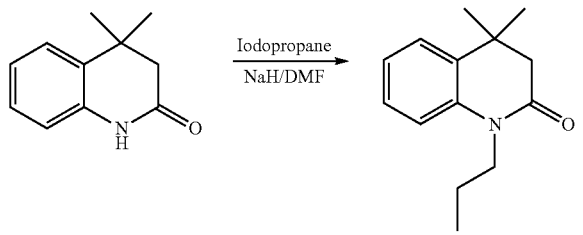 [SMILES: CC1(C)CC(=O)Nc2ccccc21 ; CCCN1C(=O)CC(C)(C)c2ccccc21]

4.0 g of 4, 4-dimethyl-3,4-dihydro-2 (1H)-quinolinone was added into 80 mL of N, N-dimethylformamide, and 1.05 Equivalents of sodium hydride were added in batches under an ice-bath with stirring. After addition, the mixture was stirred for 0.5 hour; then 1.1 equivalents of iodine propane were added dropwise, then the ice water bath was removed, and the reaction was performed for 12 hours. The reaction was quenched by adding saturated ammonium chloride solution, and ethyl acetate was added for extraction. The organic phases were combined, washed with saturated aqueous sodium chloride and dried over anhydrous sodium sulfate. The solvent and excess iodopropane were distilled off under reduced pressure to give 4.4 g of pale yellow oily liquid, with a yield of 89%. 17.4 Preparation of 4,4-dimethyl-6-nitro-1-propyl-3,4-dihydro-2 (1H)-quinolinone

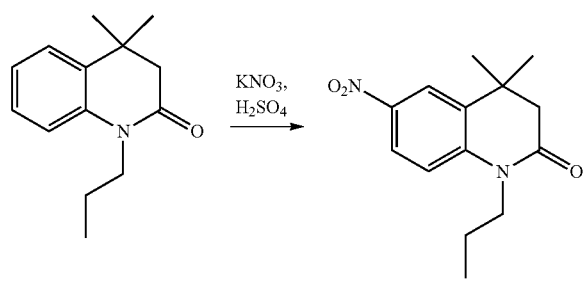 [SMILES: CCCN1C(=O)CC(C)(C)c2ccccc21 ; CCCN1C(=O)CC(C)(C)c2cc([N+](=O)[O-])ccc21]

20 mL of sulfuric acid was added into a flask charged with 4.0 g of 4,4-dimethyl-1-propyl-3,4-dihydro-2 (1H)-quinolinone under an ice bath and stirred intensely for 0.5 hours; 1.1 equivalents of a sulfuric acid solution of potassium nitrate was slowly added dropwise through a dropping funnel, and the temperature was maintained under an ice-water bath and the reaction was performed for 1-2 hours; the reaction liquid was poured into ice water and stirred for 0.5 hours. Filtered and the filter cake was washed with plenty of water, and dried under the infrared light. The crude product was recrystallized with ethanol. 3.6 g of 4,4-dimethyl-6-nitro-1-propyl-3,4-dihydro-2 (1H)-quinolinone was obtained in a yield of 77%.

17.5 Preparation of 6-amino-4,4-dimethyl-1-propyl-3,4-dihydro-2 (1H)-quinolinone

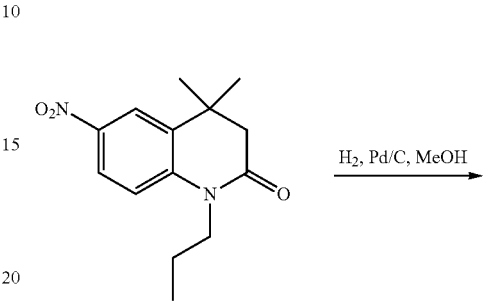

4.0 g of 4,4-dimethyl-6-nitro-1-propyl-3,4-dihydro-2 (1H)-quinolinone was added into 50 mL of methanol, and 300 mg of palladium on carbon was added as a catalyst. The reaction system was recharged with hydrogen for three times. The reaction was stirred for 8 hours at room temperature. The reaction mixture was filtered through a sand core funnel charged with diatomaceous earth and the solid was removed. The filtrate was condensed to give 3.1 g of 6-amino-4,4-dimethyl-1-propyl-3,4-dihydro-2 (1H)-quinolinone, which was used in the next step without further purification, with a yield of 89%.

17.6 Preparation of 0825A

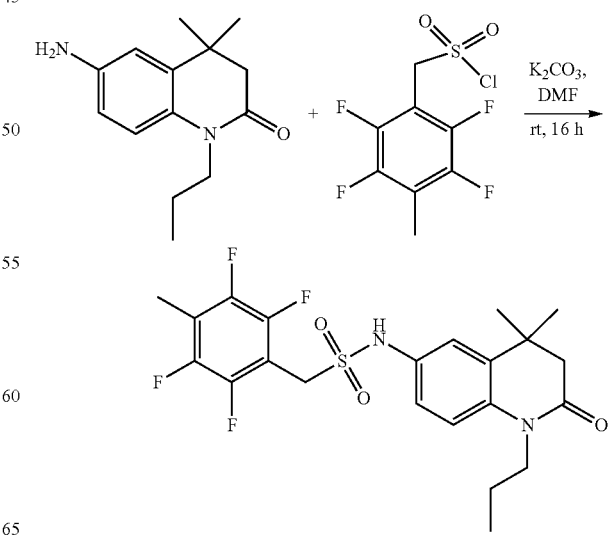

0825A 1.0 g of 6-amino-4,4-dimethyl-1-propyl-3,4-dihydro-2 (1H)-quinolinone and 1 equivalent of 2,3,5,6-tetrafluoro-4-methyl benzylsulfonyl chloride were added into DMF, and 3 equivalents of potassium carbonate were added as an acid-binding agent. The reaction was maintained at room temperature and stirred for 16 hours. After the reaction was completed, ice water was added, and extracted with ethyl acetate. The organic phase was dried over anhydrous sodium sulfate and concentrated. The crude product was purified through silica gel column chromatography to give 1.9 g of a pale yellow compound 0825A, with a yield of 78%. $^1$HNMR (400 MHz, DMSO-d6): δ 10.07 (s, 1H), 7.09-7.18 (m, 3H), 4.58 (s, 2H), 3.87 (t, 2H), 2.41 (s, 2H), 2.23 (s, 3H), 1.61 (m, 2H), 1.20 (s, 6H), 0.91 (t, 3H) ppm.

EXAMPLE 18 In-Vitro Assay on Activity of AMX Compounds (Compound 0604c, Compound 0918 and Compound 1127)

18.1 In-Vitro Biochemical Experiments and PP2C Protein Phosphatase Activity Test In-vitro biochemical experiments suggested that the AMX compounds of the present invention, as a series of broad-spectrum and efficient PYL receptor agonists, had high binding affinities to a plurality of PYL receptors and promoted PYL receptors to bind and inhibit PP2C protein phosphatase activity.

The experiment of activity of HAB1 protein phosphatase, wherein a SnRK2.6 phosphorylated polypeptide was used as a substrate, showed that AMX could promote the binding between PYL2 receptor and PP2C protein phosphatase (HAB1), thus inhibiting the dephosphorylation effect of HAB1 on SnRK2.6 phosphorylated polypeptide. Further, the effect was significantly better than that of ABA at the same concentration.

A broad spectrum experiment based on the binding ability of compound 0604c and compound 0918 for PYR/PYL receptor showed that they could bind with PYR1/PYL1/PYL2/PYL3/PYL4/PYL5/PYL7/PYL10 at a concentration of 1 μM, wherein their binding ability with PYR1/PYL1/PYL2/PYL7 were significantly higher than those of ABA (FIG. 1). The above results suggested that, AMX was a broad-spectrum and efficient PYL receptor agonist.

18.2 AlphaScreen Experiment

AlphaScreen technology was used to test the ability of AMX to promote PYL receptor binding to PP2C protein phosphatase (HAB1).

Figure 2:
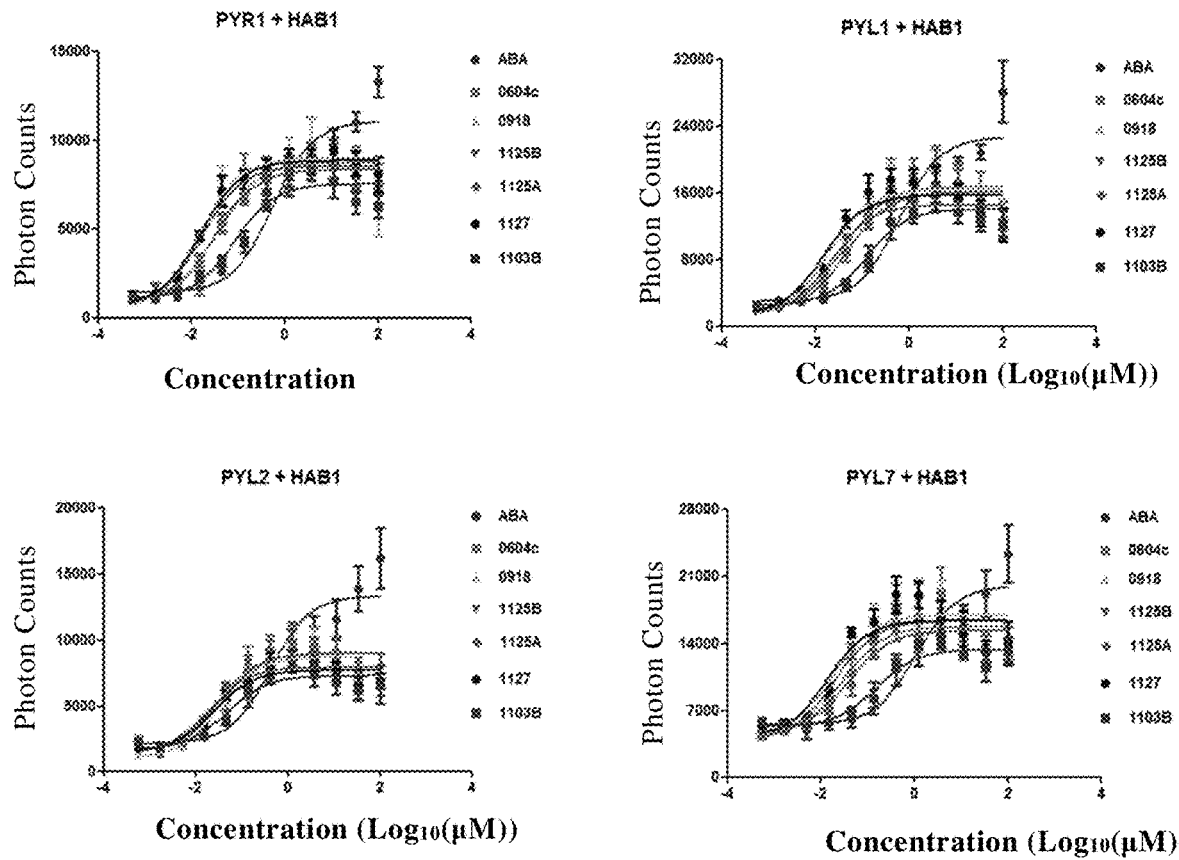
FIG. 2 shows a dose response curve of *Arabidopsis* PYR/PYL receptor agonists including six AMX compounds (0604c, 0918, 1125A, 1125B, 1127 and 1103B) and ABA. AMX compounds can promote the interaction of protein phosphatase HAB1 with the four *Arabidopsis* PYR/PYL receptors (PYR1, PYL1, PYL2 and PYL7), and this effect is dose-dependent.
Figure 3:
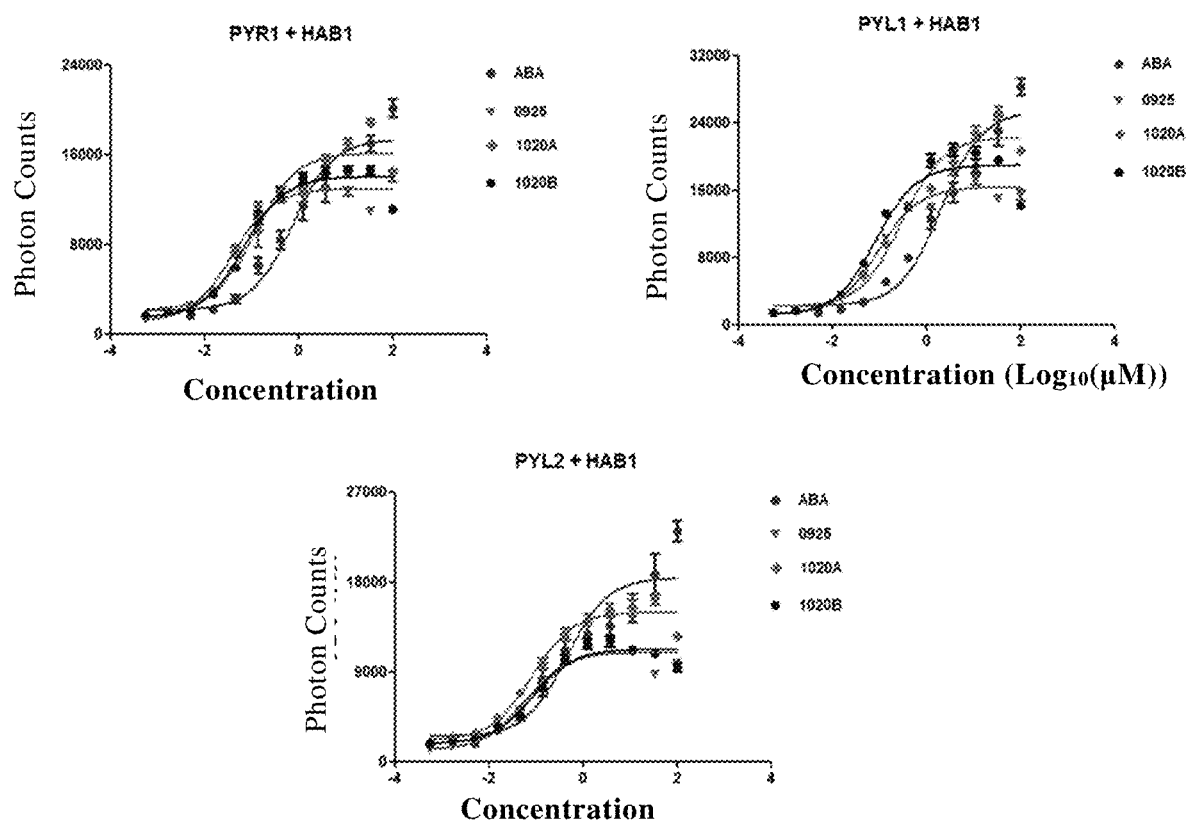
FIG. 3 shows a dose response curve of PYR/PYL receptor agonists including three AMX compounds (0925, 1020A and 1020B) and ABA. AMX compounds can promote the interaction of protein phosphatase HAB1 with three PYR/PYL receptors (PYR1, PYL1 and PYL2), and this interaction is dose-dependent.

Experimental results showed that AMX was significantly superior to ABA on PYL receptor binding affinities for PYR1/PYL1/PYL2/PYL7 (FIG. 2 and FIG. 3). In the presence of various AMX compounds, all of the above four PYL receptors had significantly better affinity for HAB1 than that in the presence of ABA and existing ABA analogs. Moreover, the $EC_{50}$ value of AMX was 1-2 orders of magnitude less than that of ABA, and there was a dose-dependent effect of AMX on the binding ability of the four PYL receptors for HAB1 (FIG. 2 and FIG. 3).

Figure 9:
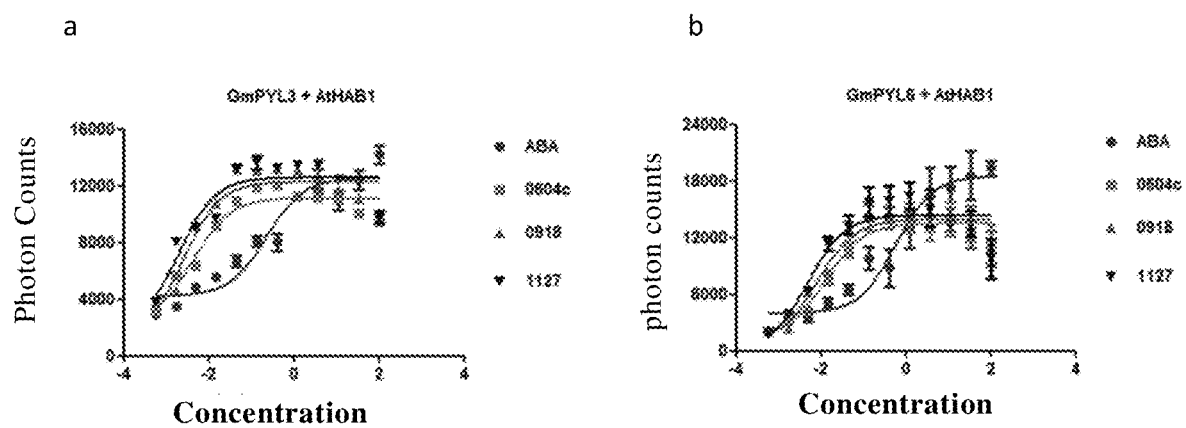
FIG. 9 shows a dose response curve of soybean PYR/PYL receptor agonists for three AMX compounds (0604c, 0918 and 1127) and ABA. AMX compounds can promote the interaction of the *Arabidopsis* protein phosphatase HAB1 with two soybean PYR/PYL receptors (GmPYL3 and GmPYL6) and this interaction is dose-dependent.

In addition, experiments using soybean GmPYL3 (homologous gene for *Arabidopsis* PYL1) and GmPYL6 (homologous gene for *Arabidopsis* PYL2) and *Arabidopsis* AtHAB1 showed that compound 0604c, compound 0918 and compound 1127 all had significantly higher affinities for soybean GmPYL proteins than that of ABA (FIG. 9).

The above results suggested that AMX compounds such as compound 0604c, compound 0918 and compound 1127 were a series of PYL receptor agonists that were more efficient than existing compounds such as ABA.

EXAMPLE 19 In-Vitro Assay of Activity for AMX Compounds (Compound 0720B and 0825A)

19.1 In-Vitro Biochemical Experiments and PP2C Protein Phosphatase Activity Test In-vitro biochemical experiments showed that the compounds 0720B and 0825A of the present invention, as a series of efficient PYL receptor agonists, had high binding affinities to a plurality of PYL receptors and promoted PYL receptors to bind and inhibit PP2C protein phosphatase activity.

The experiment of activity of HAB1 protein phosphatase, wherein a SnRK2.6 phosphorylated polypeptide was used as a substrate, showed that compounds 0720B and 0825A could both promote the binding between PYL2 receptor and PP2C protein phosphatase (HAB1), thus inhibiting the dephosphorylation effect of HAB1 on SnRK2.6 phosphorylated polypeptide. Further, the effect was significantly better than that of ABA at the same concentration (Table 1).

Figure 13:
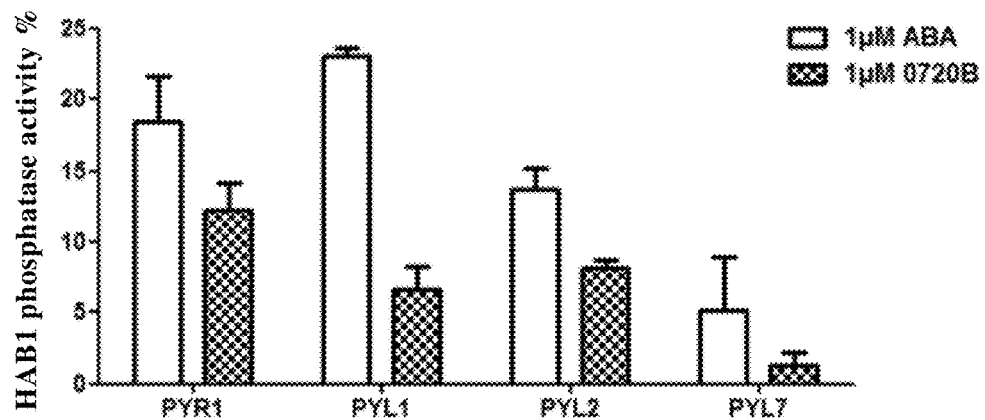
FIG. 13 shows that compound 0720B of the present invention can bind to the *Arabidopsis* PYR/PYL receptors (PYR1, PYL1, PYL2 and PYL7)-HAB1 complex, thereby inhibiting the activity of protein phosphatase HAB1. At a concentration of 1 μM, the inhibitory effect of the compound is significantly better than that of ABA.

A broad spectrum experiment based on the binding ability of compound 0720B for PYR/PYL receptor showed that the binding ability thereof for PYR1/PYL1/PYL2/PYL7 was significantly higher than that of ABA (FIG. 13). The above results showed that compound 0720B was a broad-spectrum and efficient PYL receptor agonist.

19.2 AlphaScreen Experiment

AlphaScreen technology was used to test the ability of compound 0720B to promote PYL receptor binding to PP2C protein phosphatase (HAB1).

Figure 14:
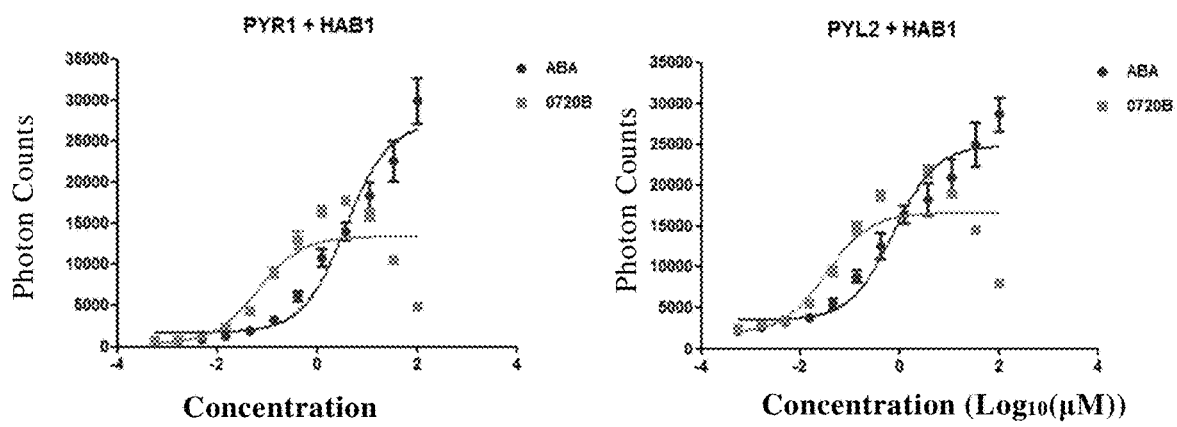
FIG. 14 shows a dose response curve of *Arabidopsis* PYR/PYL receptor agonists for compound 0720B of the present invention and ABA. The compound 0720B can promote the interaction between protein phosphatase HAB1 and any of two *Arabidopsis* PYR/PYL receptors (PYR1 and PYL2). The interaction is dose-dependent.

Experimental results showed that, as for *Arabidopsis* PYL2 receptor and PYL1 receptor, compound 0720B was significantly superior to ABA on PYL receptor bidning affinity (FIG. 2), and the $EC_{50}$ value of 0720B was 1-2 orders of magnitude less than that of ABA (Table 1), indicating that there was a dose-dependent effect of compound 0720B on the binding ability of two PYL receptors for HAB1 (FIG. 14).

The above results show that AMX compounds (such as compound 0720B and 0825A) are more efficient PYL receptor agonists than existing compounds such as ABA.

EXAMPLE 20 Physiological Activity Test for AMX Compounds (0604c, 1125A, 1125B, 0918, 1127)

20.1 Inhibition Effect on *Arabidopsis* Seed Germination

Figure 6:
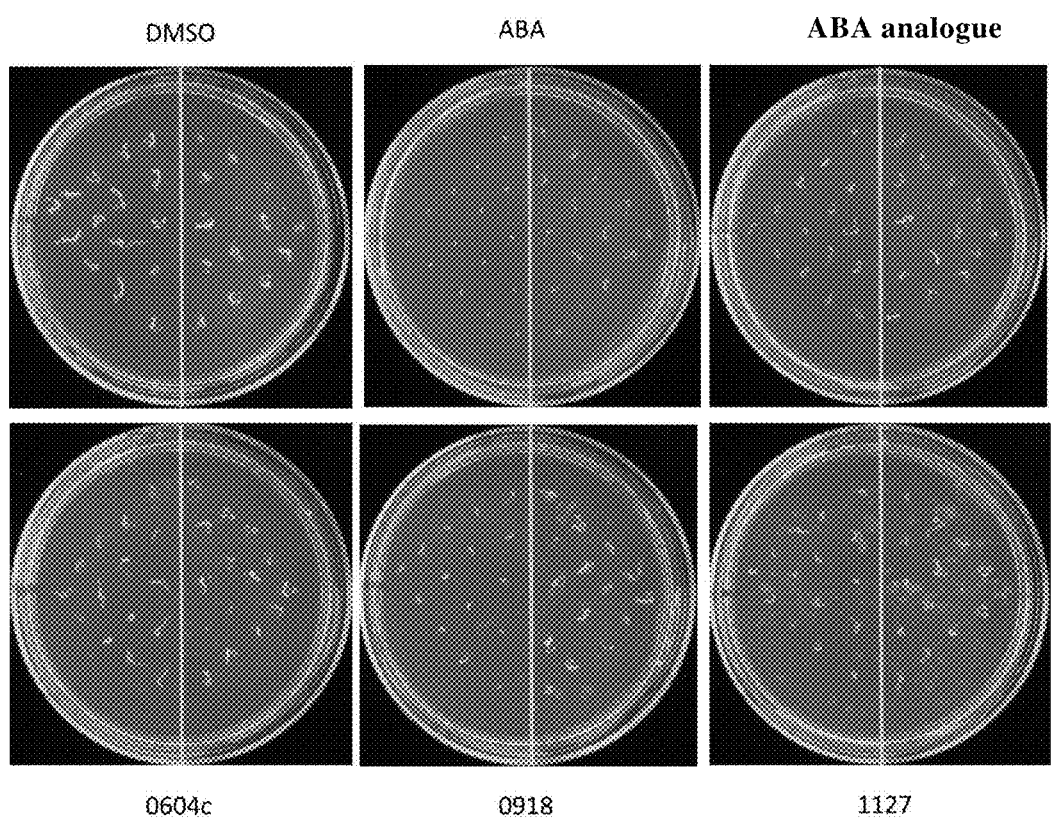
FIG. 6 shows the effects of different AMX compounds and ABA on seed germination of Col-0 and pyr1;pyl1;pyl4 triple mutant at a concentration of 1 μM. Col-0 is sown on the left half of each culture dish and the pyr1;pyl1;pyl4 triple mutants are sown on the right half. After 4 days of seed germination (6 days after sowing) of pyr1;pyl1;pyl4 triple mutants, the photos are taken. DMSO treatment is a control group.

The result was shown in FIG. 6. Six days after seeding, 1 μM of control compound AM1, compound 0604c, compound 0918, compound 1127 or ABA could still inhibit germination of Col-0 ecotype seeds, but could not inhibit germination of PYR/PYL triple mutant pyr1;pyl1;pyl4 seeds.

The results showed that the germination inhibition effect of the AMX compounds was due to activation of an intrinsic ABA signaling pathway in plant, without causing toxicity to the plant seed. Two of AMX compounds (compound 0918 and compound 1127) showed significantly better inhibition effect on germination of Col-0 ecotype seeds than that of the control compound.

20.2 Leaf Transpiration of *Arabidopsis*

In this experiment, the temperature change of leaf surface was observed and recorded by the infrared camera, thus reflecting the strength of plant transpiration.

Figure 7A:
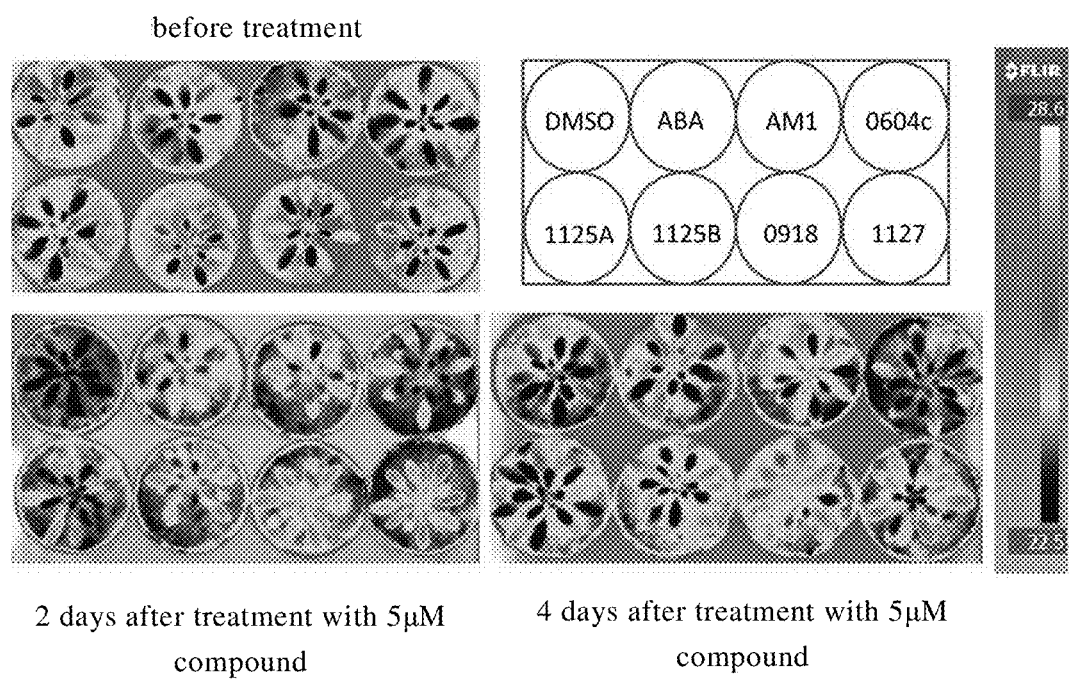
FIGS. 7a and 7b show that the treatment of AMX compounds of the present invention significantly reduces the transpiration rate of *Arabidopsis* leaf, resulting in an increased leaf temperature.
Figure 7B:
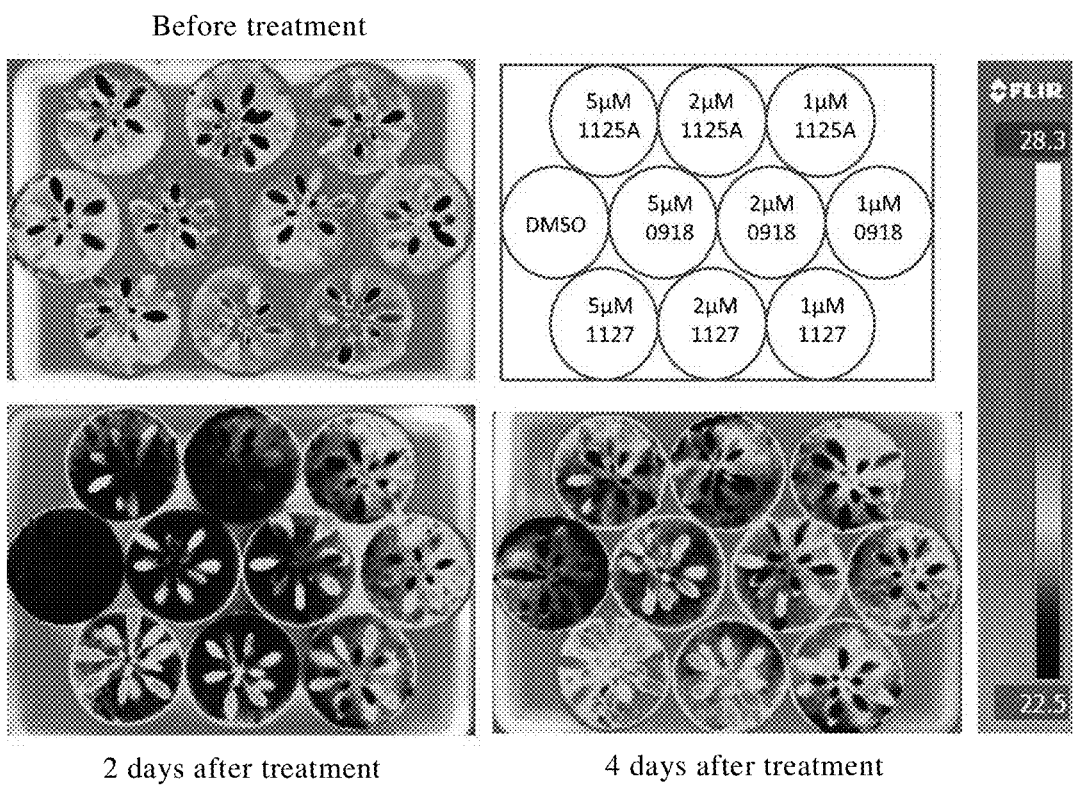

Leaf transpiration experiment results of *Arabidopsis* were shown in FIG. 7a. After two days of spraying *Arabidopsis thaliana* with 5 μM of control compound ABA, control compound AM1 and various AMX compounds, the leaf surface temperature was higher than that of DMSO control group, indicating that the transpiration of compound-treated plants was weakened. After spraying for 4 days, the leaf temperature of plants treated with compound 0918 or compound 1127 was still higher than that in the control group, while leaf temperature of the plants treated with the other compounds had been dropped to a level in the DMSO control group. Concentration gradient experiment showed that there was a dose-dependent effect for inhibition of transpiration by AMX compounds (FIG. 7b), and the effect was positively correlated with the concentration of compound used and the number of halogen atoms in the compound.

Figure 10:
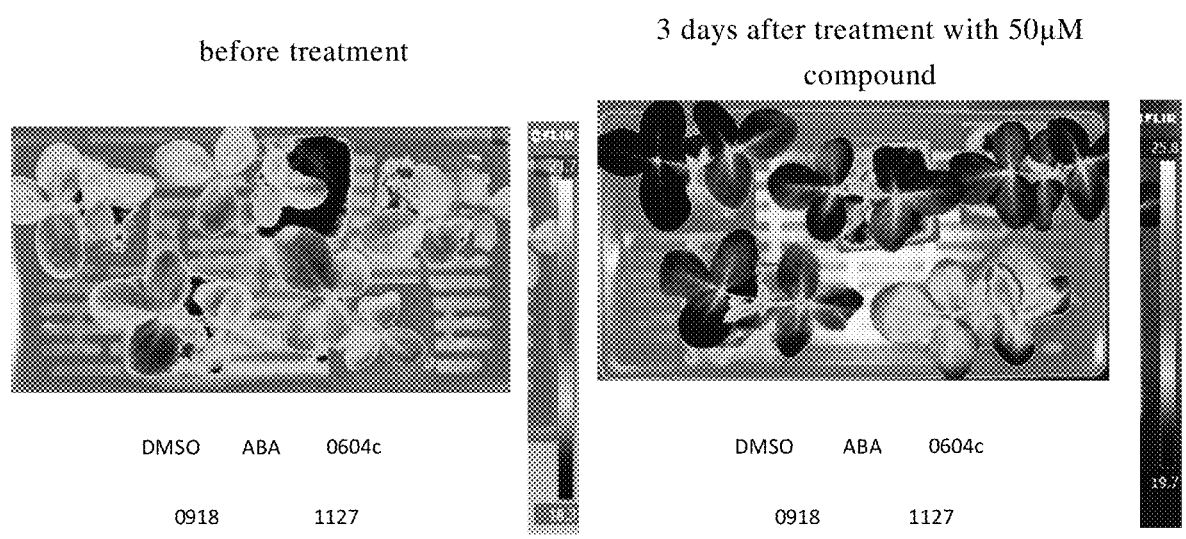
FIG. 10 shows that the transpiration rate of the *Arabidopsis* leaf can still be significantly reduced after 3 days of treatment with 50 μM of AMX compound 1127, resulting in an increased leaf temperature.

The transpiration inhibition experiment on soybean leaf showed that, for plants sprayed with 50 µM of compound 1127 with an amount of 0.2 µmol for each plant, after three days, the leaf temperature was still significantly higher than that in the DMSO-sprayed control. The results showed that the transpiration of soybean leaves was still inhibited at that time, while the leaf temperature of the plants sprayed with the same concentration of ABA had no difference with the control (FIG. 10). This showed that compound 1127 also had the same effect of inhibiting leaf transpiration in soybean as that in *Arabidopsis thaliana*.

20.3 Drought Resistance of *Arabidopsis*

Figure 8:
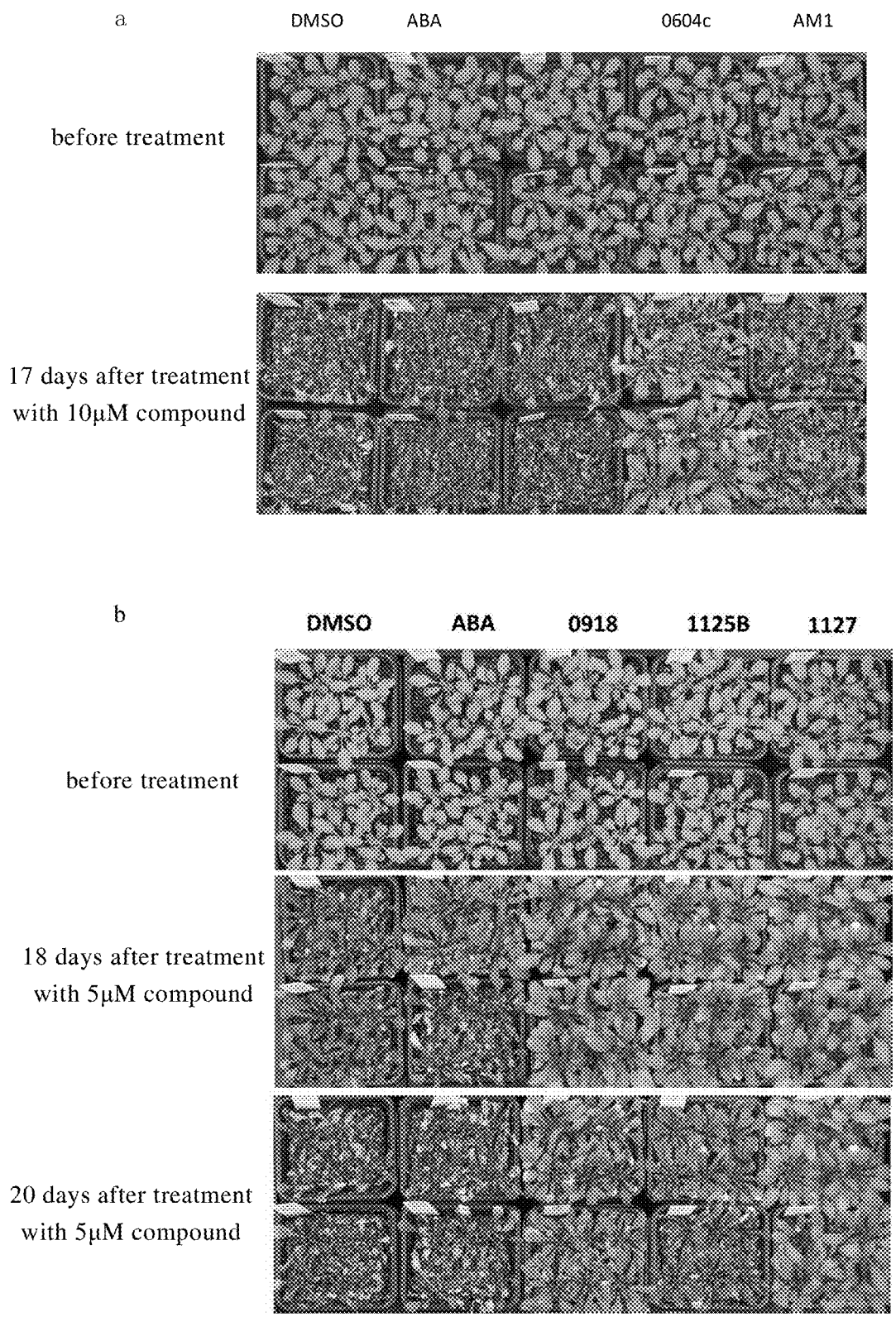
FIG. 8 shows the results of soil drought experiments. For wild-type *Arabidopsis* plants (Col-0), grown for 3 weeks in a short-day environment, watering is stopped and the corresponding concentrations of compounds are sprayed. DMSO is used as a negative control.
Figure 8:
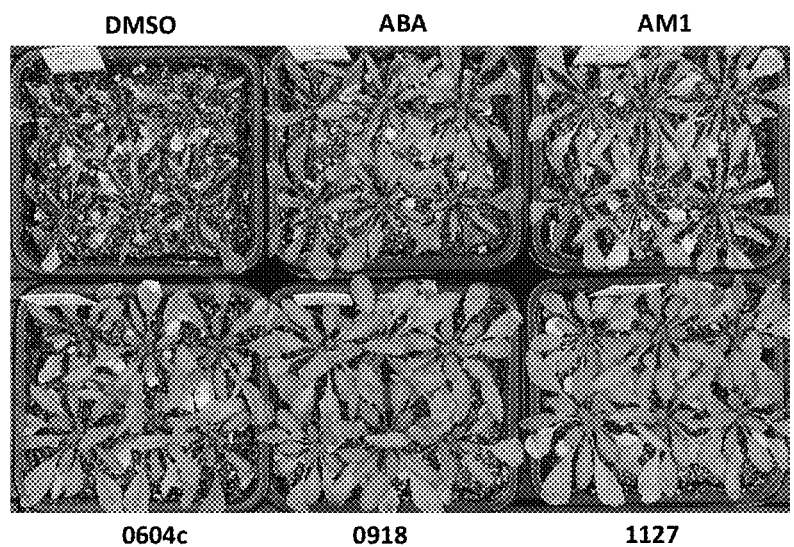

In order to further explore the effect of AMX on plant drought resistance, after Col-0 ecotype of *Arabidopsis thaliana* was grown in soil for two weeks, watering was stopped and the leaves were sprayed once a week with a solution containing corresponding concentrations of (+)-ABA/AM1/AMX or 0.05% of DMSO (control). The solution was sprayed twice, and 0.02% (v/v) of surfactant Tween-20 was added simultaneously to enhance the penetration of the sprayed substance into epidermis of leaves. After 17 days of drought treatment, the control group sprayed with DMSO and the plants sprayed with 10 µM of ABA and AM1 all died because of drought, while the plants sprayed with 10 µM of 0604c still survived (FIG. 8a). After the concentration was lowered to 5 µM, the plants sprayed with compound 0918, compound 1125b or compound 1127 still survived 18 days after drought, whereas plants sprayed with the DMSO (control) and ABA died because of drought, wherein the plants sprayed with compound 1127 still maintained good growth after 20 days of drought (FIG. 8b).

Experiments using structurally similar compounds (such as compound 0604c, compound 0918 and compound 1127) showed that there was a positive correlation between the drought resistance of plants and the number of halogen atoms in the sprayed compounds. After 2 weeks of drought, plants treated with a compound containing more halogen atoms (such as compound 0918 and compound 1127) showed a stronger drought resistance than those treated with a compound containing less number of halogen atoms (such as compound 0604c) at the same concentration (FIG. 8c).

20.4 Drought Resistance of Soybean and Maize

Figure 11:
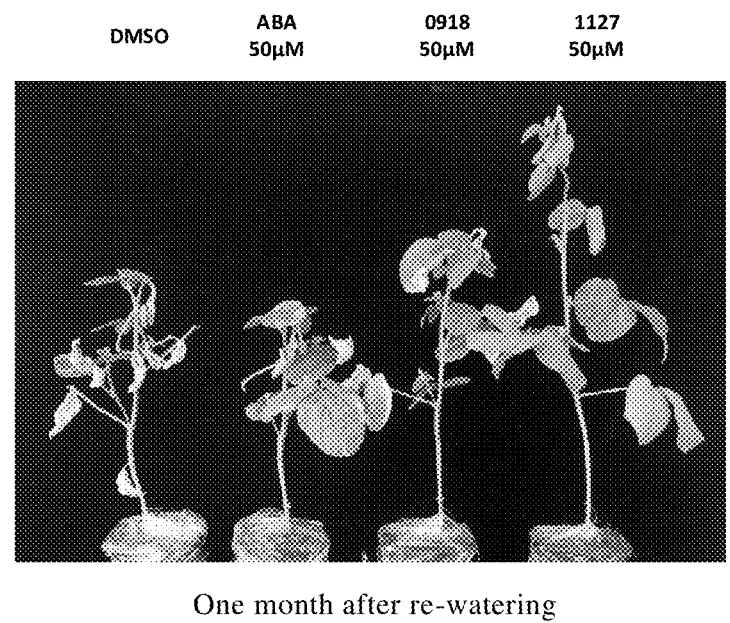
FIG. 11 shows the results of soil drought experiments on soybean and maize. In the soybean experiments, the soybean plants with consistent growth are selected, and re-watered after a week of drought. The photos show the overall growth condition after a month of re-watering. The concentration of each test compound in the experiment is 50 μM. The experimental method for corn is the same with that for soybean. The concentration of compound 0918 in the experiment is 50 μM. Survival rates of soybean and maize treated with AMX after re-watering are significantly higher than that in the control group.
Figure 11:
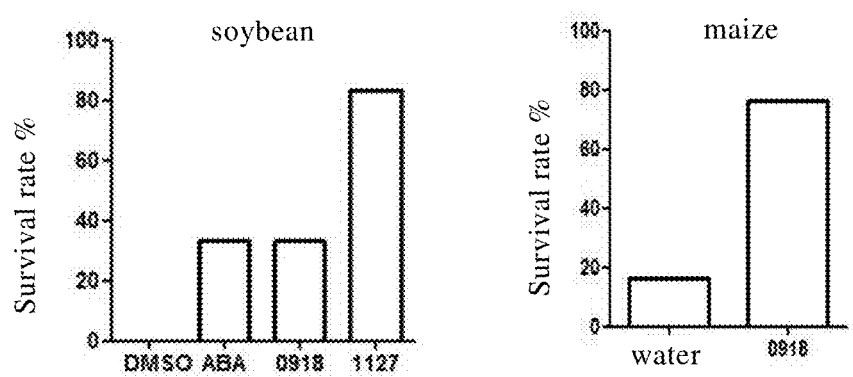

Drought treatment was started when soybean was in trefoil stage or when maize was in bellmouthed stage. The plants of the same size were selected for soil drought experiments. Aqueous solution containing 50 µM of each test compound of AMX or each control compound was sprayed every two days. Similarly, 0.05% (v/v) surfactant Tween-20 was added into the solution. After a week of drought treatment, watering was resumed. After one month of rewatering, the soybean sprayed with 50 µM of compound 0918 or compound 1127 grew significantly better than the plants sprayed with DMSO (control) and sprayed with 50 µM ABA. The survival rate of plants sprayed with compound 0918 was similar to that of the plants sprayed with ABA, while the survival rate of the plants sprayed with compound 1127 was higher than that in the above two groups (FIG. 11). Most of the corn sprayed with compound 0918 survived after rewatering, whereas the control corn sprayed with DMSO did not survive after rewatering (FIG. 11).

The above results showed that the compounds of the present invention could significantly increase the drought resistance of monocotyledonous (maize) and dicotyledonous (soybean) crops.

Specific data of activity of the compounds of invention (the ability to promote the binding of PYR/PYL receptors to the HAB1 protein phosphatase, thereby inhibiting phosphatase activity of the latter) are shown in Table 1.

EXAMPLE 21 Drought Resistance Test of AMX Compound (Compound 0720B)

21.1 Inhibition of Leaf Transpiration in Soybean and Cotton

In this experiment, the temperature change of leaf surface was observed and recorded by an infrared camera, thus reflecting the strength of plant transpiration.

Figure 15:
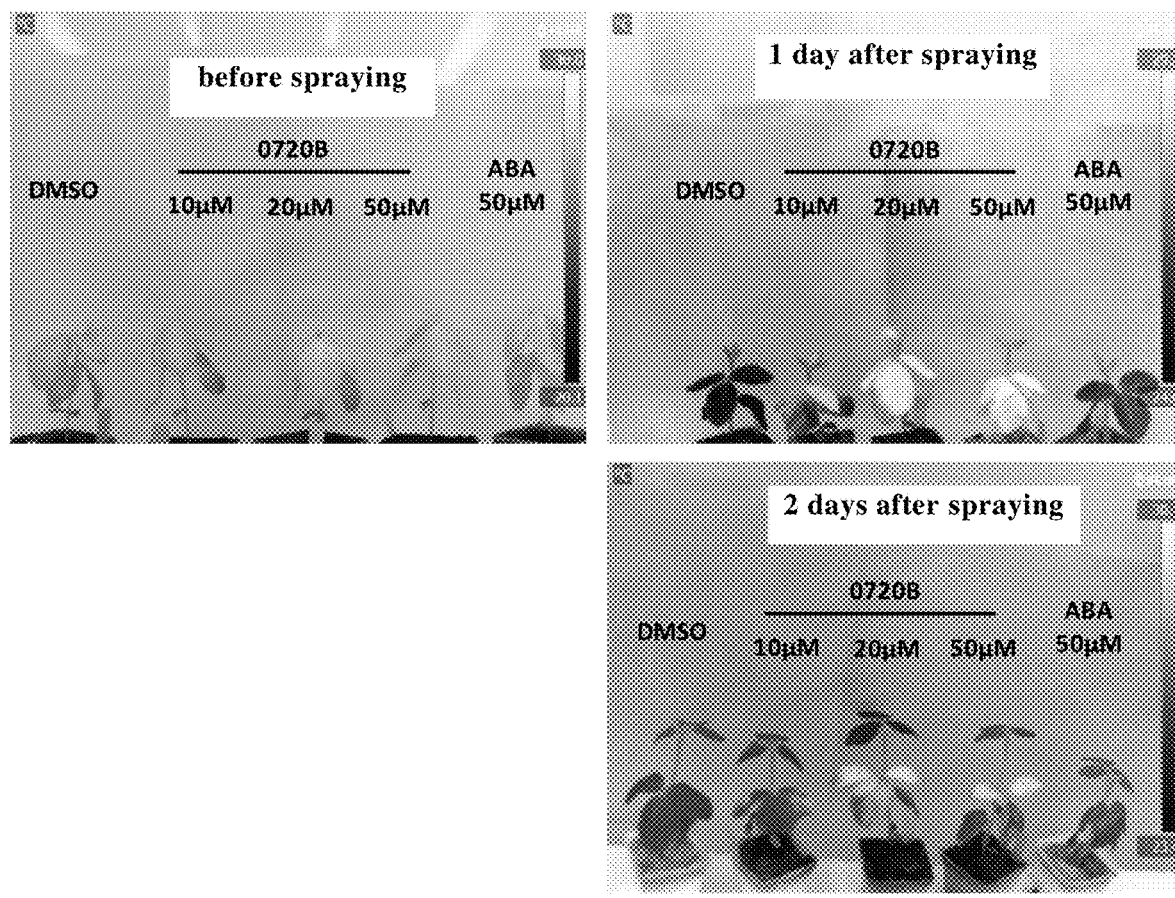
FIG. 15 shows that the transpiration rate of the soybean leaf can be significantly reduced after treatment with AMX compound (0720B), resulting in an increased leaf temperature. For soybean plants, watering are stopped 16 days after seeding and the corresponding compounds are sprayed. Compared with the control group (DMSO), the transpiration rate of soybean leaf can be significantly reduced after 10/20/50 μM of compound 0720B is sprayed, and the inhibitory effect of which is better than that of 50 μM ABA sprayed.
Figure 16:
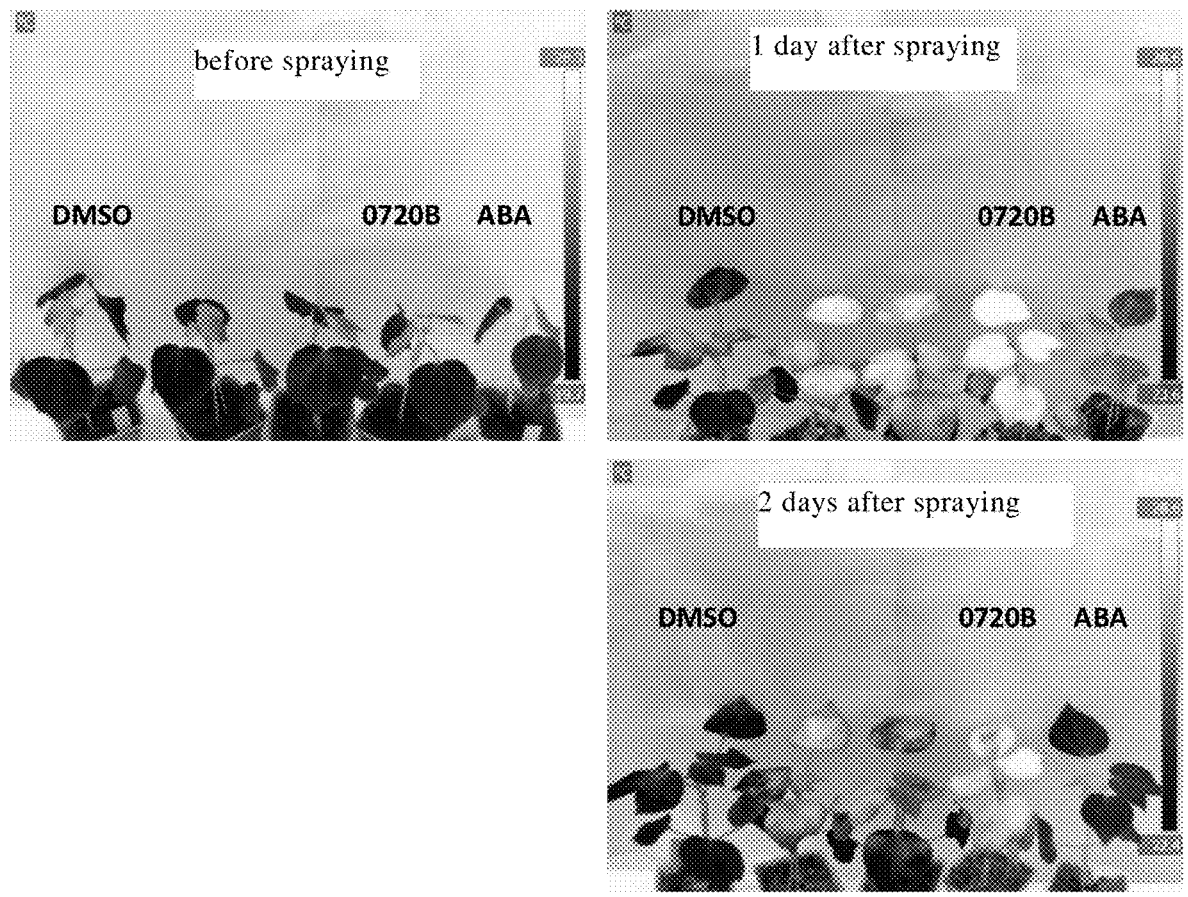
FIG. 16 shows that the transpiration rate of the cotton leaf can be significantly reduced after treatment with AMX compound (0720B), resulting in an increased leaf temperature. For cotton plants, watering are stopped 23 days after seeding, while 50 μM of compound 0720B is sprayed. Compared with the control group (DMSO), 50 μM of compound 0720B can significantly reduce the transpiration rate of the cotton leaf, and the inhibitory effect thereof is better than that of 50 μM ABA.

The results of leaf transpiration experiments in soybean and cotton were shown in FIG. 15 and FIG. 16. Experiments on the inhibition of leaf transpiration in soybean showed that, one day after spraying, for the plants sprayed respectively with 10 µM, 20 µM, or 50 µM of 0720B compound, the leaf temperature was significantly higher than that of plants in DMSO-sprayed control and that of plants sprayed with 50 µM ABA. It indicated that the compound-treated plants had a weaker transpiration than the latter. Two days after spraying, the leaf temperature of the plants sprayed with 20 µM or 50 µM compound 0720B was significantly higher than that of the DMSO-sprayed control, indicating that transpiration of the soybean leaf was still inhibited at that time, while leaf surface temperature of the plant sprayed with 50 µM ABA had no difference from that in the control group (FIG. 15). Experiment results on inhibition of leaf transpiration in cotton showed that, after two days, leaf temperature in plants sprayed with 50 µM 0720B compound was significantly higher than that in plants sprayed with DMSO whereas leaf temperature in plants sprayed with 50 µM ABA had no difference from that in the control group (FIG. 16).

The above results showed that compound 0720B had a significantly better inhibitory effect on leaf transpiration in soybean and cotton than ABA.

21.2 The Enhanced Drought-Resistance in Soybean and Cotton

Figure 17:
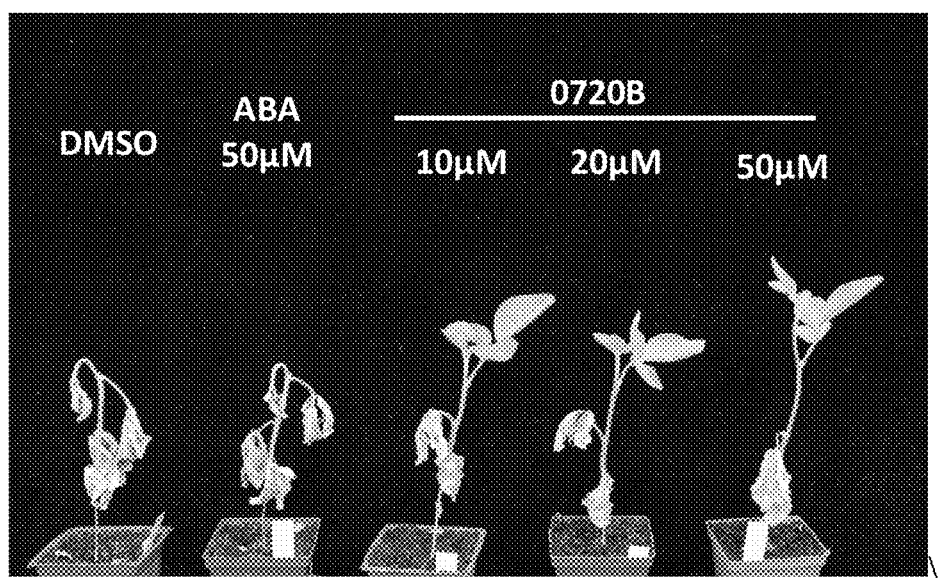
FIG. 17 shows the experimental result of soybean soil drought. The soybean in FIG. 15 is re-watered after 11 days of drought and the photo shows the status of soybean growth one day after re-watering. The growth of soybeans treated with 10/20/50 μM of compound 0720B is significantly better than that in the control group (DMSO) or that of the soybean treated with 50 μM of ABA.
Figure 18:
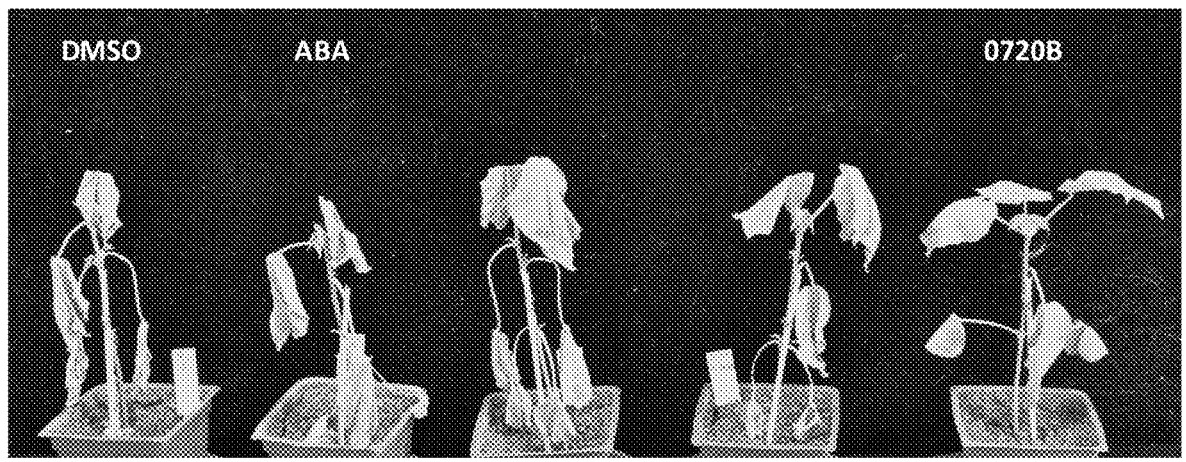
FIG. 18 shows the experimental results of cotton soil drought. The photograph shows the growth condition of the cotton in FIG. 16 after 10 days of drought. The growth of cotton treated with 50 μM of compound 0720B is significantly better than that in the control group (DMSO) or that of the cotton treated with 50 μM of ABA.

Sixteen days after sowing for soybean and twenty-three days after sowing for cotton, the plants with same size were selected for soil drought experiments. Soybean was sprayed with a aqueous solution containing 10 µM, 20 µM, or 50 µM of 0720B or 50 µM ABA once every 3 days after the start of drought. Cotton was sprayed with an aqueous solution containing 50 µM of ABA or compound 0720B once every 4 days after the start of drought. For soybean and cotton drought experiments, an aqueous solution containing 0.05% DMSO was used as control group, and 0.1% (v/v) surfactant Tween-20 was added into the above solution to enhance penetration of the sprayed substance into epidermis of leaves. Soybean was rewatered 11 days after drought, and the growth of soybean sprayed with 10 µM, 20 µM, or 50 µM of compound 0720B after the rewatering was significantly better than that of the plants sprayed with DMSO (control) and the plants sprayed with 50 µM ABA (FIG. 17). After 10 days of drought, the growth of cotton sprayed with 50 µM of compound 0720B was also significantly better than that of the plants sprayed with DMSO (control) and the plants sprayed with 50 µM ABA (FIG. 18).

Specific data of activity of the compounds of invention (the ability to promote the binding of PYR/PYL receptors to the HAB1 protein phosphatase, thereby inhibiting phosphatase activity of the latter) are shown in Table 1.

TABLE 1

List of activity of representative compounds of formula I

| Compound ID | Structure | $R_1$ | $R_2$ | $R_3$ | $R_4$ | $R_5$ | $R_6$ | $R_0$ | Half maximum effect concentration $EC_{50}$ (PYL2 + HAB1) (−: <100 μM +: 10-100 μM ++: 1-10 μM +++: 0.1-1 μM ++++: 0.01-0.1 μM) | inhibition ratio Z of HAB1 relative enzyme activity (PYL2 + HAB1) (inhibition ratio Z of HAB1, at 0.1 μM, Z = Inhibition ratio of HAB1 enzyme activity in the presence of ABA/ Inhibition ratio of HAB1 enzyme activity in the presence of test compound) |
|---|---|---|---|---|---|---|---|---|---|---|
| 0604c | Ia | H | F | H | H | $CH_3$ | H | | ++++ (0.04) | 121% |
| 1125A | Ia | F | H | H | H | $CH_3$ | H | | ++++ (0.03) | 158% |
| 1125B | Ia | H | F | H | F | $CH_3$ | H | | ++++ (0.02) | 199% |
| 0918 | Ia | F | F | H | H | $CH_3$ | H | | ++++ (0.03) | 133% |
| 1127 | Ia | F | F | F | F | $CH_3$ | H | | ++++ (0.02) | 148% |
| 1020A | Ia | H | F | H | H | $CF_3$ | H | | ++++ (0.08) | NA |
| 1020B | Ia | F | F | F | F | $CF_3$ | H | | ++++ (0.08) | NA |
| 1103B | Ia | H | Cl | H | H | $CH_3$ | H | | ++++ (0.05) | NA |
| 0925 | Ia | F | H | H | H | Cl | H | | ++++ (0.06) | NA |
| 0703B | Ib | H | F | H | H | $CH_3$ | H | | NA | 330% |
| 0707 | Ib | F | H | H | H | $CH_3$ | H | | NA | 209% |
| 0714 | Ib | F | F | H | H | $CH_3$ | H | | NA | 148% |
| 0717 | Ib | F | F | F | F | $CH_3$ | H | | NA | 192% |
| 0720B | Ia | F | F | F | F | $CH_3$ | H | $CH_3$ | ++++ (0.03) | 154% |
| 0825A | Ia | F | F | F | F | $CH_3$ | H | $CH_3$ | NA | 107% |
| Control compound 1 (AM1) | Ia | H | H | H | H | $CH_3$ | H | | +++ (0.48) | 86% |
| Control compound 2 (ABA) | | | | | | | | | +++ (0.41) | 100% |

| Compound ID | Half maximum effect concentration $EC_{50}$ (PYL7 + HAB1) (−: >100 μM +: 10-100 μM ++: 1-10 μM +++: 0.1-1 μM ++++: 0.01-0.1 μM) | Half maximum effect concentration $EC_{50}$ (PYR1 + HAB1) (−: >100 μM +: 10-100 μM ++: 1-10 μM +++: 0.1-1 μM ++++: 0.01-0.1 μM) | Half maximum effect concentration $EC_{50}$ (PYR + HAB1) (−: >100 μM +: 10-100 μM ++: 1-10 μM +++: 0.1-1 μM ++++: 0.01-0.1 μM) |
|---|---|---|---|
| 0604c | ++++ (0.03) | ++++ (0.04) | NA |
| 1125A | ++++ (0.04) | ++++ (0.05) | NA |
| 1125B | ++++ (0.02) | ++++ (0.02) | NA |
| 0918 | ++++ (0.02) | ++++ (0.02) | NA |
| 1127 | ++++ (0.01) | ++++ (0.015) | NA |
| 1020A | NA | +++ (0.14) | NA |
| 1020B | NA | ++++ (0.05) | NA |
| 1103B | +++ (0.15) | +++ (0.12) | NA |
| 0925 | NA | ++++ (0.04) | NA |
| 0703B | NA | NA | NA |
| 0707 | NA | NA | NA |
| 0714 | NA | NA | NA |
| 0717 | NA | NA | NA |
| 0720B | NA | NA | ++++ (0.06) |
| 0825A | NA | NA | NA |
| Control compound 1 (AM1) | NA | +++ (0.42) | NA |
| Control compound 2 (ABA) | ++ (1.07) | +++ (0.70) | ++ (3.70) |

As seen from Table 1, the compounds of formula I according to the invention are significantly more active than any of control compounds (1,2) and the number of halogen atoms is proportional to the activity of the compounds.

EXAMPLE 22 Structure of PYL2-AMX-HAB1 Complex

The crystal structure of PYL2-AMX-HAB1 complex formed with several AMX compounds of the present invention was examined using the protein crystal analysis method described in the general method. The control was ABA and the existing ABA analogs. The two-dimensional structure of each complex was shown in FIG. 4.

Figure 4:
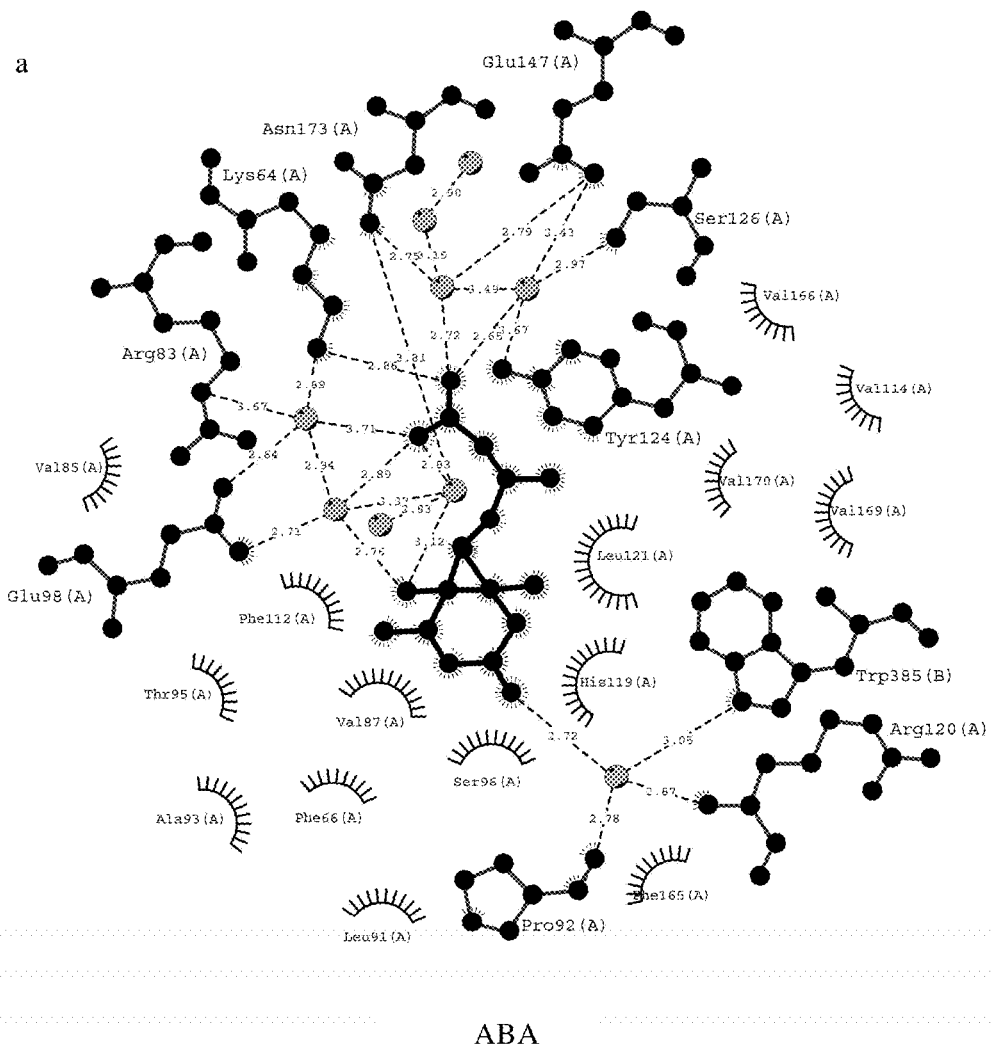
FIGS. 4a to 4i show a two-dimensional (2D) structure of interaction between ABA (a), existing ABA analogs (b) or several AMX compounds (c to i) of the present invention and multiple amino acid residues within the pocket structure of PYL2-HAB1 complex, respectively. Water molecules, nitrogen atoms, oxygen atoms and halogen atoms are shown in the figure, the dotted lines represent hydrogen bonds, and the numbers indicate the distance between two atoms/molecules (the unit is Angstroms (Å)). The results show that, compared with the existing ABA or the analogs thereof, the AMX compounds of the present invention form more hydrogen bonds with the amino acid residues within the PYL2 pocket structure, which allows the a closer binding of AMX to the PYL2-HAB1 complex.
Figure 4:
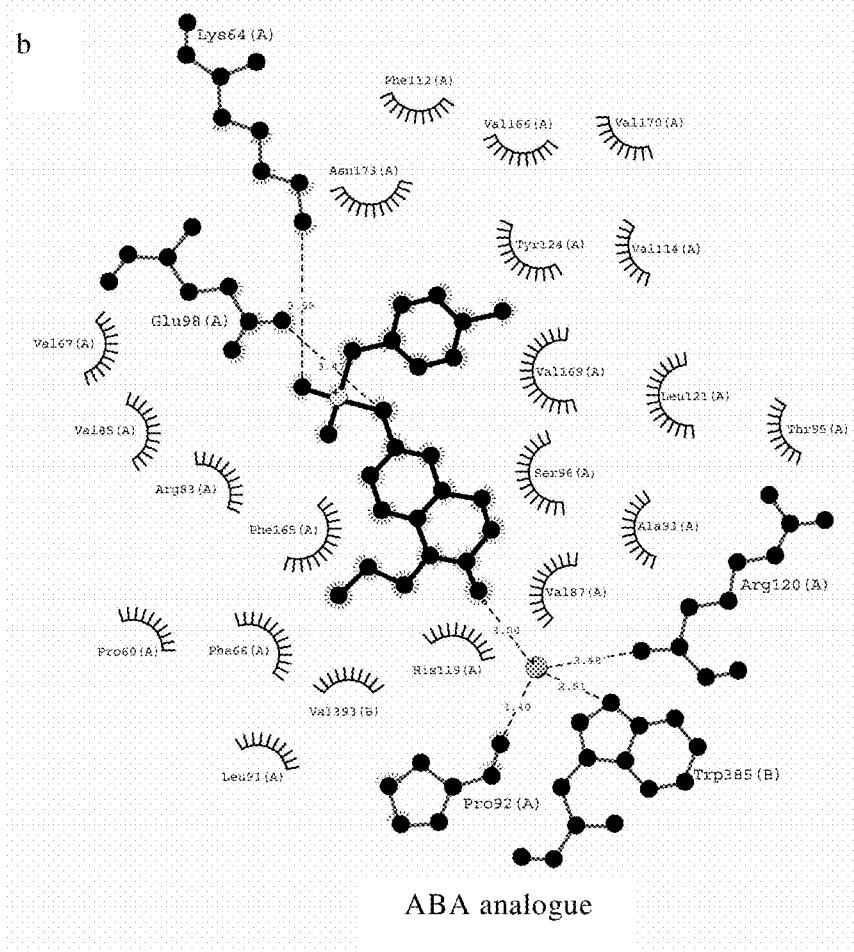
Figure 4:
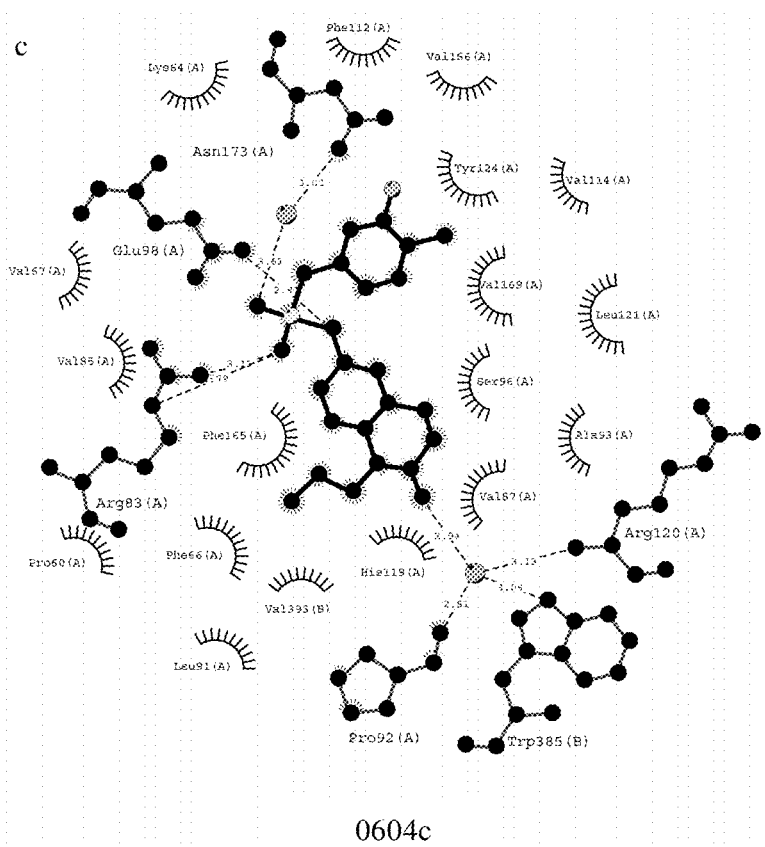
Figure 4:
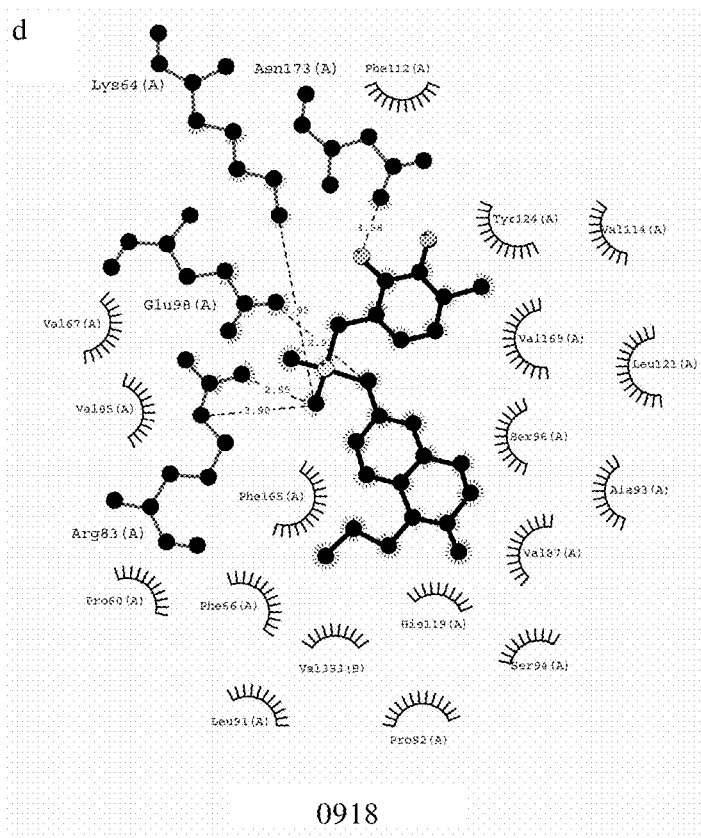
Figure 4:
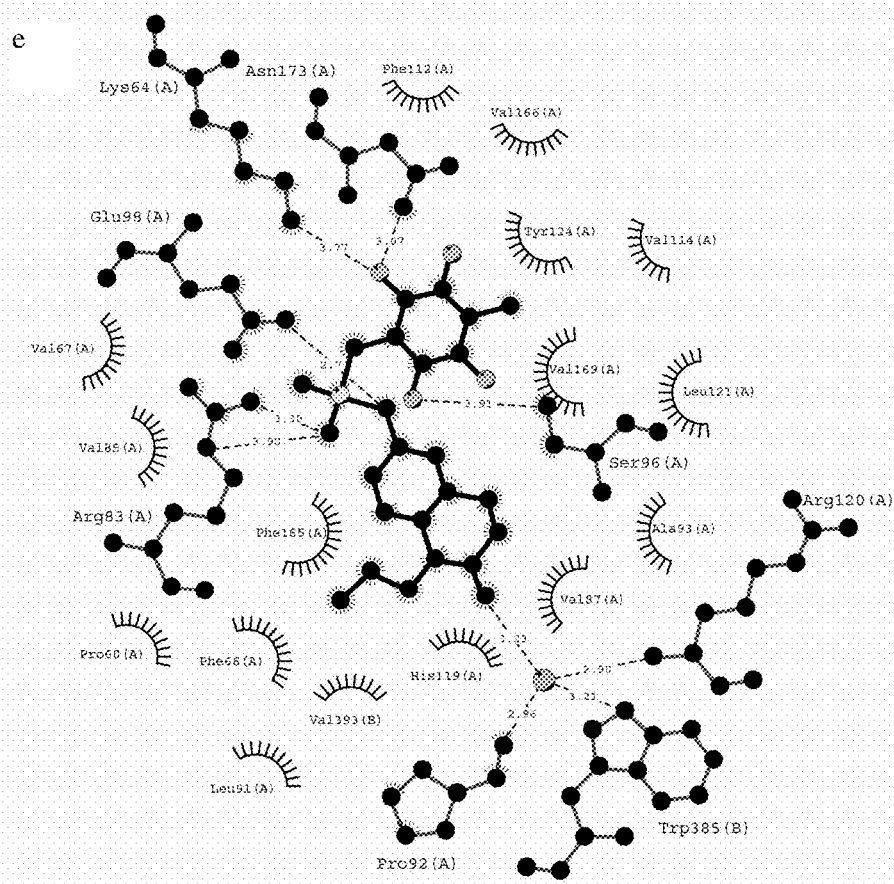
Figure 4:
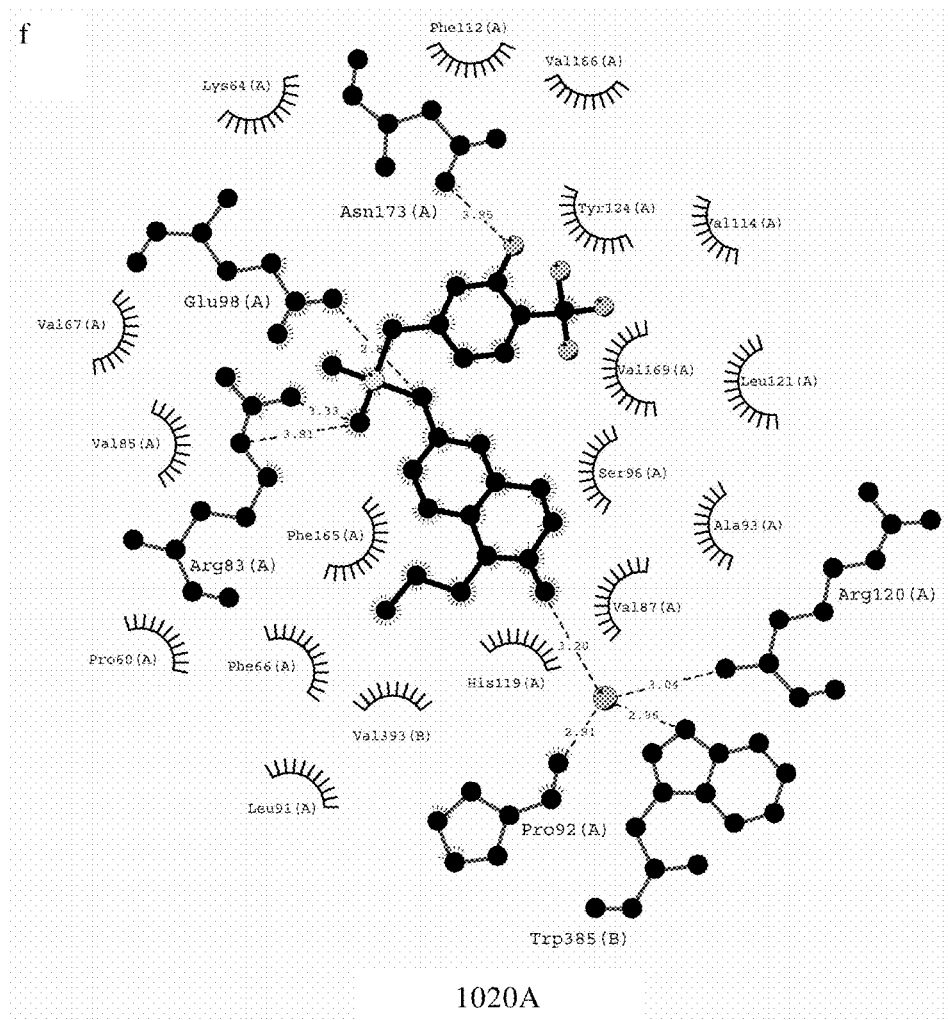
Figure 4:
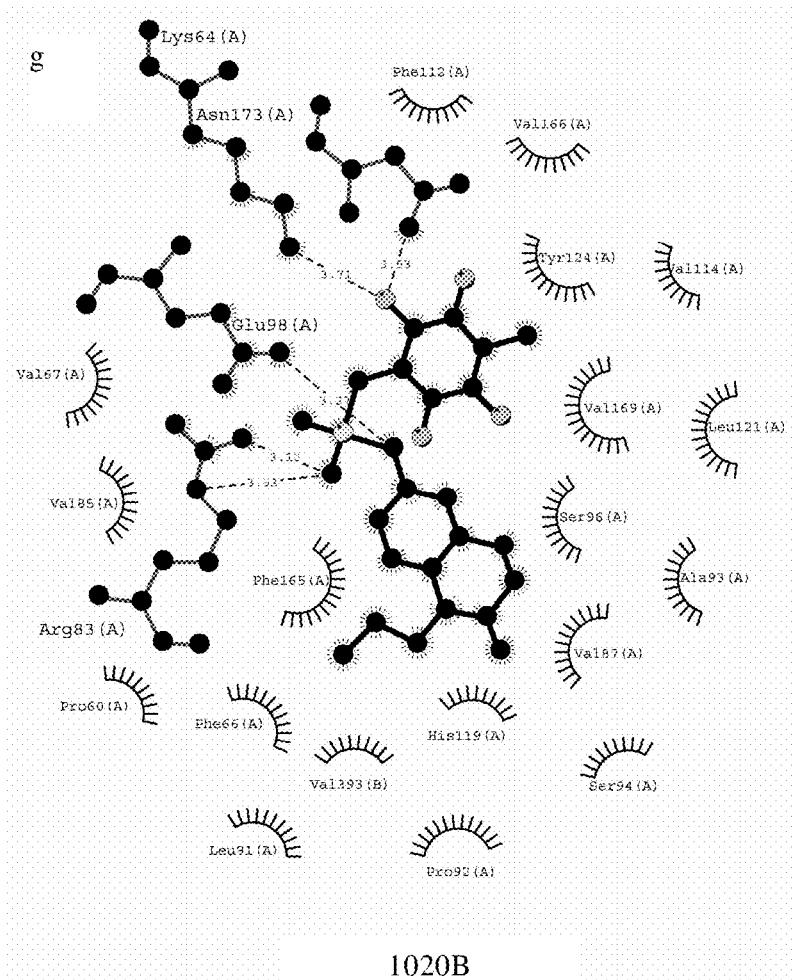
Figure 4:
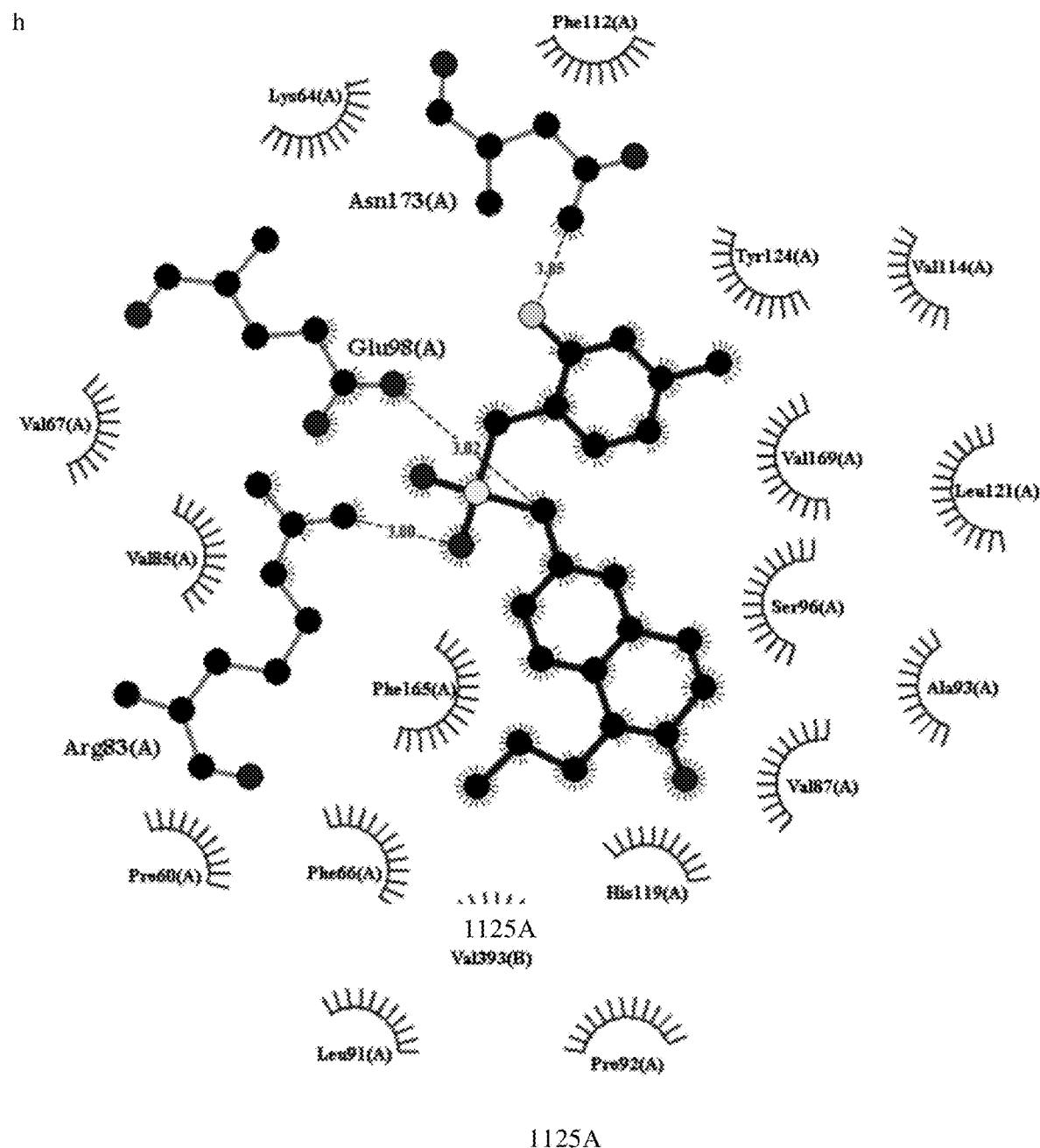
Figure 4:
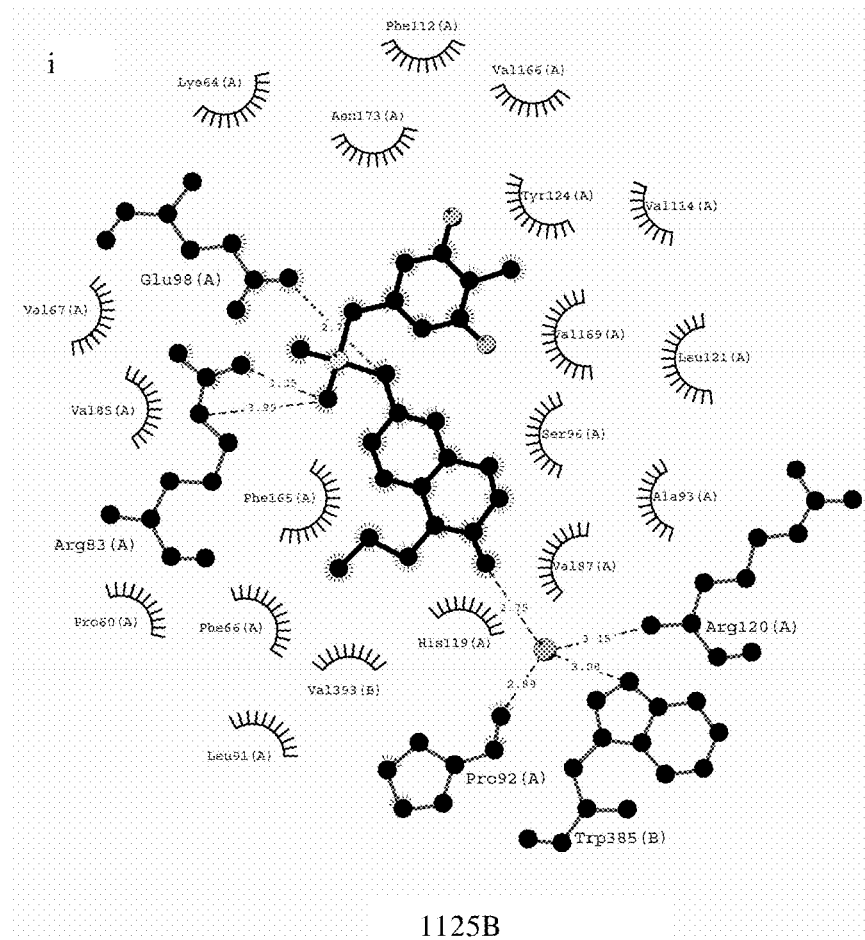

As seen from FIG. 4, AMX was present in the pocket structure of PYL2, and four oxygen atoms on the ABA structure could form hydrogen bonds with multiple amino acid residues in the PYL2 pocket structure and HAB1 by means of several water molecules (FIG. 4a). The oxygen atoms and nitrogen atoms on the sulfonamide group of AMX compounds as well as oxygen atoms on the quinoline ring could also form hydrogen bonds. In addition, the halogen substituents on p-xylene helped oxygen and nitrogen atoms on the sulfonamide group to form hydrogen bonds with more adjacent amino acid residues through steric hindrance or to form hydrogen bonds directly with the PYL2 pocket structure, such as the fluorine atoms in compound 0918 (FIG. 4d), compound 1127 (FIG. 4e), compound 1020A (FIG. 4f), compound 1020B (FIG. 4g), and compound 1125A (FIG. 4h).

It was noticed that, in the presence of methyl or halogen atoms (such as chlorine atoms) in the para position, most of the ortho-fluorine atoms formed hydrogen bonds, the meta-halogen atoms were more likely to use the steric hindrance effect to help the oxygen atoms and nitrogen atoms on the sulfonamide group to form hydrogen bonds with the more proximal amino acid residues. When the halomethyl is in the para position, the meta-fluorine atom could also form a hydrogen bond, such as compound 1020A (FIG. 4f).

In addition, by comparing three groups of structurally similar compounds (Compound 0604c (FIG. 4c), Compound 0918 (FIG. 4d), and compound 1127 (FIG. 4e); compound 1020A (FIG. 4f) and compound 1020B (FIG. 4g); as well as compound 1125A (FIG. 4h) and compound 1125B (FIG. 4i)), it could be found that the number of halogen atoms also had a positive correlation with the number of hydrogen bonds. Compared with the control compound, AMX and PYL2 pocket structure formed more hydrogen bonds or had a stronger binding. Therefore, AMX showed a stronger PYL receptor affinity.

EXAMPLE 23 AMX could Induce ABA-Responsive Stress-Related Gene Expression

The inventors analyzed the effect of exogenously added AMX on expression of plant genes.

Figure 5:
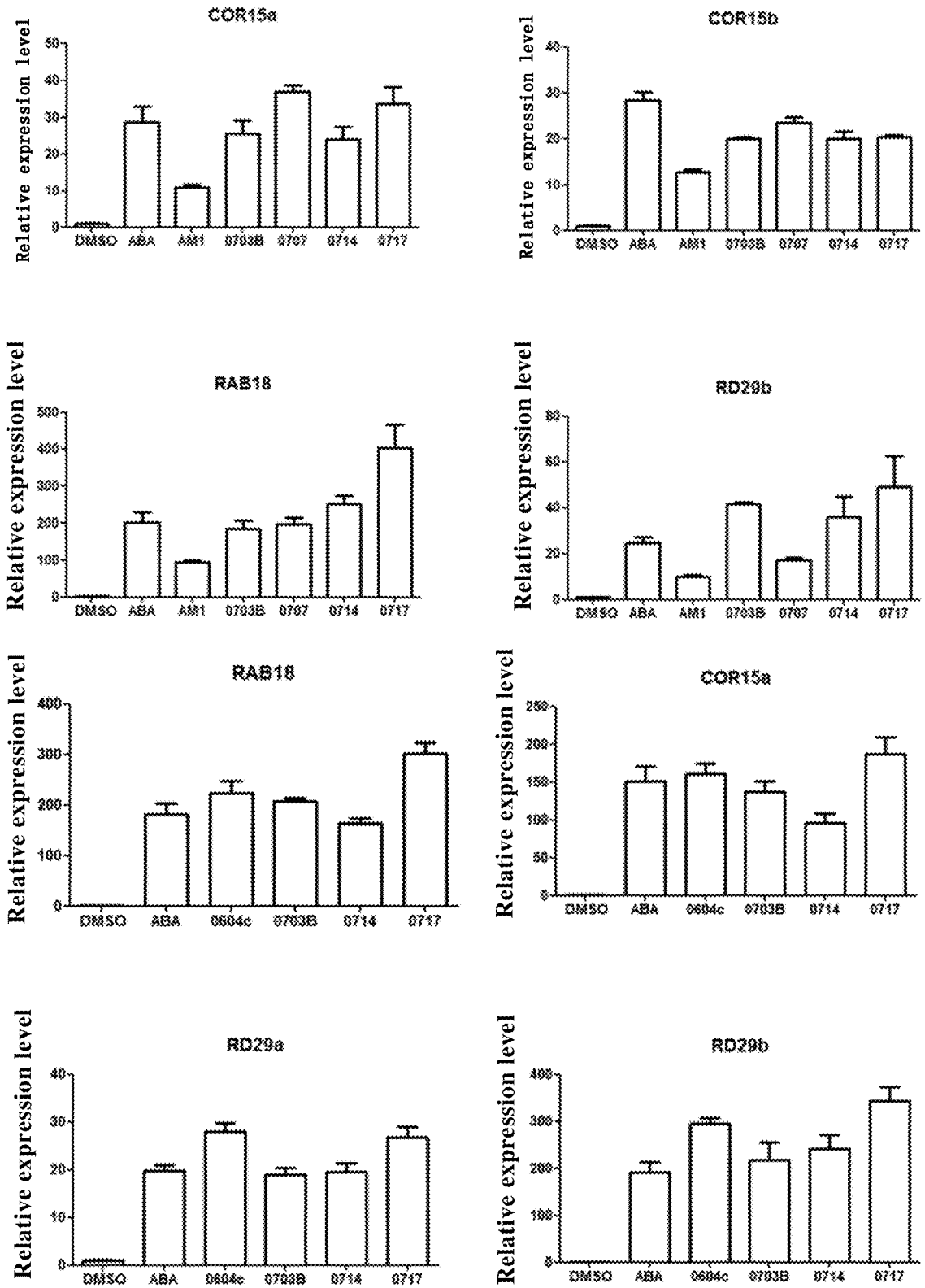
FIG. 5 shows the transcriptional level changes of ABA-induced stress-related genes in wild-type *Arabidopsis* after 6 hours of the treatment with different AMX compounds of the present invention. DMSO and ABA treatments are negative and positive controls, respectively.
Figure 5:
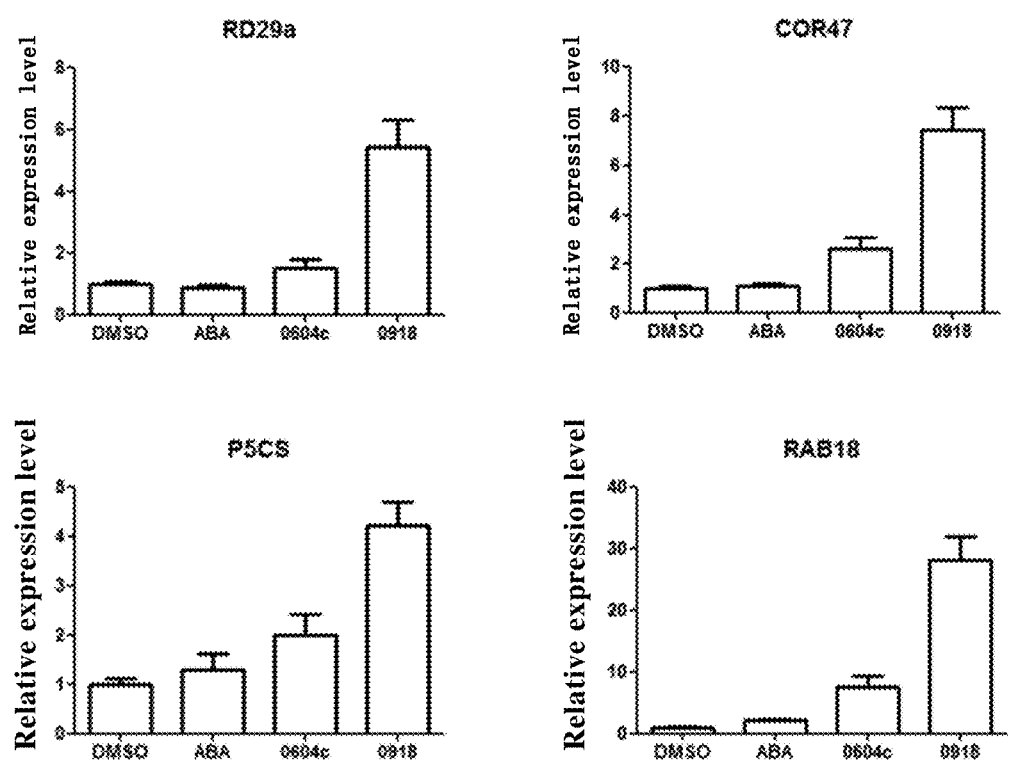

The results of gene expression analysis showed that AMX could induce ABA-responsive stress-related gene expression, and most of the expression levels were up to or higher than that induced by exogenous ABA at the same concentration (FIG. 5). Among 10-day-aged seedling plants of wild-type *Arabidopsis thaliana* (Col-0), 7 known ABA-induced environmental stress-related gene expression were significantly increased after treatment with 10 μM of AMX compound. After 6 hours of treatment with compounds 0604c and 0717, the expression levels of most genes significantly exceeded the level in the plants treated with 10 μM ABA at the same time, whereas 6 hours after treatment with 10 μM AM1, the expression levels of these genes were lower than the level in the plants treated with 10 μM ABA at the same time. In addition, one day after treatment with compound 0604c or compound 0918, the expression level of relevant genes was also significantly higher than that in the plants treated with 10 μM ABA (FIG. 5).

In conclusion, the results showed that the induction effect of AMX on most environmental stress-related genes was significantly better than that of ABA or AM1.

EXAMPLE 24 Plant Preservation (Preservation of Fresh Flowers)

The results showed that the aqueous suspension of AMX Compound 1127 significantly delayed bud withering and leaf withering. After 20 days, in the tap water control group, all flowers withered off and all leaves withered. However, 60% of flowers treated with aqueous suspension of AMX compound 1127 (treatment group) remained normal and no leave withered and 70% of leaves remained green.

EXAMPLE 25 Grape Coloring

Figure 12:
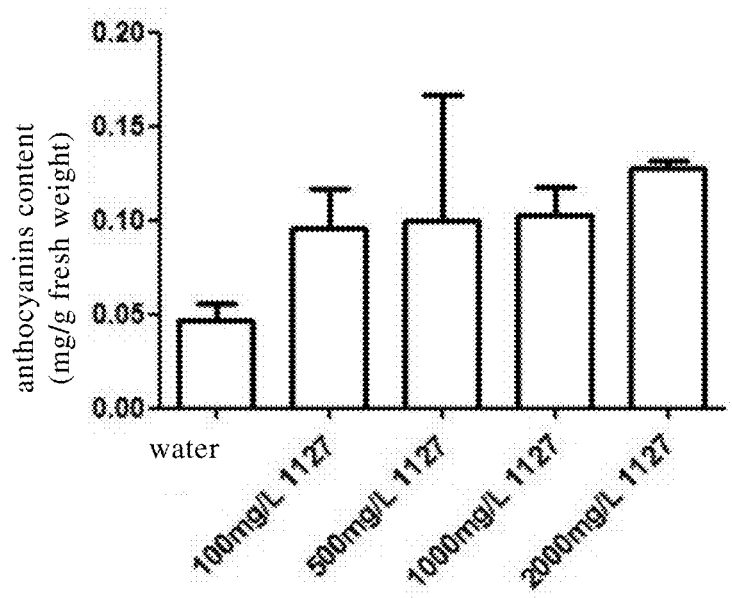
FIG. 12 shows that, after treating with a water suspension of AMX compound 1127, the anthocyanin content of grape peel is significantly higher than that in the control group (clear water). Anthocyanin content is positively correlated with grape peel color.

The experimental results were shown in FIG. 12.

The results showed that the content of anthocyanin in grapes peel treated with AMX compound 1127 in aqueous suspension was significantly higher than that in the fresh water control group. Therefore, the content of anthocyanins was positively correlated with the grape peel color.

EXAMPLE 26 Toxicity Experiment

The results of bacterial reverse mutation assay showed that AMX compound 1127 showed no obvious bacterial toxicity to TA98 and TA100 strains at all doses.

The results of in vitro micronucleus experiments showed that AMX compound 1127 did not induce an increased micronuclei rate in CHL cells under the condition of −S9.

The maximum tolerated dose of the test substance in a single oral gavage experiment in SD rats showed that, in the aspects of the clinical observation, the body weight and the macroscopic morphological observation of the tissues/organs from male and female rats administrated with a dosage of 5000 mg/kg, no drug-related changes were observed and the maximum tolerated dose (MTD) of AMX compound 1127 was greater than 5000 mg/kg.

Those data showed that the AMX compounds of the present invention had a very high safety.

All publications mentioned herein are incorporated by reference as if each individual document was cited as a reference, as in the present application. It should also be understood that, after reading the above teachings of the present invention, those skilled in the art can make various changes or modifications, equivalents of which falls in the scope of claims as defined in the appended claims.

The invention claimed is:

1. A compound of formula (I), or a salt, or an optical isomer, or a racemate, or a solvate thereof, (I)

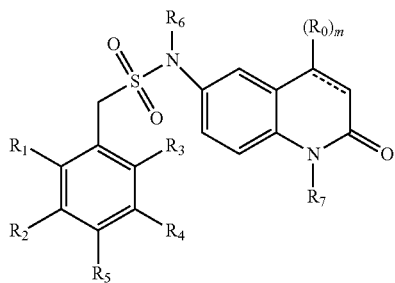

wherein,
$R_1$ is H, halogen, $C_1$-$C_3$ alkyl, or $C_1$-$C_3$ haloalkyl;
$R_2$ is H, halogen, $C_1$-$C_3$ alkyl, or $C_1$-$C_3$ haloalkyl;
$R_3$ is H, halogen, $C_1$-$C_3$ alkyl, or $C_1$-$C_3$ haloalkyl;
$R_4$ is H, halogen, $C_1$-$C_3$ alkyl, or $C_1$-$C_3$ haloalkyl;
$R_5$ is halogen, $C_1$-$C_3$ alkyl, $C_1$-$C_3$ haloalkyl or $SF_5$;
$R_6$ is H, $C_1$-$C_3$ alkyl, or $C_1$-$C_3$ haloalkyl;
$R_7$ is $C_1$-$C_7$ alkyl, $C_2$-$C_7$ alkenyl, $C_2$-$C_7$ alkynyl, $C_3$-$C_7$ cycloalkyl, or —$R_8$—O—$R_9$, wherein $R_8$ is $C_1$-$C_2$ alkylene, whereas $R_9$ is H, $C_1$-$C_3$ alkyl;
$R_0$ is H, $C_1$-$C_4$ alkyl, $C_1$-$C_4$ haloalkyl, or halogen;
m is 1 or 2;
'=====' represents a single bond or a double bond;
provided that 1 to 4 of $R_1$, $R_2$, $R_3$, and $R_4$ are halogen.

2. The compound of claim 1, wherein the compound is of formula Ia, Ib or Ic:

(Ia)

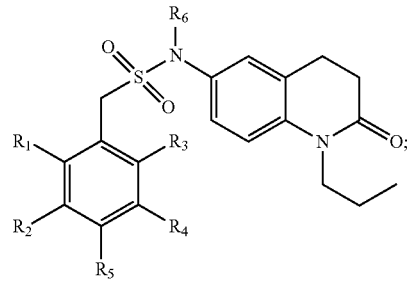

(Ib)

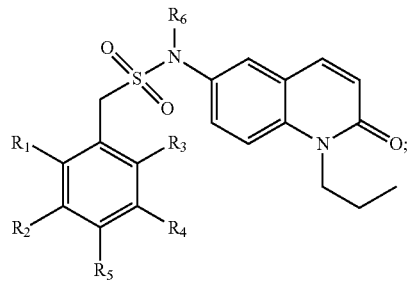

or (Ic)

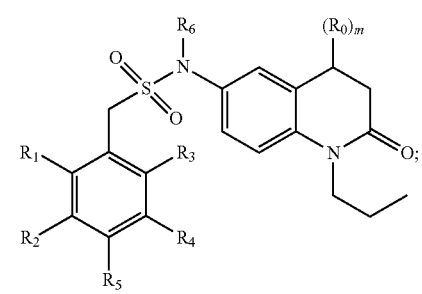

wherein the definitions of $R_0$, $R_1$-$R_6$, and m are described as in claim 1.

3. The compound of claim 1, wherein 2 to 4 of $R_1$, $R_2$, $R_3$, and $R_4$ are halogen, and the definitions of $R_0$, $R_5$-$R_7$, and m are described as claim 1.

4. The compound of claim 1, wherein the compound is selected from the group consisting of:

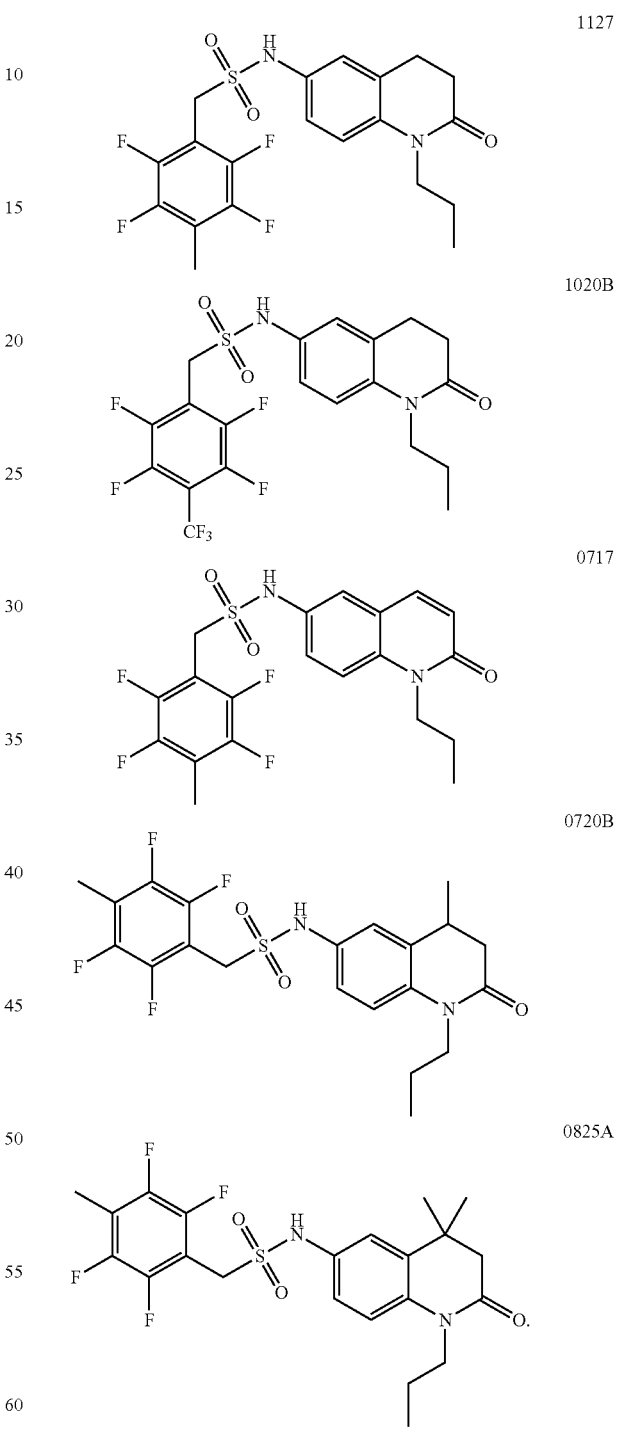

5. The compound of claim 1, further comprising an agriculturally acceptable carrier, for use as an agricultural formulation.

6. A method for enhancing the plant stress resistance, wherein the method comprises administering to a plant the compound of formula I, or a salt, or an optical isomer, or a racemate, or a solvate thereof of claim 1, or the agricultural formulation of claim 5.

7. A method for the treatment of a plant, comprising steps of:
  (a) contacting a plant to be preserved with the compound of formula I, or a salt, or an optical isomer, or a racemate, or a solvate, or a precursor thereof of claim 1, thereby preserving the plant
  or (b) contacting a fruit to be colored with the compound of formula I, or a salt, or an optical isomer, or a racemate, or a solvate, or a precursor thereof of claim 1, thereby coloring the fruit.

* * * * *